US006841546B2

(12) United States Patent
Draper et al.

(10) Patent No.: US 6,841,546 B2
(45) Date of Patent: Jan. 11, 2005

(54) SUBSTITUTED TETRACYCLINE COMPOUNDS AS ANTIFUNGAL AGENTS

(75) Inventors: Michael Draper, Plaistow, NH (US); Mark L. Nelson, Wellesley, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 10/097,457

(22) Filed: Mar. 14, 2002

(65) Prior Publication Data

US 2003/0100017 A1 May 29, 2003

Related U.S. Application Data

(60) Provisional application No. 60/275,948, filed on Mar. 14, 2001.

(51) Int. Cl.$^7$ .......................... A61K 31/65; A01N 37/18
(52) U.S. Cl. ...................................... 514/152
(58) Field of Search ........................ 514/152

(56) References Cited

U.S. PATENT DOCUMENTS

| | | | |
|---|---|---|---|
| 2,980,584 A | 4/1961 | Hammer | 167/65 |
| 2,990,331 A | 6/1961 | Neumann et al. | 167/65 |
| 3,062,717 A | 11/1962 | Hammer | 167/65 |
| 3,165,531 A | 1/1965 | Blackwood et al. | 260/330.5 |
| 3,454,697 A | 7/1969 | Joyner et al. | 424/227 |
| 3,557,280 A | 1/1971 | Weber et al. | 424/80 |
| 3,674,859 A | 7/1972 | Beutel et al. | 424/80 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 4,168,206 A | 9/1979 | Boyer | |
| 5,362,754 A | 11/1994 | Raad et al. | |
| 5,532,227 A | 7/1996 | Golub et al. | 514/152 |
| 5,639,742 A | 6/1997 | Lee et al. | 514/152 |
| 5,688,516 A | 11/1997 | Raad et al. | |
| 5,789,395 A | 8/1998 | Amin et al. | 514/152 |
| 5,834,450 A | 11/1998 | Su | 514/152 |
| 6,509,319 B1 | 1/2003 | Raad et al. | |

FOREIGN PATENT DOCUMENTS

| | | |
|---|---|---|
| DE | 28 14 974 A1 | 10/1978 |
| DE | 28 20 983 A1 | 10/1979 |

OTHER PUBLICATIONS

Hughes, C.E. et al. Enhancement of the in vitro activity of amphotericin B against *Aspergillus* spp. by tetracycline analogs. *Antimicrob. Agents Chemother.* Dec. 1984;26(6):837–40.

Huppert, M. et al. Combined amphotericin B–tetracycline therapy for experimental coccidioidomycosis. *Antimicrob. Agents Chemother.* May 1974;5(5):473–478.

Kwan, C.N. et al. Potentiation of the antifungal effects of antibiotics by amphotericin B. *Antimicrob. Agents Chemother.* Aug. 1972;2(2):61–65.

Lavarde, V. et al. [Effect of minocycline on Candida albicans. "In vitro" study: comparison with tetracycline] *Pathol. Biol.* (French). Nov. 1975;23(9):725–728 (English abstr. provided).

Lew, M.A. et al. Antifungal activity of four tetracycline analogues against *Candida albicans* in vitro: Potentiation by amphotericin B. *J. Infect. Dis.* Aug. 1977;136(2):263–270.

Lew, M.A. et al. Combined activity of minocycline and amphotericin B in vitro against medically imported yeasts. *Antimicrob. Agents Chemother.* Sep. 1978;14(3):465–469.

Nelson, M.L. et al. Inhibition of the tetracycline efflux antiport protein by 13–thio–substituted 5–hydroxy–6–deoxytetracyclines. *J. Med. Chem.* Feb. 5, 1993;36(3):370–377.

Roy, S. Use of tetracycline sorbate for the treatment of *Aspergillus fumigatus* infection in broiler chicks. *Br. Vet. J.* 1991;147:549–555.

Schwartz, S.N. et al. Antifungal properties of polymyxin B and its potentiation of tetracycline as an antifungal agent. *Antimicrobial agents and chemotherapy* Jul. 1972;2:36–40.

Thong, Y.H. et al. Synergism between tetracycline and amphotericin B in experimental amoebic meningoencephalitis. *Med. J. Aust.* Jun. 17, 1978;1:663–664.

Waterworth, P.M. The effect of minocycline on *Candida albicans*. *J. Clin. Path*. 1974;27:269–272.

Koza, D.J. et al. "Synthesis of 7–Substituted Tetracycline Derivatives." *Organic Letters* 2(6):815–817 (2000).

Koza, D.J. et al. "Synthesis and biological evaluation of 9–substituted tetracycline derivatives." *Bioorganic & Medicinal Chemistry Letters* 12:2163–65 (2002).

*Primary Examiner*—Kevin E. Weddington
(74) *Attorney, Agent, or Firm*—Lahive & Cockfield, LLP; Elizabeth A. Hanley, Esq.; Cynthia M. Soroos, Esq.

(57) ABSTRACT

Methods and compositions for treating fungal associated disorders in subjects are discussed.

114 Claims, No Drawings

SUBSTITUTED TETRACYCLINE COMPOUNDS AS ANTIFUNGAL AGENTS

RELATED APPLICATIONS

This application claims priority to U.S. Provisional Application Ser. No. 60/275,948, filed Mar. 14, 2001, entitled "Substituted Tetracycline Compounds as Antifungal Agents," incorporated herein by reference in its entirety.

BACKGROUND OF THE INVENTION

For many years, the development of effective therapeutic agents for fungal diseases (mycoses) has lacked the attention devoted to drugs effective against other infective organisms. The most common mycotic infections are superficial in nature, are not life threatening, and provide little medical impetus to pharmaceutical companies to develop novel treatments. This scenario is changing, however, and while death from fungal disease is not new, the incidence of systemic fungal infections that cause these fatalities is increasing. Ironically, advances in modern medical techniques in other fields (immunosuppressive and/or cytotoxic therapy) and the advent of disease such as Acquired Immuno Deficiency Syndrome (AIDS) are major contributing causes to the increased number of serious fungal infections.

Fungal associated disorders can, thus, be divided into the life-threatening systemic infections, such as histoplasmosis, systemic candidiasis, aspergillosis, blastomycosis, coccidioidomycosis, paracoccidioidomycosis, and cryptococcosis, and the more common superficial ones, such as dermatophyte (ringworm) infections, for example, tinea pedis (athlete's foot) and tinea cruris (jock itch), candidiasis, and actinomycosis. The life-threatening fungal infections are a growing problem not only for immunosuppressed or immunocompromised individuals as noted above but individuals with other viral infections, such as cytomegalovirus (CMV), and influenza, for cancer patients receiving chemotherapy or radiotherapy, for transplant patients receiving antirejection agents, and for patients that have received toxic chemicals, metals and radiation exposure.

Mycoses are often caused by fungi which are opportunists, rather than pathogens. Candidiasis, aspergillosis, phycomycosis, nocardiosis, and cryptococcosis are typically opportunistic fungal infections. For example, *Candida albicans*, is normally found in the alimentary tract as a commensal, yet it is a major cause of systemic fungal infections in immunocomprised patients and topical infections in healthy individuals.

Most drugs currently available for the treatment of mycoses have limited efficacy or are poorly tolerated. A persistent and vexatious problem with antifungal agents, largely unattended by the prior art, is the lack of an agent that is easy and economical to synthesize, and possesses high activity and broad spectrum activity against organisms, low toxicity and limited adverse effects.

Moreover, many known agents merely have fungistatic properties, rather than fungicidal properties. Fungistatic activity is the ability to prevent growth of fungi, while fungicidal (fungitoxic) activity is the ability to kill the fungi. Many agents used in the treatment of superficial mycoses are virtually devoid of either fungistatic or fungicidal actions in the concentrations used, and their beneficial effects probably depend upon factors not related to any direct effect on fungi.

Despite a plethora of agents which have or are alleged to have antifungal properties, most are simply fungistatic and not fungitoxic. For those that are fungicidal, for example, amphotericin B, there are severe adverse side effects which limit their use and their chemical properties, e.g., solubility, limit drug delivery method.

SUMMARY OF THE INVENTION

Although opportunistic systemic fungal infections have a high morbidity and mortality and their incidence is increasing, the art has yet to provide a safe, effective water soluble, simple-to-synthesize, fungitoxic agent with a broad antifungal spectrum of activity coupled with limited adverse effects and low toxicity.

In one embodiment, the invention pertains, at least in part to a method for inhibiting the growth of a fungus. The method includes contacting the fungus with an effective amount of a substituted tetracycline compound, such that the growth of said fungus is inhibited. In a further embodiment, the substituted tetracycline compound is of formula I:

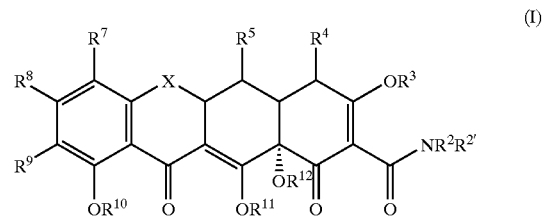

X is $CHC(R^{13}Y'Y)$, $CR^{6'}R^6$, S, $NR^6$, or O;

$R_2$, $R_{2'}$, $R_{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^4R^{4''}$, alkyl, alkenyl, alkynyl, hydroxyl, halogen, or hydrogen;

$R^3$, $R^{11}$ and $R^{12}$ are each hydrogen, or a pro-drug moiety;

$R^{10}$ is hydrogen, a prodrug moiety, or linked to $R^9$ to form a ring;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or $-(CH_2)_{0-3}NR^{7c}C(=W)WR^{7a}$;

$R^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., $-N=S$), or $-(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$ S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

The invention also pertains to a method for treating a fungal associated disorder in a subject. The method includes administering to the subject an effective amount of a substituted tetracycline compound such that the subject is treated for the fungal associated disorder.

The invention also pertains to pharmaceutical compositions, which contain an effective amount of a substituted tetracycline compound to treat a fungal associated disorder in a subject and a pharmaceutically acceptable carrier.

The invention also pertains to a method of killing fungus, by contacting the fungus with a substituted tetracycline compound of the invention, such that the fungus is killed.

DETAILED DESCRIPTION OF THE INVENTION

In addition to their well known antibacterial properties, minocycline and doxycycline have been shown to possess limited antifungal activity both alone and in synergy with amphotericin B (*Antimicrob. Agents Chemother.* (1984), 26(6)837–40; *Pathol. Biol.* (1975) 23(9):725–8). The invention pertains, at least in part, to methods and pharmaceutical compositions comprising substituted tetracycline compounds with enhanced antifungal activity.

In an embodiment, the invention pertains to methods for inhibiting the growth of a fungus. The method includes contacting the fungus with an effective amount of a substituted tetracycline compound, such that the growth of the fungus is inhibited.

The terms "fungus" or "fungi" include a variety of nucleated, sporebearing organisms which are devoid of chlorophyll. The term includes all fungi whose growth can be inhibited by the compounds of the invention. Examples include, but are not limited to, yeasts, mildews, molds, rusts, and mushrooms. Examples of fungi also include, but are not limited to *Aspergillus fumigatus, Aspergillus flavus, Aspergillus nidulans, Candida albicans, Candida glabrata, Candida guilliermondii, Candida krusei, Candida lusitaniae, Candida parapsilosis, Candida tropicalis, Cryptococcus neoformans, Issatchenkia orientalis,* Coccidioides, Paracoccidioides, Histoplasma, Blastomyces, and *Neurospora crassa*. In one embodiment, the fungi of the invention includes fungi of the genus Candida (e.g., *C. tropicalis, C. parapsilosis, C. lusitaniae, C. krusei, C. guilliermondii, C. glabrata, C. dubliniensis,* and *C. albicans*).

The term "inhibiting the growth of a fungus" includes both fungistatic and fungicidal activity. Fungistatic activity includes any decrease in the rate of growth of a fungal colony. Fungistatic activity may be manifested by a fungus maintaining its present size or failing to colonize the surrounding areas. Fungistatic activity may be a result of inhibition of the fungal reproductive processes. Fungicidal activity generally includes, for example, irradiatication of a fungus or fungal colony, killing a fungus or fungal colony or, in one embodiment, a decrease in the mass or size of a fungus or fungal colony.

The term "tetracycline compounds" includes tetracycline family members such as methacycline, sancycline, apicycline, clomocycline, guamecycline, meglucycline, mepylcycline, penimepicycline, pipacycline, etamocycline, penimocycline, etc. as well as other tetracycline compounds having the characteristic naphthacene A-B-C-D ring structure. Additional tetracycline compounds can be found, for example, in U.S. patent application Ser. No. 09/234,847, and U.S. Pat. Nos. 5,834,450; 5,532,227; 5,789,395; 5,639,742 and German patents DE 28 14 974 and DE 28 20 983. The entire contents of the aforementioned applications and patents are hereby expressly incorporated herein by reference.

Recent research efforts have focused on developing new tetracycline compositions effective under varying therapeutic conditions and routes of administration; and for developing new tetracycline analogues which might prove to be equal or more effective as antibiotics than the originally introduced tetracycline families (See, U.S. Pat. Nos. 3,957,980; 3,674,859; 2,980,584; 2,990,331; 3,062,717; 3,557,280; 4,018,889; 4,024,272; 4,126,680; 3,454,697; and 3,165,531).

The term "substituted tetracycline compounds" includes tetracycline compounds which have at least one substitution, e.g., at the 2, 3, 4, 5, 6, 7, 8, 9, 10, 11, 11a, 12 and 12a position, which allows the compound to perform its intended function, e.g., inhibit the growth of fungus. In an embodiment, the term "substituted tetracycline compounds" does not include unsubstituted tetracycline, minocycline, or doxycycline. In an embodiment, the substituted tetracycline compounds of the invention have lower MIC for Candida fungus (as measured in the assay given in Example 2) than doxycycline or minocycline. In one embodiment, the substituted tetracycline compounds of the invention have MIC's for a fungus which is about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, or about 1% or less than the MIC of unsubstituted tetracycline, unsubstituted doxycycline, or unsubstituted minocycline for that particular fungus. Values and ranges included and/or intermediate within the ranges set forth herein are also intended to be within the scope of the present invention. For example, a MIC of less than 10% includes MIC's of 9%, 8%, 7%, 6%, 5%, 4%, 3%, 2%, 1%, etc., which are intended to be included within the range of less than 10%.

Furthermore, the substituted tetracycline compounds also may advantageously be less cytotoxic than unsubstituted tetracycline, minocycline, or doxycycline. In one embodiment, the cytotoxicity of the substituted tetracycline compounds is about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, or about 1% or less than the cytotoxicity of unsubstituted tetracycline, unsubstituted doxycycline, or unsubstituted minocycline. Values and ranges included and/or intermediate within the ranges set forth herein are also intended to be within the scope of the present invention. For example, a cytoxicity of less than 10% includes cytotoxicities of 9%, 8%, 7%, 6%, 5%, 4%, 3%, 2%, 1%, etc. are intended to be included within the range of less than 10%.

The term "substituted tetracycline compound" includes, for example, substituted sancycline compounds, substituted minocycline compounds and substituted doxycycline compounds.

Substituted tetracycline compounds used in the methods and compositions of the invention include compounds of Formula I:

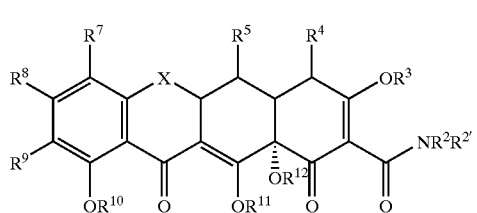

(I)

X is CHC(R$^{13}$Y'Y), CR$^{6'}$R$^6$, S, NR$^6$, or O;

R$^2$, R$^{2'}$, R$^{4'}$, and R$^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^{4'}$R$^{4''}$, alkyl, alkenyl, alkynyl, hydroxyl, halogen, or hydrogen;

R$^3$, R$^{11}$ and R$^{12}$ are each hydrogen, or a pro-drug moiety;

R$^{10}$ is hydrogen, a prodrug moiety, or linked to R$^9$ to form a ring;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —(CH$_2$)$_{0-3}$NR$^{7c}$C(=W')WR$^{7a}$;

R$^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., —N=S), or —(CH$_2$)$_{0-3}$NR$^{9c}$C(=Z')ZR$^{9a}$;

Z is CR$^{9d}$R$^{9e}$, S, NR$^{9b}$ or O;

Z' is O, S, or NR$^{9f}$,

W is CR$^{7d}$R$^{7c}$, S, NR$^{7b}$ or O;

W' is O, NR$^{7f}$ S;

R$^{7a}$, R$^{7b}$, R$^{7c}$, R$^{7d}$, R$^{7e}$, R$^{9a}$, R$^{9b}$, R$^{9c}$, R$^{9d}$, and R$^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In an embodiment, the substituted tetracycline compounds used in the methods and compositions of the invention are substituted sancycline compounds, e.g., with substitution at the, for example, 2, 5, 6, 7, 8, 9, 10, 11, 11a, 12 12a position and/or, in the case of minocycline, 13. In substituted sancycline compounds of the invention, R$^{2'}$, R$^3$, R$^{10}$, R$^{11}$, and R$^{12}$ are each hydrogen or a prodrug moiety; R$^{4'}$ and R$^{4''}$ are each alkyl (e.g., lower alkyl, e.g., methyl); X is CR$^6$R$^{6'}$; and R$^2$, R$^5$, R$^6$, R$^{6'}$, and R$^8$ are each, generally, hydrogen. In other embodiments, In an embodiment, the substituted tetracycline compound is a substituted tetracycline (e.g., generally, wherein R$^4$ is NR$^{4'}$R$^{4''}$, R$^{4'}$ and R$^{4''}$ are methyl, R$^5$ is hydrogen and X is CR$^6$R$^{6'}$, wherein R$^6$ is methyl and R$^{6'}$ is hydroxy); substituted doxycycline (e.g., wherein R$^4$ is NR$^{4'}$R$^{4''}$, R$^{4'}$ and R$^{4''}$ are methyl, R$^5$ is hydroxyl and X is CR$^6$R$^{6'}$, wherein R$^6$ is methyl and R$^{6'}$ is hydrogen); substituted minocycline (e.g., wherein R$^4$ is NR$^{4'}$R$^{4''}$, R$^{4'}$ and R$^{4''}$ are methyl; R$^5$ is hydrogen and X is CR$^6$R$^{6'}$ wherein R$^6$ and R$^{6'}$ are hydrogen atoms and R$^7$ is dimethylamino) or substituted sancycline (wherein R$^4$ is NR$^{4'}$R$^{4''}$, R$^{4'}$ and R$^{4''}$ are methyl; R$^5$ is hydrogen and X is CR$^6$R$^{6'}$ wherein R$^6$ and R$^{6'}$ are hydrogen atoms).

In one embodiment, R$^5$ is substituted, e.g., not hydrogen or hydroxy. In a further embodiment R$^5$ is an ester (alkcarbonyloxy). In an embodiment, R$^5$ is an alkyl ester. Examples of R$^5$ include alkyl esters such as C$_1$–C$_{12}$ alkyl, alkenyl, alkynyl, or aryl esters. The alkyl groups may be straight chains, branched chains, and/or contain rings. Examples of esters include, but are not limited to, tetracycline esters of ethanoic acid, propanoic acid, pentanoic acid, hexanoic acid, 2-cyclopentane ethanoic acid, cyclopentanoic acid, cycloheptanoic acid, 2-methyl propanoic acid, cyclohexanoic acid, and adamantane 2-carboxylic acid. In other embodiments, R$^5$ is hydrogen.

For 7-substituted tetracycline compounds, R$^9$ may be hydrogen. In one embodiment, R$^7$ is substituted or unsubstituted phenyl. Examples of R$^7$ substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In an embodiment, the phenyl is substituted with at least one alkyl group, which itself may be, branched, straight chain or alkyl, unsubstituted or substituted (e.g., halogenated). Examples of alkyl groups include, but are not limited to, methyl, ethyl, propyl, butyl, pentyl, hexyl, heptyl, etc.

In another embodiment R$^7$ is a halogen, e.g., chlorine, bromine, or iodine.

In another embodiment, R$^7$ is substituted or unsubstituted heteroaryl. Examples of heteroaromatic groups include both monocyclic and polycyclic (e.g., multicylic rings), such as, but not limited to, furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl. In an embodiment, R$^7$ is benzofuranyl. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In another embodiment, $R^7$ is substituted or unsubstituted, branched, straight chain or cyclic alkyl. Examples of substituents include those which allow the substituted tetracycline compound to perform its intended function, e.g., inhibit the growth of a fungus. Examples of substitutents include, but are not limited to, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, trialkylsilyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

Examples of alkyl $R^7$ groups include $C_1$–$C_{15}$ groups and $C_1$–$C_{10}$ groups. Examples include 2-ethyl pentyl, methyl, ethyl, propyl, pentyl, hexyl, heptyl, etc.

In one embodiment, $R^7$ is substituted or unsubstituted alkenyl. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In one embodiment, an alkenyl $R^7$ moiety is substituted with a substituted or unsubstituted cyclic moiety. Cyclic moieties include both carbocyclic, heterocyclic, aryl, heteroaryl, cycloalkenyl, and cycloalkyl groups. Examples of cyclic moieties include, for example, cyclobutane, cylopentane, cyclohexane, phenyl, etc. The cyclic moiety can be substituted, e.g., with any substituent listed above for alkenyl $R^7$ moieties.

In another embodiment, $R^7$ is substituted or unsubstituted alkynyl. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

The $R^7$ alkynyl moiety may be substituted with a substituted or unsubstituted cyclic moiety. Cyclic moieties include both carbocyclic, heterocyclic, aryl, heteroaryl, cycloalkenyl, and cycloalkyl groups. Examples of cyclic moieties include, for example, cyclobutane, cylopentane, cyclohexane, phenyl, etc. The cyclic moiety can be substituted, e.g., with any substituent listed above for alkynyl $R^7$ moieties.

Examples of cyclic substituents for alkynyl $R^7$ moieties include, but are not limited to, phenyl, cyclohexyl, p-nitro phenyl, p-methyl phenyl, and 1-hydroxy cyclohexane.

In another embodiment, $R^7$ is substituted or unsubstituted alkoxy. Examples of substituents include all substituents which allow the tetracycline compound to perform its intended function, such as but are not limited to, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In one embodiment, the alkoxy group is $C_1$–$C_{10}$. In another embodiment, it is methoxy, ethoxy, propoxy, butoxy, pentoxy, hexoxy, etc.

In another embodiment, the invention pertains to substituted doxycycline compounds wherein $R^5$ is hydroxy or alkylcarbonyloxy; X is $CHR^6$; $R^6$ is alkyl (e.g., lower alkyl, e.g., methyl); and $R^8$ is hydrogen. $R^7$ may be hydrogen or alkyl. $R^2$ may be hydrogen or alkyl.

In one embodiment, $R^9$ is substituted or unsubstituted aryl, e.g., phenyl, biaryl, heteroaryl (e.g., pyridine, etc.), etc. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

Other examples of $R^9$ include substituted or unsubstituted alkyl (e.g., methyl, ethyl, propyl, t-butyl, n-butyl, i-butyl, pentyl, etc.) or $N_3$.

In another embodiment, the invention pertains to methods and compositions which the substituted tetracycline compound is a substituted minocycline compound. Examples of these compounds include compounds wherein X is $CR^6R^{6'}$; $R^2$, $R^5$, $R^6$, $R^{6'}$, and $R^8$ are each hydrogen, and $R^7$ is dimethyl amino.

In an embodiment, $R^9$ is substituted or unsubstituted aryl (e.g., phenyl, biaryl (naphthyl, benzofuranyl), heteroaryl, etc.) or araalkyl. Examples of substituents include, but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In one embodiment, the aryl $R^9$ moiety is substituted or unsubstituted phenyl.

Other examples of $R^9$ moieties include substituted and unsubstituted, cyclic, branched or straight chain alkyl (e.g., $C_1$–$C_{15}$, $C_1$–$C_{10}$, e.g., methyl, ethyl, propyl, butyl, pentyl, hexyl, 2-cyclopentane ethyl, etc.). Examples of substituents include those listed above for aryl $R^9$ moieties.

In another embodiment, $R^9$ is substituted or unsubstituted, branched, straight chain or cyclic alkyl. Examples of substituents include those which allow the substituted tetracycline compound to perform its intended function, e.g., inhibit the growth of a fungus. Examples of substituents include, but are not limited to, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, trialkylsilyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

Examples of alkyl $R^9$ groups include $C_1$–$C_{15}$ groups and $C_1$–$C_{10}$ groups. Examples include 2-ethyl pentyl, methyl, ethyl, propyl, pentyl, hexyl, heptyl, etc.

In one embodiment, $R^9$ is substituted or unsubstituted alkenyl. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In one embodiment, an alkenyl $R^9$ moiety is substituted with a substituted or unsubstituted cyclic moiety. Cyclic moieties include both carbocyclic, heterocyclic, aryl, heteroaryl, cycloalkenyl, and cycloalkyl groups. Examples of cyclic moieties include, for example, cyclobutane, cylopentane, cyclohexane, phenyl, etc. The cyclic moiety can be substituted, e.g., with any substituent listed above for alkenyl $R^9$ moieties.

In another embodiment, $R^9$ is substituted or unsubstituted alkynyl. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

The $R^9$ alkynyl moiety may be substituted with a substituted or unsubstituted cyclic moiety. Cyclic moieties include both carbocyclic, heterocyclic, aryl, heteroaryl, cycloalkenyl, and cycloalkyl groups. Examples of cyclic moieties include, for example, cyclobutane, cylopentane, cyclohexane, phenyl, etc. The cyclic moiety can be substituted, e.g., with any substituent listed above for alkynyl $R^9$ moieties.

Furthermore, the substituted tetracycline compounds of the invention can be substituted with combinations of any one of the substituents described above or shown in Table 2.

Examples of cyclic substituents for alkynyl $R^9$ moieties include, but are not limited to, phenyl, cyclohexyl, p-nitro phenyl, p-methyl phenyl, and 1-hydroxy cyclohexane.

In a further embodiment, $R^9$ is substituted or unsubstituted aminoalkyl. Examples of substituents include, but are not limited to, alkyl, alkenyl, alkynyl, and aryl substituents.

In one embodiment, the substituted tetracycline compounds for use in the methods and compositions of the invention have a greater antifungal activity than unsubstituted doxycycline or minocycline. Both of these compounds have Minimum Inhibitory Concentrations (MIC) for *C. Albicans, C. giabrata, C. tropicalis*, and *C. parapsilosis* in excess of 64 (See example 2, for the procedure for measuring the MIC).

In another embodiment, the substituted tetracycline compounds of the invention may have anti-inflammatory activity, e.g., as measured in art recognized assays.

In another embodiment, the substituted tetracycline compounds of the invention may be non-antibacterial, e.g., have little or no antibacterial activity. The antibacterial activity of the compounds of the invention can be measured using the assay given in Example 5. In an embodiment, a compound is considered to be non-antibacterial if it has a MIC (against bacteria) of 4 μM or greater.

In another embodiment, the invention also pertains to 4-dedimethylaminotetracycline compounds with the substituents described herein or shown in Table 2 (e.g., compounds with the same substituents as described herein or in Table 2, except at the $R^4$ position where the shown dimethylamino group is a hydrogen.)

Examples of substituted tetracycline compounds for use in the methods and compositions of the invention include the compounds shown in Table 2, as well as those shown below:

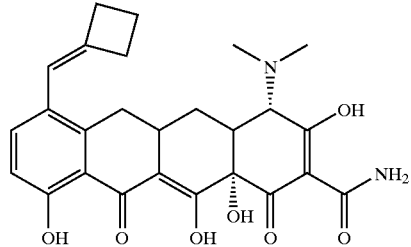

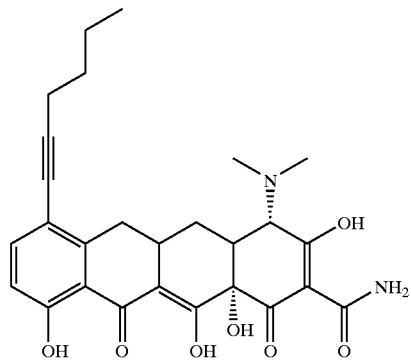

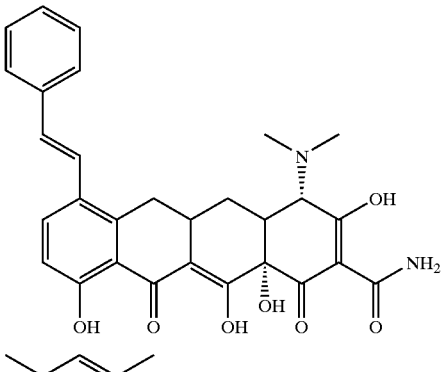

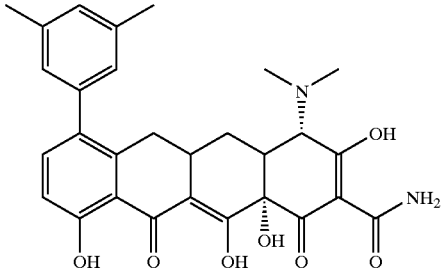

-continued

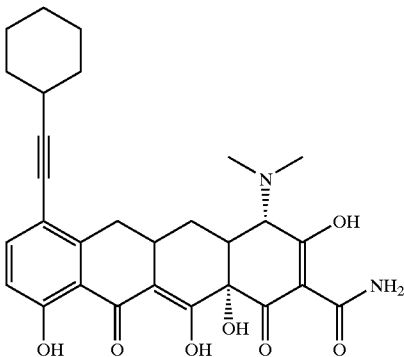

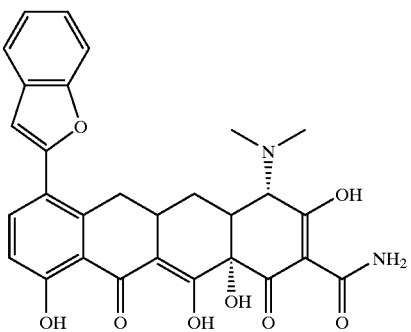

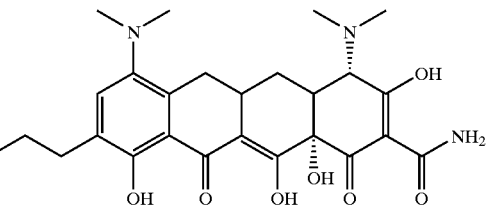

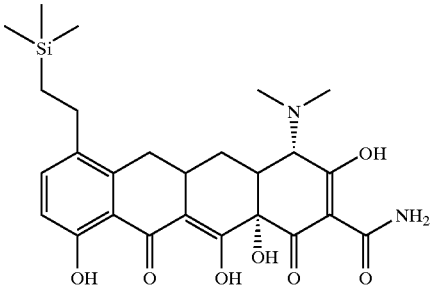

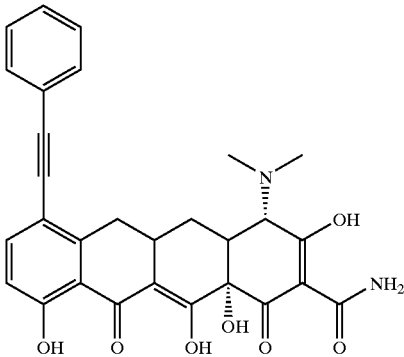

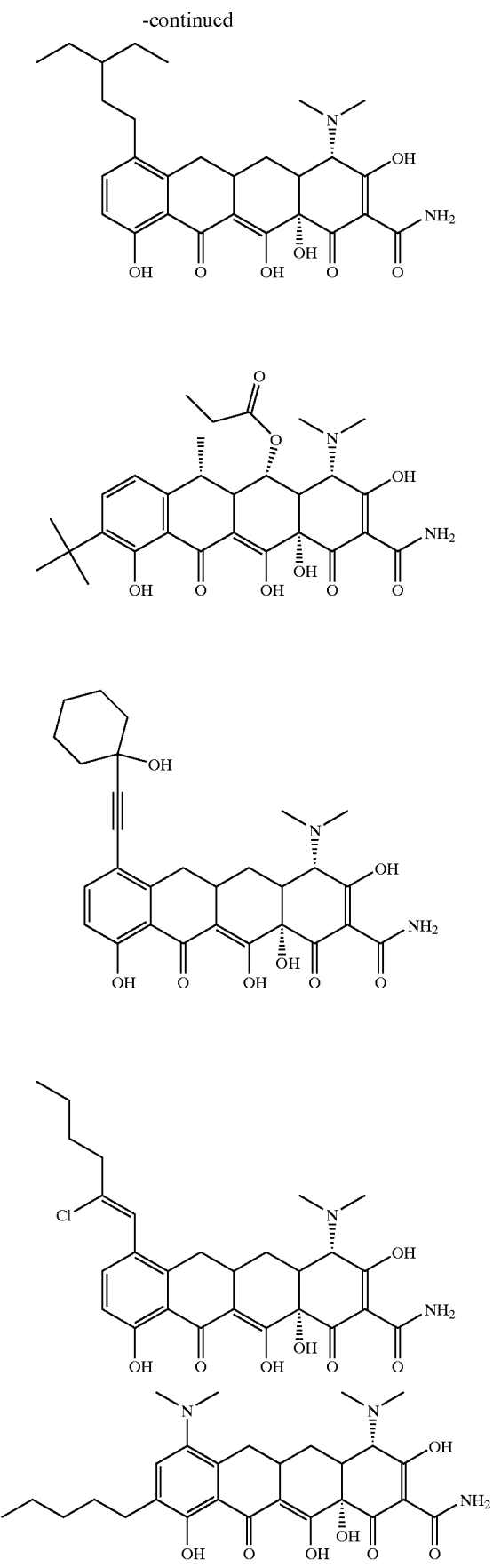
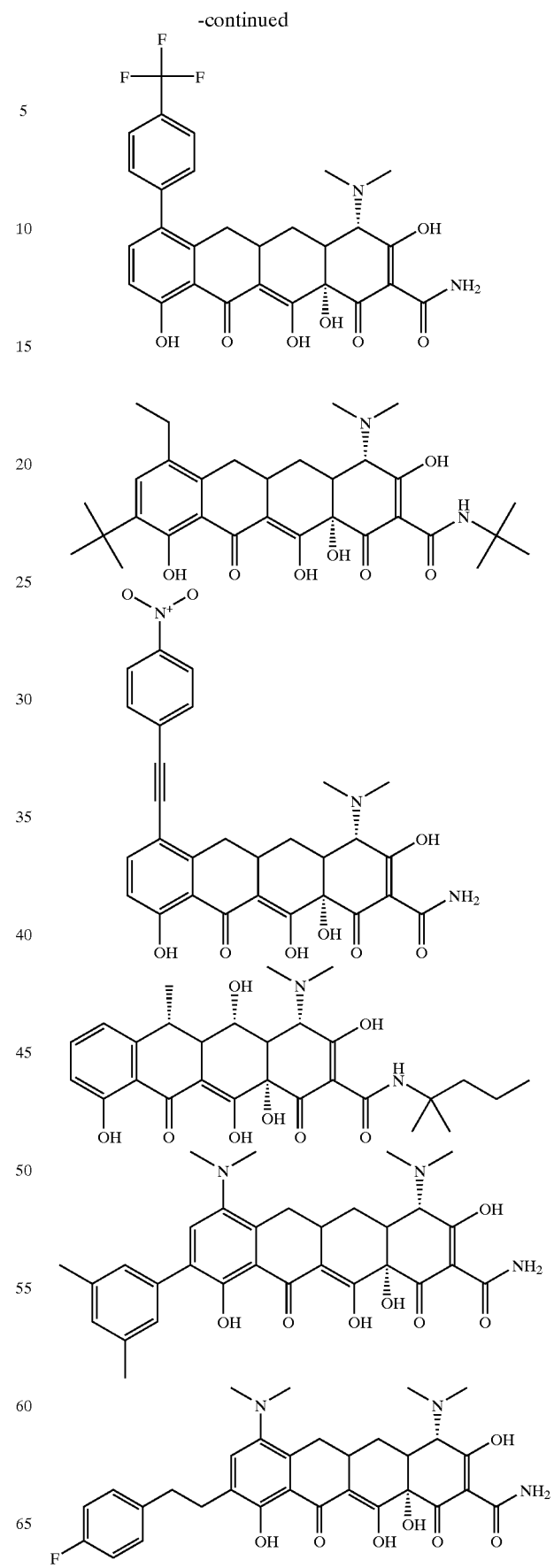

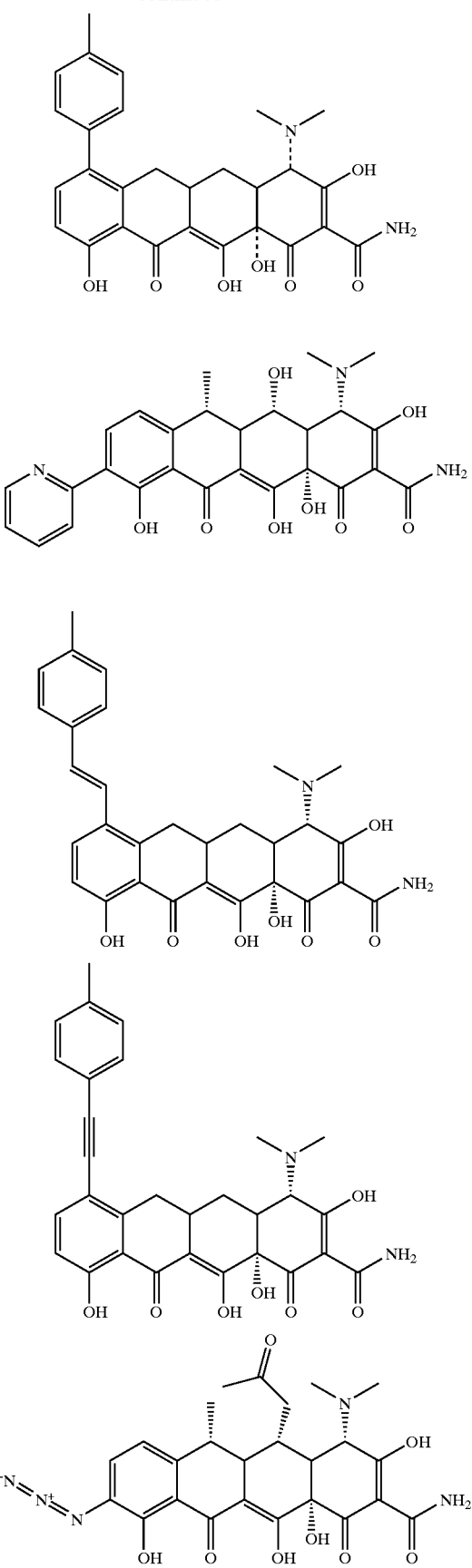

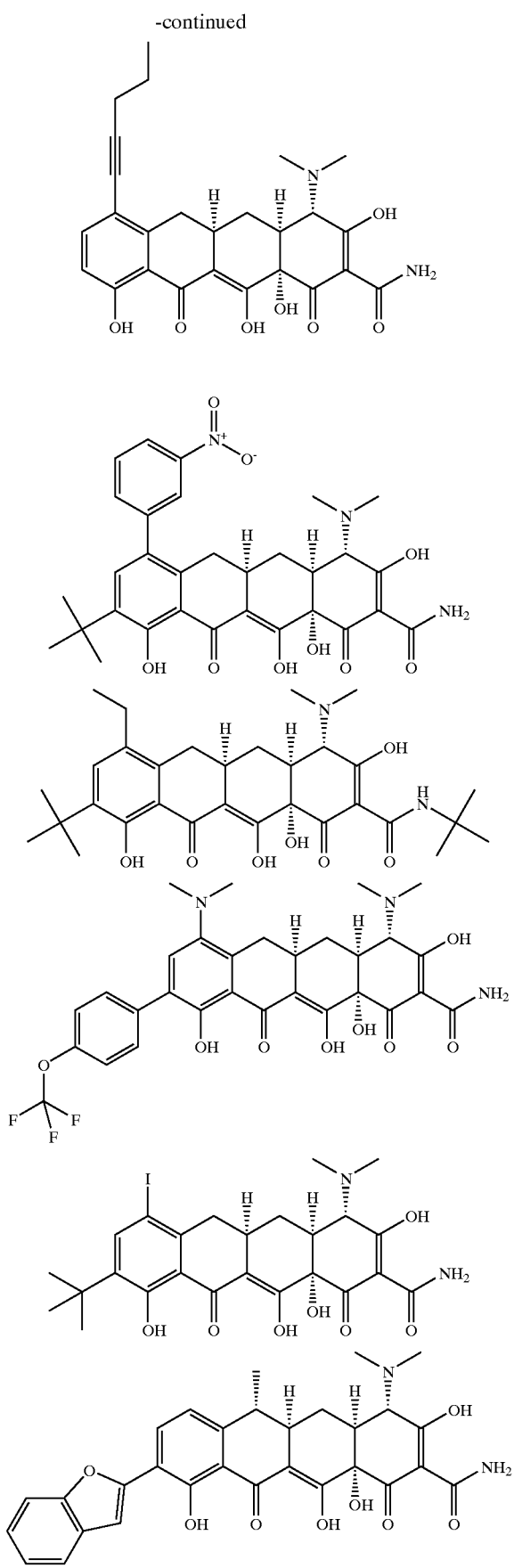

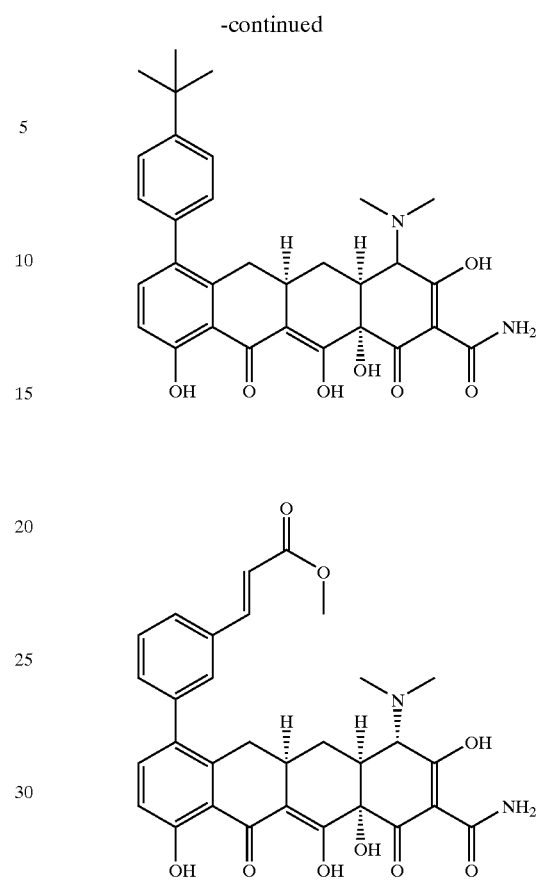

The substituted tetracycline compounds of the invention can be synthesized using the methods described in Example 1 and in the following schemes. Any novel tetracycline compounds described herein are included in the invention as compounds, in addition to methods of using them and pharmaceutical compositions containing them.

9-substituted tetracyclines such as 9-cyclopentenyl doxycycline can be synthesized by the method shown in Scheme 1. As in Scheme 1,9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate halogenated reagent (e.g., $R^9Br$, wherein $R^9$ is an aryl, alkenyl, or alkynyl moiety) to yield the desired compound (e.g., in Scheme 1,7-cyclopent-1-enyl doxycycline (1H) and 9-cyclopent-1-enyl doxycycline (1I)).

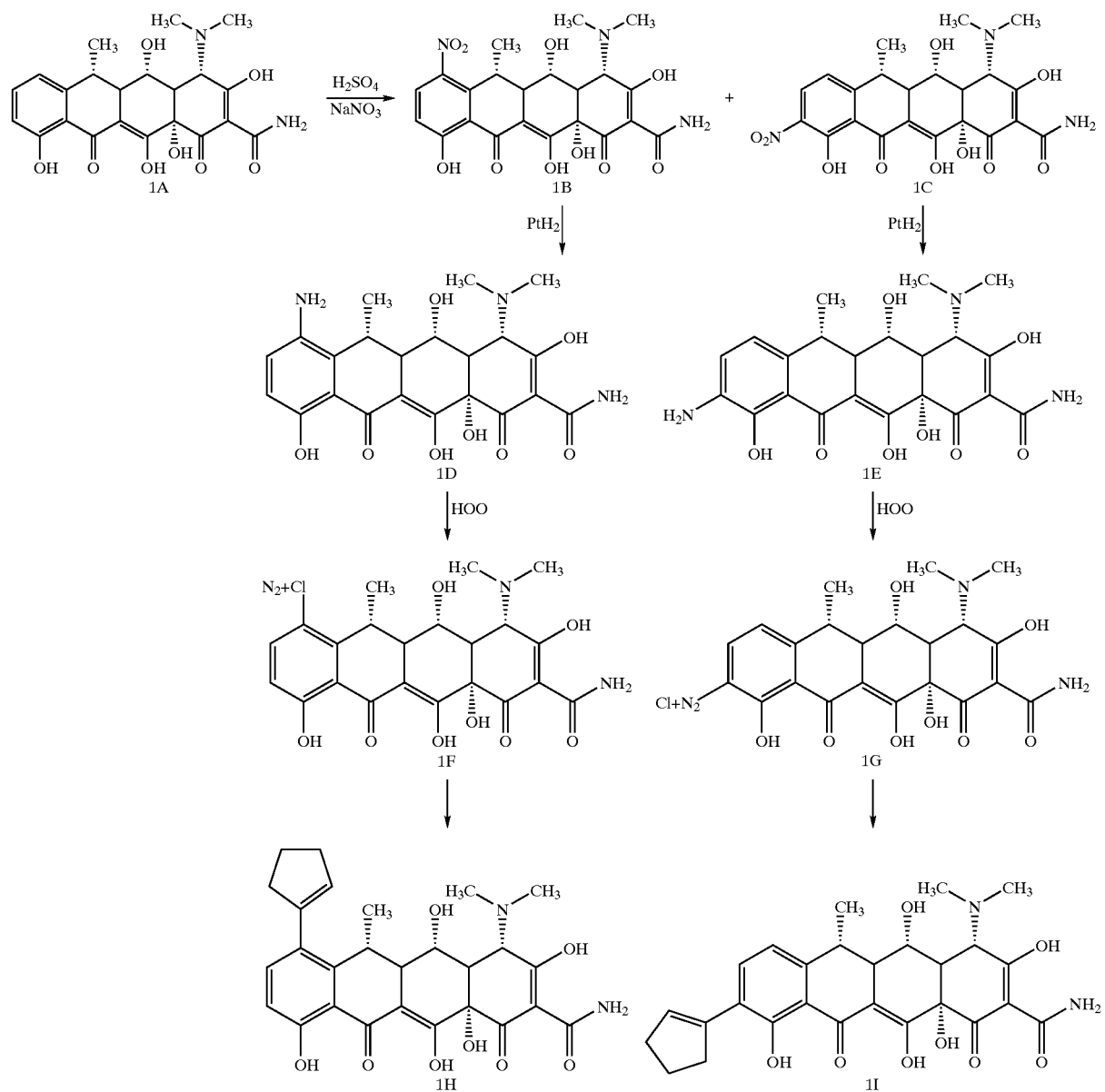
SCHEME 1
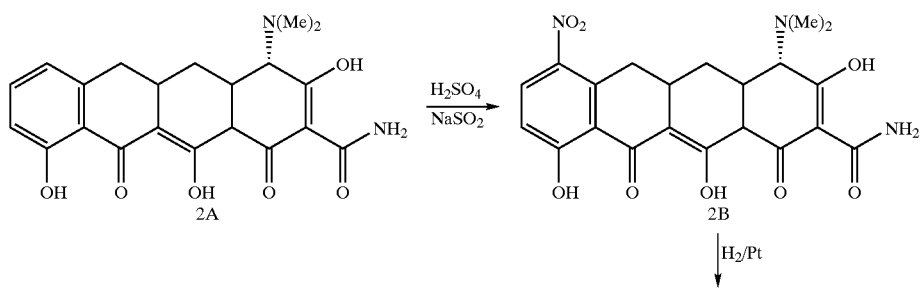
SCHEME 2

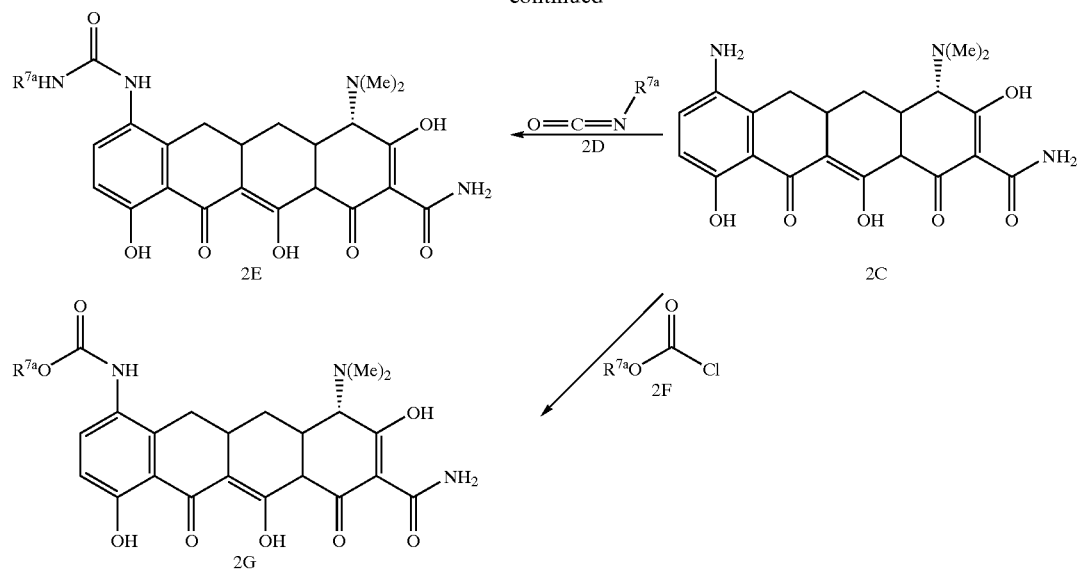

As shown in Scheme 2, tetracycline compounds of the invention wherein R is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

SCHEME 3

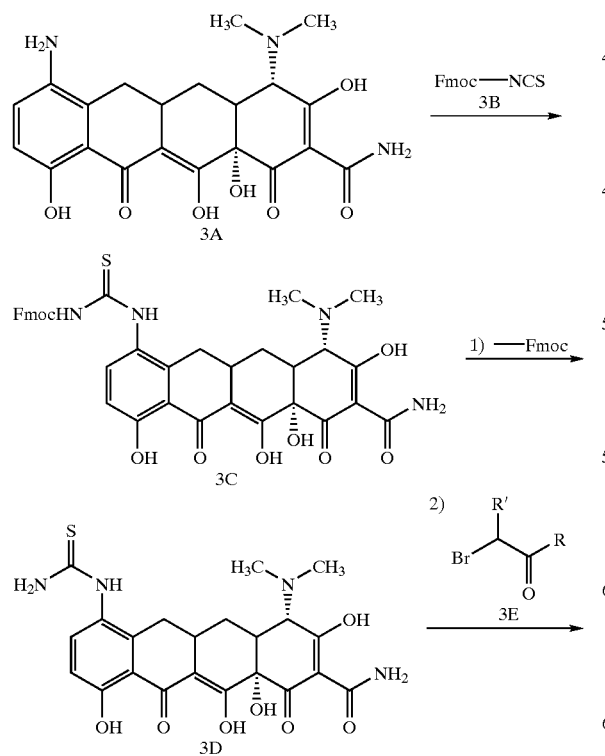

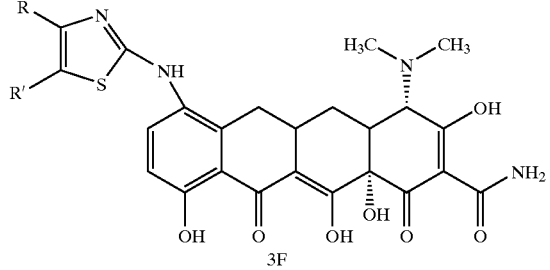

As shown in Scheme 3, tetracycline compounds of the invention, wherein $R^1$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

SCHEME 4

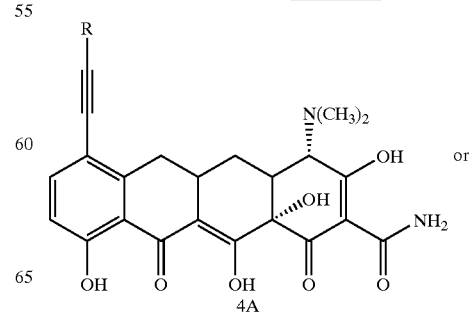

-continued

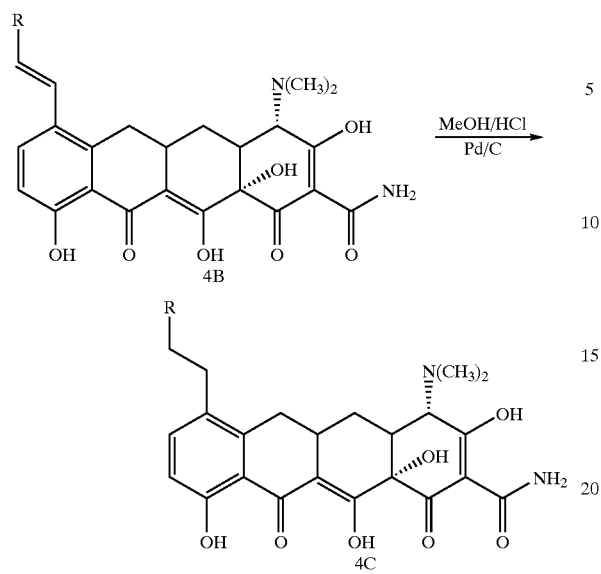

7-alkenyl tetracycline compounds, such as 7-alkynyl sancycline (4A) and 7-alkenyl sancycline (4B), can be hydrogenated to form alkyl 7-substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

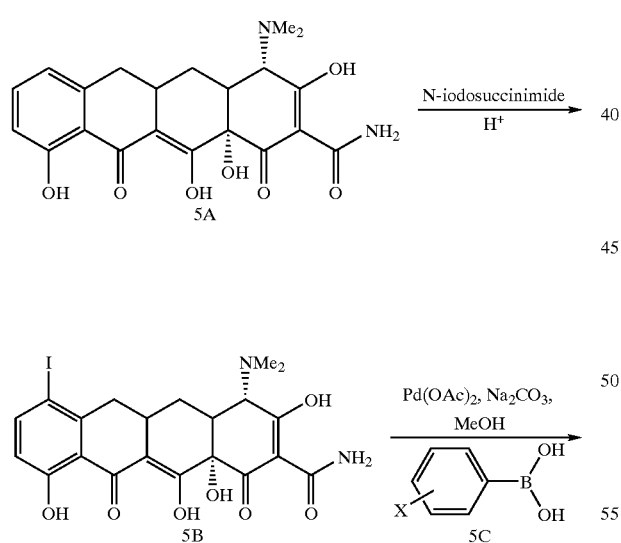

-continued

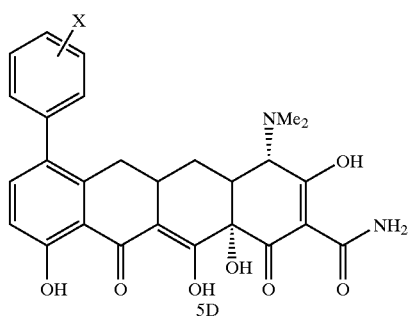

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (SB) is treated with an aqueous base (e.g., $Na_2CO_3$) and an appropriate boronic acid (SC) and under an inert atmosphere. The reaction is catalyzed with a palladium catalyst (e.g., $Pd(OAc)_2$). The product (5D) can be purified by methods known in the art (such as HPLC). Other 7-aryl and alkynyl tetracycline compounds can be synthesized using similar protocols.

The 7-substituted tetracycline compounds of the invention can also be synthesized using Stille cross couplings. Stille cross couplings can be performed using an appropriate tin reagent (e.g., R—$SnBu_3$) and a halogenated tetracycline compound, (e.g., 7-iodosancycline). The tin reagent and the iodosancycline compound can be treated with a palladium catalyst (e.g., $Pd(PPh_3)_2Cl_2$ or $Pd(AsPh_3)_2Cl_2$) and, optionally, with an additional copper salt, e.g., CuI. The resulting compound can then be purified using techniques known in the art.

SCHEME 6

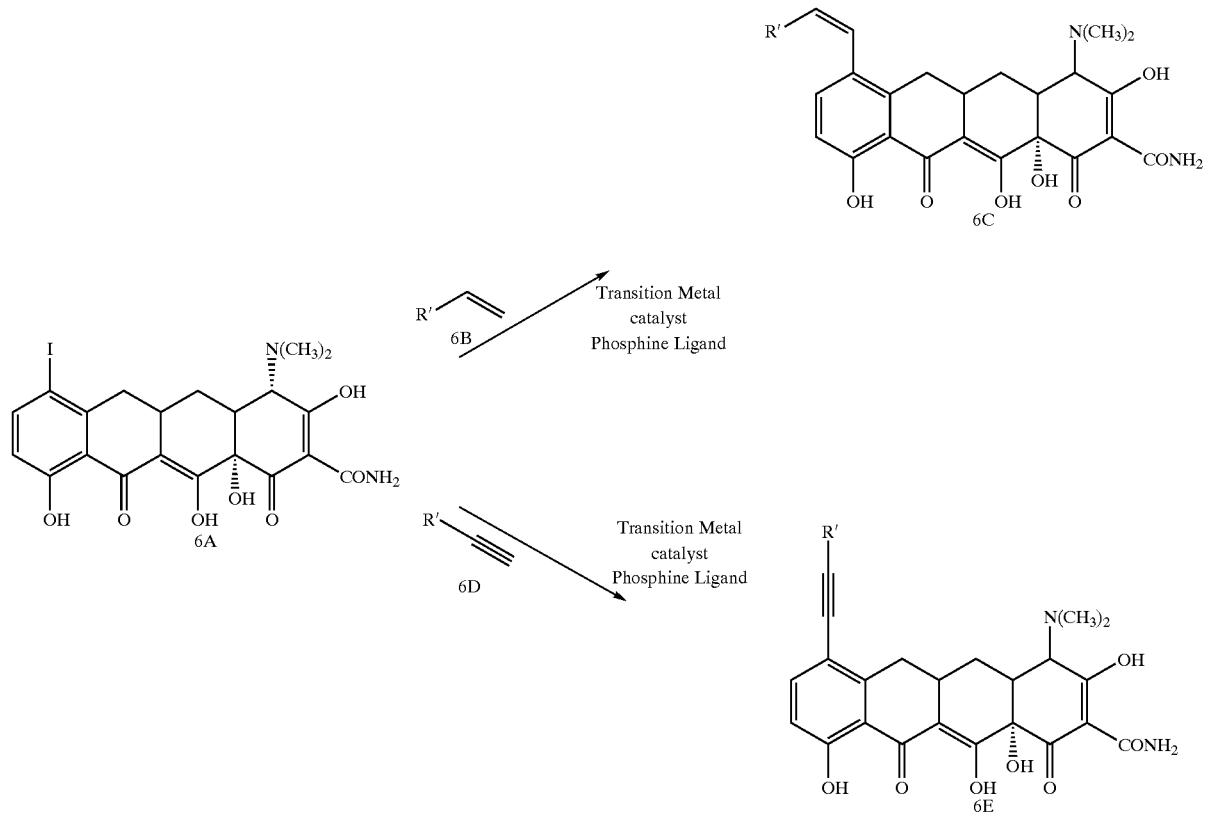

The compounds of the invention can also be synthesized using Heck-type cross coupling reactions. As shown in Scheme 6, Heck-type cross-couplings can be performed by suspending a halogenated tetracycline compound (e.g., 6-iodosancycline, 6A) and an appropriate palladium or other transition metal catalyst (e.g., Pd(OAc)$_2$ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art.

To prepare 7-(2'-Chloro-alkenyl)-tetracycline compounds, the following procedure can be used. 7-(alkynyl)-sancycline (7A) is dissolved in saturated methanol and hydrochloric acid and stirred. The solvent is then removed to yield the product (7B).

SCHEME 7

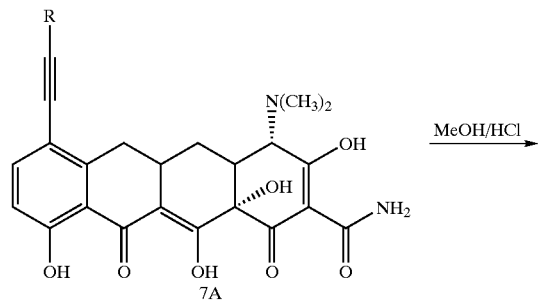

SCHEME 8

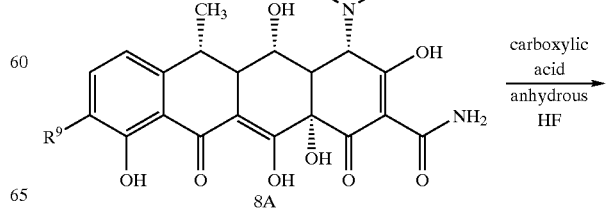

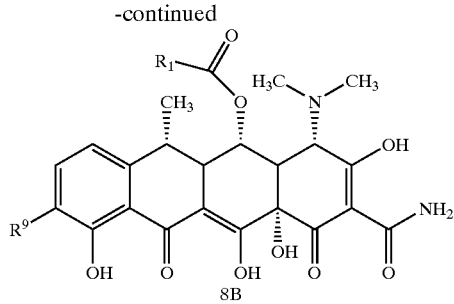

As depicted in Scheme 8,5-esters of 9-substituted tetracycline compounds can be formed by dissolving the 9-substituted compounds (8A) in strong acid (e.g. HF, methanesulphonic acid, and trifluoromethanesulfonic acid) and adding the appropriate carboxylic acid to yield the corresponding esters (8B).

As shown in Scheme 9 below, 7 and 9 aminomethyl tetracyclines may be synthesized using reagents such as hydroxymethyl-carbamic acid benzyl ester.

SCHEME 9

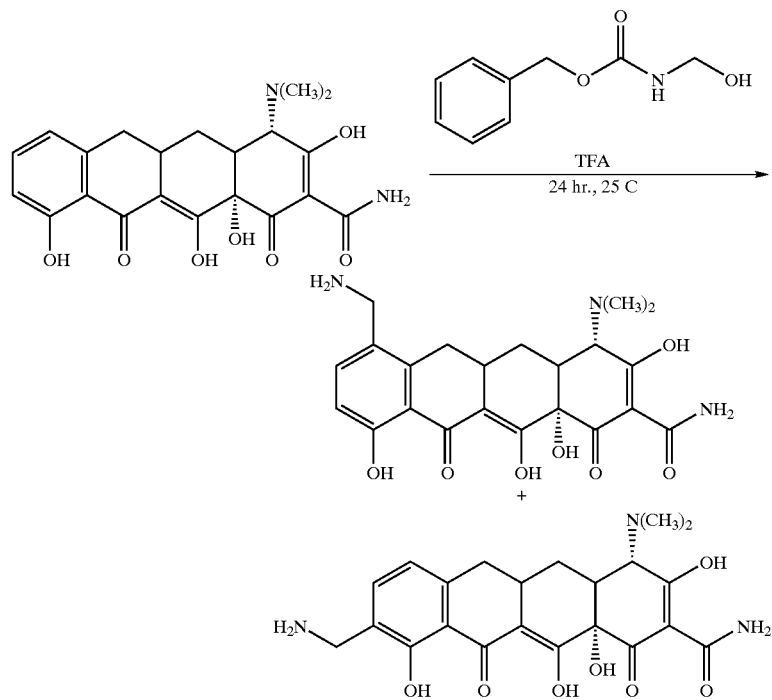

structure, and more preferably have 5 or 6 carbons in the ring structure, e.g., cyclopentene or cyclohexene.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkyls have from 4–7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, The term "alkenyl" includes unsaturated aliphatic groups, including straight-chain alkenyl groups, branched-chain alkenyl groups, cycloalkenyl (alicyclic) groups, alkenyl substituted cycloalkyl or cycloalkenyl groups, and cycloalkenyl substituted alkyl or alkenyl groups. The term alkenyl further includes alkenyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkenyl group has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkenyl groups have from 4–7 carbon atoms in their ring aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively. Examples of substituents of alkynyl groups include, for example alkyl, alkenyl (e.g., cycloalkenyl, e.g., cyclohenxenyl), and aryl groups.

Unless the number of carbons is otherwise specified, "lower alkyl" as used herein means an alkyl group, as defined above, but having from one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "alkylsulfinyl" include groups which have one or more sulfinyl (SO) linkages, typically 1 to about 5 or 6 sulfinyl linkages. Advantageous alkylsulfinyl groups include groups having 1 to about 12 carbon atoms, preferably from 1 to about 6 carbon atoms.

The term "alkylsulfonyl" includes groups which have one or more sulfonyl ($SO_2$) linkages, typically 1 to about 5 or 6 sulfonyl linkages. Advantageous alkylsulfonyl groups include groups having 1 to about 12 carbon atoms, preferably from 1 to about 6 carbon atoms.

The term "alkanoyl" includes groups having 1 to about 4 or 5 carbonyl groups. The term "aroyl" includes aryl groups, such as phenyl and other carbocyclic aryls, which have carbonyl substituents. The term "alkaroyl" includes aryl groups with alkylcarbonyl substituents, e.g., phenylacetyl.

The structures of some of the tetracycline compounds of this invention include asymmetric carbon atoms. The isomers arising from the chiral atoms (e.g., all enantiomers and diastereomers) are included within the scope of this invention, unless indicated otherwise. Such isomers can be obtained in substantially pure form by classical separation techniques and by stereochemically controlled synthesis.

The invention also pertains to methods of treating fungal associated disorders in a subject, by administering to the subject an effective amount of a substituted tetracycline compound such that the subject is treated. The substituted tetracycline compound may, in one embodiment, be a compound of formula (I) or any one of the compounds depicted in Table 2.

The language "effective amount" of the tetracycline compound is that amount necessary or sufficient to inhibit the growth of fungus or treat a fungus associated disorder, e.g., in an animal or in a plant, e.g., and prevent the various morphological and somatic symptoms of a fungal associated disorder. The effective amount can vary depending on such factors as the size and weight of the subject, the type of disorder, or the particular substituted tetracycline compound. For example, the choice of the substituted tetracycline compound can affect what constitutes an "effective amount". One of ordinary skill in the art would be able to study the aforementioned factors and make the determination regarding the effective amount of the substituted tetracycline compound without undue experimentation. An in vivo assay as described in Example 4 below or an assay similar thereto (e.g., differing in choice of cell line or type of illness) also can be used to determine an "effective amount" of a tetracycline compound. The ordinarily skilled artisan would select an appropriate amount of a tetracycline compound for use in the aforementioned in vivo assay. In an embodiment, the effective amount of the tetracycline is effective to treat a mammal suffering from a fungal associated disorder which is associated with a fungus from the genus Candida.

The term "subject" any organism which may benefit from the inhibition of a fungus or which is capable of having a fungal associated disorder. Examples of subjects include not only animals, such as mammals, birds, fish, etc., but plants which may be adversely effected by the presence of a fungus.

The term "mammal" includes, but is not limited to, ruminants (e.g., cattle and goats), mice, rats, hamsters, dogs, cats, horses, pigs, sheep, lions, tigers, bears, monkeys, chimpanzees, and, in a preferred embodiment, humans. The mammal may be immunocompetent or immunocompromised, e.g., suffering from an immunodeficiency. For example, the mammal may have AIDS or may have previously or concurrently undergone chemotherapy. In another embodiment, the mammal may be elderly or young. The mammal may or may not be suffering from a fungal associated disorder. The tetracycline compounds may be administered to a mammal susceptible to a fungal associated disorder to prevent the occurrence of the disorder.

The language "fungal associated disorder" includes disorders which are related to the presence of fungus in a subject. Examples of fungal associated disorders include both topical fungal infections caused by, e.g., Candida, and dermatophytes such as Trichophyton, Microsporum or Epidermophyton, or in mucosal infections caused by *Candida albicans* (e.g., oral thrush and vaginal candidiasis). The substituted tetracycline compounds of the invention are also useful for treatment of systemic fungal infections caused by, for example, *Candida albicans, Cryptococcus neoformans, Aspergillus flavus, Aspergillus fumigatus*, Coccidioides, Paracoccidioides, Histoplasma or Blastomyces. The substituted tetracycline compounds of the invention may be useful for treating fungal infections in immunocompromised patients such as patients with viral infections such as AIDS, CMV, and influenza, cancer patients receiving chemotherapy or radiotherapy, transplant patients receiving anti-rejection agents, and patients that have received toxic chemicals, metals and radiation exposure.

Examples of fungal associated disorders in animals include systemic infections, such as histoplasmosis, systemic candidiasis, aspergillosis, blastomycosis, coccidioidomycosis, paracoccidioidomycosis, and cryptococcosis, and superficial fungal disorders, such as dermatophyte (ringworm) infections, for example, tinea pedis (athlete's foot) and tinea cruris (jock itch), candidiasis, and actinomycosis. Another example of a fungal associated disorder include mycoses, which may be caused by fungi which are opportunists, rather than pathogens. Examples of fungi which may cause mycoses include candidiasis, aspergillosis, phycomycosis, nocardiosis, and cryptococcosis.

Other fungal associated disorders include aspergillosis, candidosis, chromomycosis, coccidioidiocycosis, cryptococcocosis, entomophthoromycosis, epizootic lymphangitis, geotrichosis, histoplasmosis, mucormycosis, mycetoma, north american blastomycosis, oomycosis, paecilimycosis, penicilliosis, rhinosporidiosis, and sprotrichiosis in animals. In an embodiment, the substituted tetracycline compounds of the invention can be included in feed for the livestock, such that normal consumption of said feed provides about 1 mg to about 200 mg of at least one of the substituted tetracycline compounds of the invention per kg of animal per day.

The invention also pertains to a pharmaceutical composition containing an effective amount of a tetracycline compound to treat or prevent a fungal associated disorder in a subject, e.g., a mammal, and a pharmaceutically acceptable carrier. The tetracycline compound may be a substituted tetracycline, a compound of formula (I), or a compound depicted in Table 2.

The language "pharmaceutically acceptable carrier" includes substances capable of being coadministered with the substituted tetracycline compound(s), and which allows the substituted tetracycline compounds to perform their intended function, e.g., treating a fungal associated state or preventing a fungal associated disorder. Examples of such carriers include solutions, solvents, dispersion media, delay agents, emulsions and the like. The use of such media for pharmaceutically active substances are well known in the art. Any other conventional carrier suitable for use with the tetracycline compounds of the present invention are included.

For example, one or more substituted tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

At least many of the substituted tetracycline compounds of the invention suitably may be administered to a subject in a protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an appropriate acidic group is present on a compound of the invention, a pharmaceutically acceptable salt of an organic or inorganic base can be employed such as an ammonium salt, or salt of an organic amine, or a salt of an alkali metal or alkaline earth metal such as a potassium, calcium or sodium salt.

Therapeutic compounds can be administered to a subject in accordance with the invention by any of a variety of routes. Topical (including transdermal, buccal or sublingual), oral, and parenteral (including intraperitoneal, subcutaneous, intravenous, intradermal or intramuscular injection) are generally preferred.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The tetracycline compounds may also be formulated such that the compound is released over an extended period of time.

For parenteral application, particularly suitable are solutions, preferably oily or aqueous solutions as well as suspensions, emulsions, or implants, including suppositories. Substituted tetracycline compounds may be formulated in sterile form in multiple or single dose formats such as being dispersed in a fluid carrier such as sterile physiological saline or 5% saline dextrose solutions commonly used with injectables.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For topical applications, the substituted tetracycline compound(s) can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

The actual preferred amounts of active substituted tetracycline compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

In a still further aspect, the substituted tetracycline compounds of the present invention (e.g., substituted tetracycline compounds, e.g., compounds of formula (I), or compounds shown in Table 2) can also be advantageously used in agricultural compositions, for example, compositions for plants and seeds to treat or prevent a variety of plant pathogenic fungi, including rusts, mildews, and molds. Generally, the compounds of the present invention are dispensed in the form of dusting powders, granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture, and they are manufactured in accordance with conventional procedures. The compositions typically contain from 0.01 to 10 wt %, preferably 0.1 to 1 wt. % of the active ingredient. The compositions may also incorporate other active ingredients, for example, compounds having herbicidal or insecticidal activity or a further fungicide. The compounds and compositions can be applied in a number of ways, for example, they can be applied directly to the plant foliage, stems, branches, seeds or roots or to the soil or other growing medium and they may be used not only to eradicate disease, but also prophylactically to protect the plants or seeds from attack. For field use, likely application rates of active ingredient are about 100 to 10,000 g/acre. The substituted tetracycline compounds of the invention can also be formulated for use in cleaning supplies, e.g., to prevent a growth of a fungus, or to kill or stop the growth of a fungus The present invention is further illustrated by the following examples. These examples are provided to aid in the understanding of the invention and are not to be construed as limitations thereof.

EXEMPLIFICATION OF THE INVENTION

EXAMPLE 1

Synthesis of Tetracycline Compounds

The following example discusses methods of synthesizing the substituted tetracycline compounds of the invention. One of ordinary skill in the art will be able to use the presented examples and/or art recognized techniques to synthesize the compounds of the invention.

Experimental

Melting points were taken on a Mel-Temp capillary melting point apparatus and are uncorrected. Nuclear magnetic resonance ($^1$H NMR) spectra were recorded at 300 MHz on a Bruker Avance spectrometer. The chemical shift values are expressed in $\delta$ values (ppm) relative to tetramethylsilane or 3-(trimethylsilyl)-1-propanesulfonic acid, sodium salt, as either an internal or external standard using $CDCl_3$, DMSO-$d_6$, or MeOH-$d_4$ as the solvent. Column chromatography was performed according to the method of Still using Baker "flash" grade silica gel (40 $\mu$m) that was treated with a saturated solution of $Na_2$EDTA, washed with water, filtered and dried in an oven at 130° C. for three hours prior to use. Analytical TLC separations employed the use of 0.25 mm silica gel plates with florescence indicator obtained from J. T. Baker Chemical Co., Phillipsburg, N.J., that were pretreated by immersion into a saturated solution of $Na_2$EDTA for five minutes and reactivated at 130° C. for three hours. Solvent systems used were as follows: 50:50:5 $CHCl_3$/MeOH/5% $Na_2$EDTA (lower phase) (I), 65:20:5, $CHCl_3$/MeOH/$Na_2$EDTA (lower phase) (II). Visualization of TLC was accomplished by 0.5% aqueous Fast Blue BB salt and heating at 130° C. for 5 minutes. Analytical HPLC was performed on a Waters Bondapak C18 reverse phase column by using two Varian SD 100 HPLC pumps at a 1.6 mL/min flow rate controlled by software. Detection was by UV absorption with Model 441 absorbance detector operating at 280 um. Mobile phases used followed a linear gradient from 30% to 100% methanol over 30 minutes at 1.6 mL/min flow rate followed by isocratic elution with MeOH; solvent system A: 0.02 M $Na_2HPO_4$+0.001 M $Na_2$EDTA adjusted to pH 4.5 with $H_3PO_3$; solvent system B: 100% MeOH. Semipreparative HPLC separations used a Waters semipreparative C 18 reverse-phase column at a flow rate of 6.4 mL/min. Low and high resolution mass spectra were performed on a PE Mariner spectrometer (Nelson et al., *J. Med. Chem.* (1993) 36(3):374).

7 Iodo Sancycline

One gram of sancycline was dissolved in 25 mL of TFA (trifluoroacetic acid) that was cooled to 0° C. (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was the added slowly to a rapidly stirring solution of diethyl ether to form a greenish brown precipitate. The 7-iodo isomer of sancycline was purified by treating the 7-iodo product with activated charcoal, filtering through Celite, and subsequent removal of the solvent in vacuo to produce the 7-isomer compound as a pure yellow solid in 75% yield.

MS(M+H) (formic acid solvent) 541.3.

\Rt: Hypersil C18 BDS Column, 11.73

$^1$H NMR (Methanol $d_{4-300}$ MHz) δ 7.87–7.90 (d, 1H), 6.66–6.69 (d, 1H), 4.06 (s, 1H), 2.98 (s, 6H), 2.42 (m, 1H), 2.19 (m, 1H), 1.62 (m, 4H), 0.99 (m, 2H)

7-(2',5' Dimethyl-Phenyl Sancycline 7-iodosancycline (0.28 mM), Pd(OAc)$_2$ and 10 mL of MeOH are added to a flask with a stir bar and the system degassed 3× using argon. Na$_2$CO$_3$ (0.8 mM) dissolved in water and argon degassed is added via syringe is added along with 2,5-dimethylphenyl boronic acid (0.55 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using C18 reverse-phase silica. The solvent was removed in vacuo to yield the product plus salts. The salts were removed by extraction into 50:25:25 water, butanol, ethyl acetate and dried in vacuo. This solid was dissolved in MeOH and the HCl salt made by bubbling in HCl gas.

7-(Hexynyl)-Sancycline

7-I-Sancycline (1 gm, 1.86 mmol), taken in 25 mL of acetonitrile was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen for few minutes. 1-Hexyne (3.72 mmol) and triethylamine (1 mL) were added to the suspension. It was turned into a brown solution upon addition of Et$_3$N. The reaction mixture was then heated to 70° C. for 3 hours. Progress of the reaction was monitored by HPLC. It was then cooled down to room temperature and was filtered through celite. Evaporation of the solvent gave a brown solid, which was then purified on preparative HPLC to give a yellow solid. The structure of this compound has been characterized using 1H NMR, HPLC, and MS.

9-(4'-Fluorophenylethyl)-Minocycline 9-(4-Fluorophenylethynyl)-minocycline (1 mmol) was taken in saturated solution of MeOH/HCl. To this solution 10% Pd/C was added and was subjected to hydrogenation at 50 psi for 12 hrs. It was then filtered through celite. The solvent was evaporated to give a yellow powder. Finally, it was precipitated from MeOH/diethylether. The structure of this compound has been characterized using 1H NMR, HPLC, and MS.

9-(2',5'-Dimethylphenyl) Minocycline

In a clean, dry reaction vessel, was placed 9-iodominocycline (0.762 mmoles) bis HCl salt, palladium (II) acetate (0.076 mmoles) along with 10 ml of reagent grade methanol. The solution was immediately purged, with stirring, with a stream of argon gas for approximately 5 minutes. The reaction vessel was brought to reflux and to it was sequentially added via syringe 2M potassium carbonate solution, followed by a solution of 2,5-dimethylphenyl boronic acid (1.53 mmoles) in 5 ml of reagent DMF. Both of these solutions were previously degassed with argon gas for approximately 5 minutes. The reaction was heated for 45 minutes, the progress was monitored via reverse phase HPLC. The reaction was suctioned filtered through a pad of diatomaceous earth and washed the pad with DMF. The filtrates were reduced to an oil under vacuum and residue treated with t-butylmethyl ether. Crude material was purified via reverse phase HPLC on DVB utilizing a gradient of water and methanol/acetonitrile containing 1.0% trifluoroacetic acid.

EXAMPLE 2

Antifungal Activity of Substituted Tetracycline Compounds

Antifungal activity of the tetracyclines was determined by a broth microdillution technique following NCCLS (1997) Standards. Assays were setup using a Tecan Genesis robotic workstation. All drugs were dissolved in 10% DMSO. Drug concentration ranged from 0.125 to 64 µg/mL in 2 fold serial dilutions. Each tetracycline was tested at 10 concentrations ranging from 0.125 to 64 µg/mL. The compounds were tested for their antifungal activity against *Candida albicans* (ATCC#90028). The final concentration of DMSO was kept below 1%. Checkerboard analysis of the initial hits will be performed to better determine the activity of the compound.

The strains tested include those listed in Table 1.

TABLE 1

| Genus | Species | ATCC/FGSC # |
| --- | --- | --- |
| Aspergillus | fumigatus | ATCC 13073 (Fresenius) |
| Aspergillus | nidulans | FGSCA991 (wt) |
| Candida | albicans | ATCC90028 |
| Candida | albicans | PCI-1 |
| Candida | albicans | PCI-17 |
| Candida | albicans | ATCC 36082 |
| Candida | glabrata | ATCC 90030 |
| Candida | guilliermondii | ATCC 14242 |
| Candida | krusei | ATCC 96685 |
| Candida | krusei | ATCC 90878 |
| Candida | lusitaniae | ATCC 24347 |
| Candida | parapsilosis | ATCC 22109 |
| Candida | tropicalis | ATCC 14246 |
| Candida | tropicalis | ATCC 28707 |
| Cryptococcus | neoformans | ATCC 90012 |
| Cryptococcus | neoformans | ATCC 90013 |
| Issatchenkia | orientalis | ATCC 6258 |
| Neurospora | crassa | FGSC853 |

The results are shown in Table 2. For each compound, * represents good antifungal activity against the particular fungus,  represents very good inhibition of the fungus, and * represents excellent inhibition of a particular fungus.

TABLE 2

| ID | STRUCTURE | Aspergillus flavus | Aspergillus fumigatus | Aspergillus terreus | C. dubliniensis | Candida albicans | Candida glabrata | Candida bulliermondii |
| --- | --- | --- | --- | --- | --- | --- | --- | --- |

TABLE 2-continued
| | | |
|---|---|---|
| A | 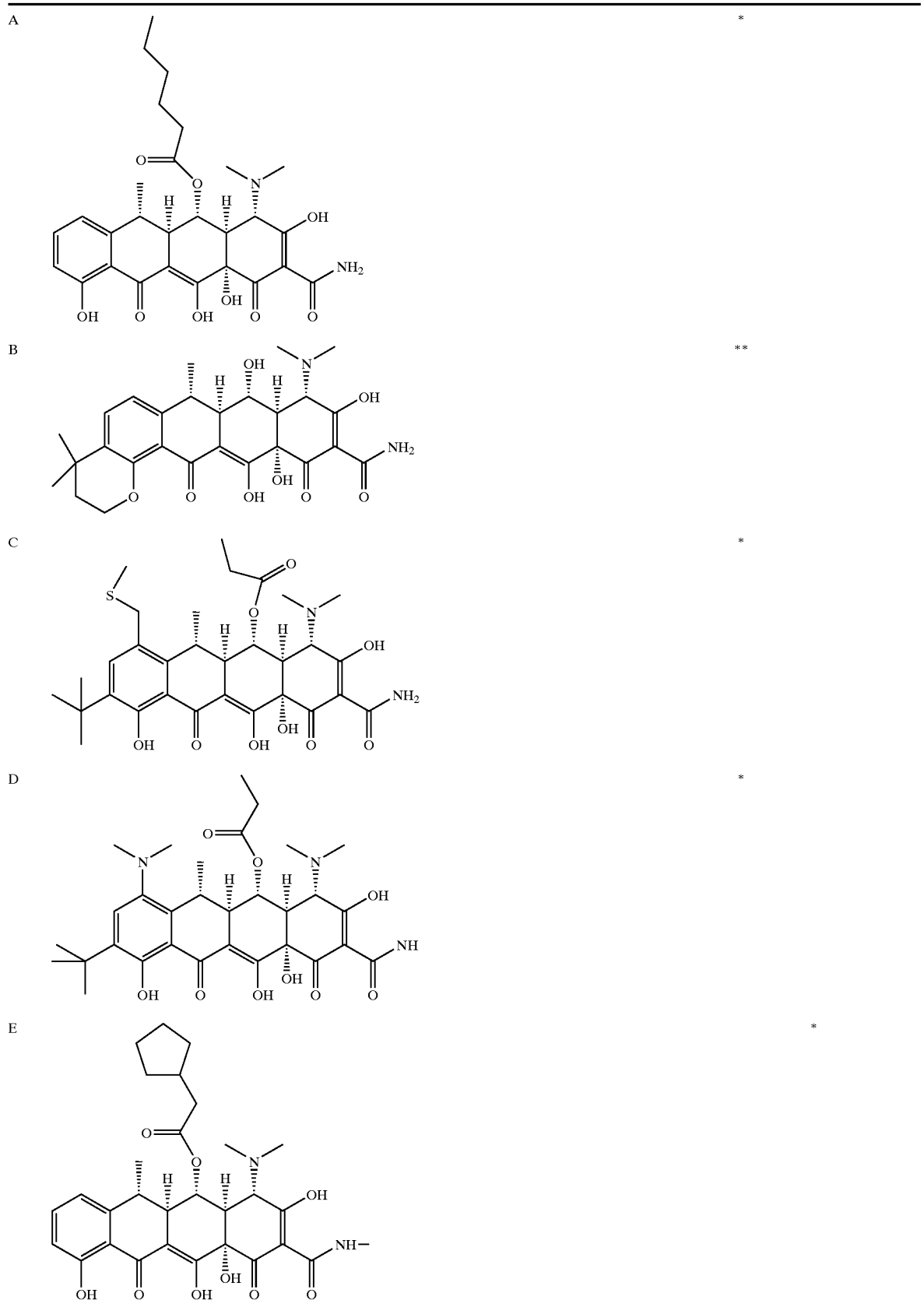 | * |
| B | | ** |
| C | | * |
| D | | * |
| E | | * |

TABLE 2-continued
| | | | | |
|---|---|---|---|---|
| F 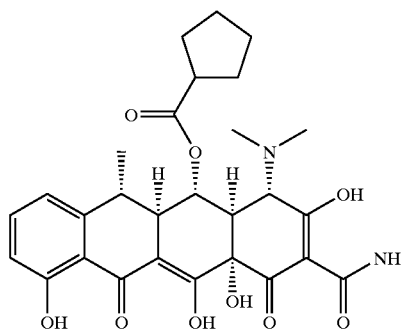 | ** | | | |
| G 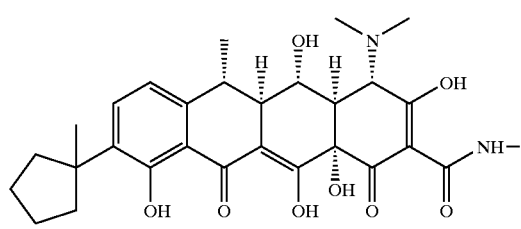 |  |  | *** | |
| H 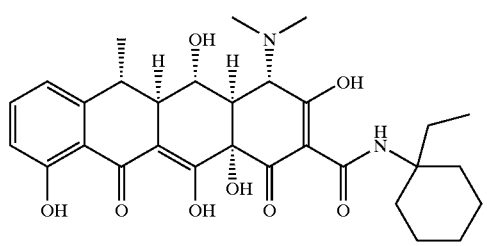 | ** | | | |
| I 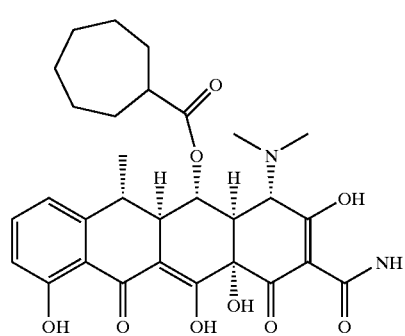 | ** | | | |
| J 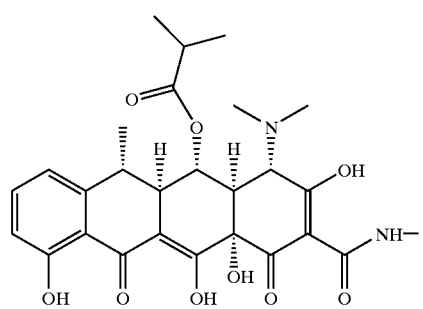 | * | | | |

TABLE 2-continued
| | | |
|---|---|---|
| K | 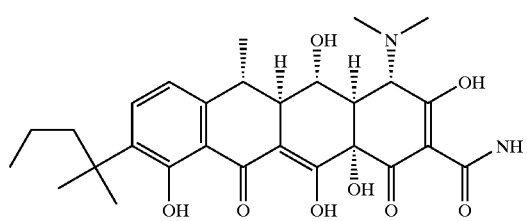 | ** |
| L | 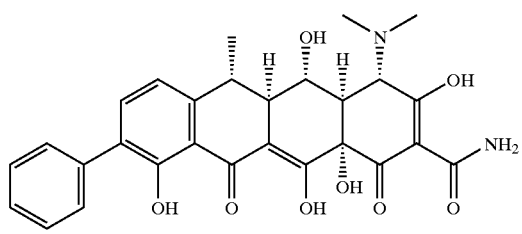 | * |
| M | 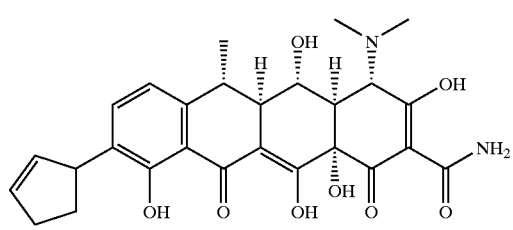 | ** |
| N | 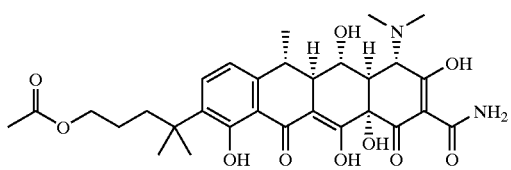 | ** |
| O | 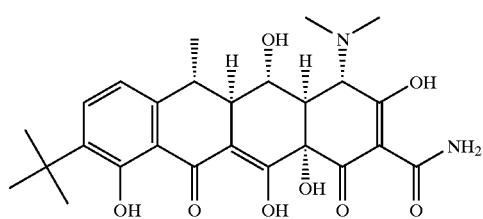 | ** |
| P | 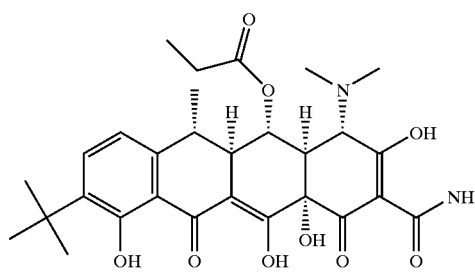 | * |
| Q | 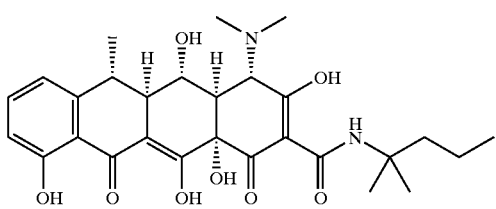 | |

TABLE 2-continued

| | | |
|---|---|---|
| R | [structure] | ** |
| S | [structure] | ** |
| T | [structure] | ** |
| U | [structure] | * |
| V | [structure] | ** |
| W | [structure] | * |

TABLE 2-continued
| | | |
|---|---|---|
| X | 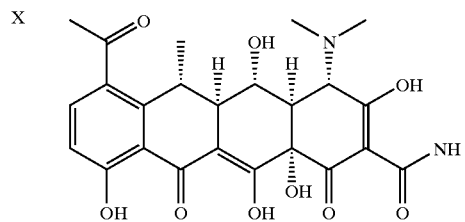 | * |
| Y | 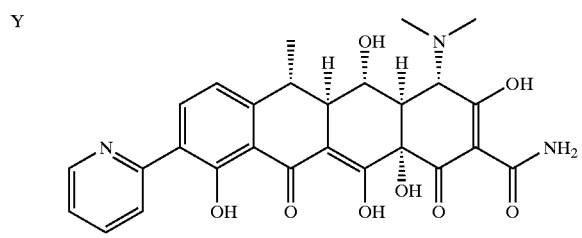 | *** |
| Z | 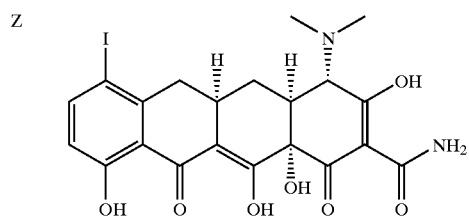 | * |
| AA | 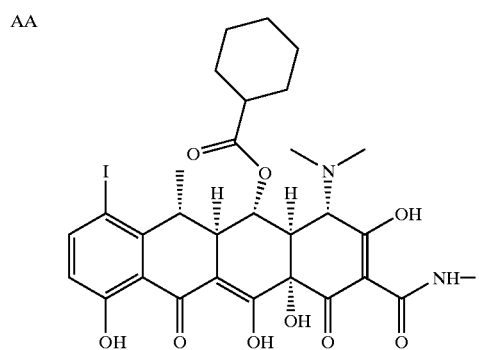 | * |
| AB | 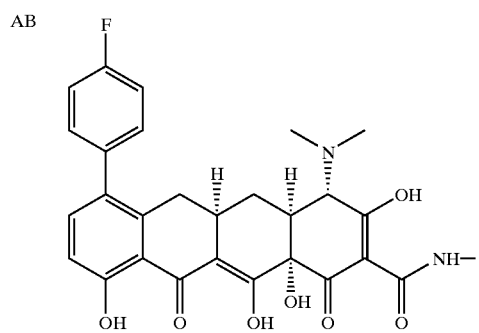 | ** |

TABLE 2-continued

| | Structure | |
|---|---|---|
| AC | 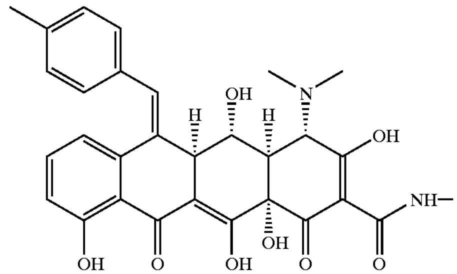 | * |
| AD | 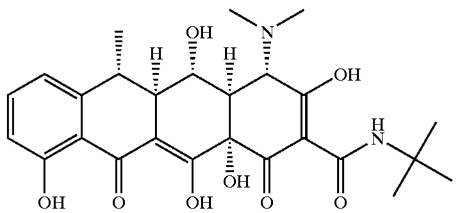 | ** |
| AE | 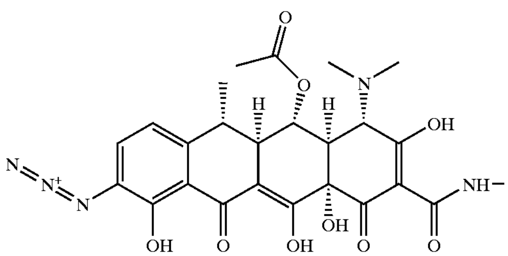 | *** |
| AF | 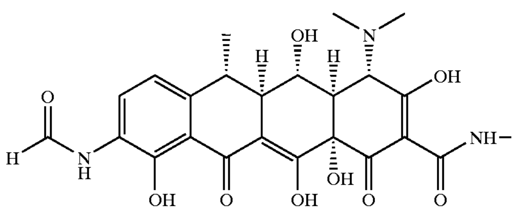 | ** |
| AG | 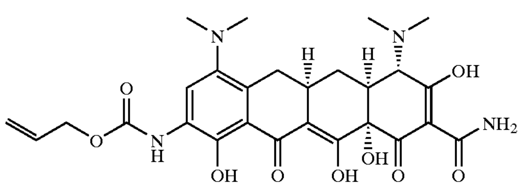 | * |
| AH | 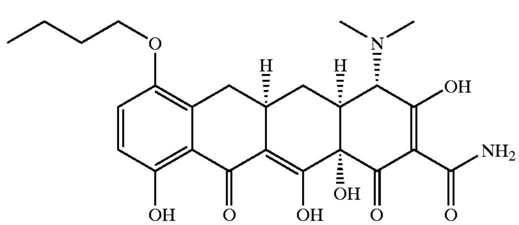 | *** |
| AI | 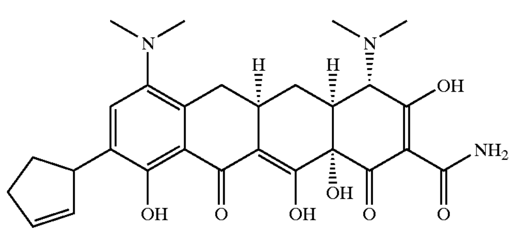 | * |

TABLE 2-continued
| | | |
|---|---|---|
| AJ | 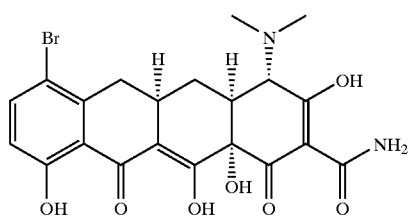 | ** |
| AK | 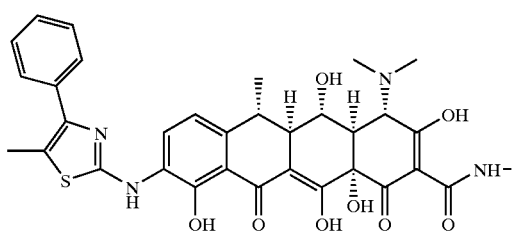 | * |
| AL | 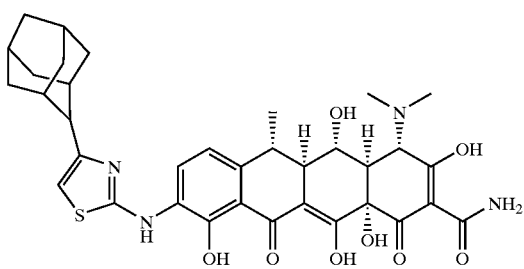 | * |
| AM | 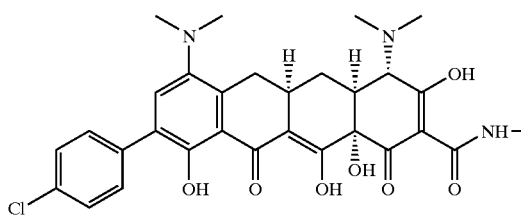 | ** |
| AN | 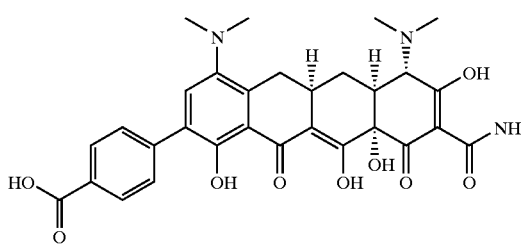 | ** |
| AO | 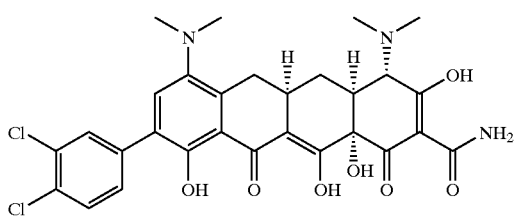 | * |

TABLE 2-continued

| | | | |
|---|---|---|---|
| AP | [structure] | * | |
| AQ | [structure] | ** | |
| AR | [structure] | ** | ** |
| AS | [structure] | ** | |
| AT | [structure] | ** | |

TABLE 2-continued

| | | | | | | |
|---|---|---|---|---|---|---|
| AU | | * | | | | |
| AV | | | | | | |
| AW | | ** | | ** | ** | *** |
| AX | | ** | | | | |
| AY | | ** | | | | |

TABLE 2-continued

| | | | |
|---|---|---|---|
| AZ | (structure) | | ** |
| BA | (structure) | * | ** |
| BB | (structure) | ** | ** |
| BC | (structure) | | ** |
| BD | (structure) | | ** |

TABLE 2-continued
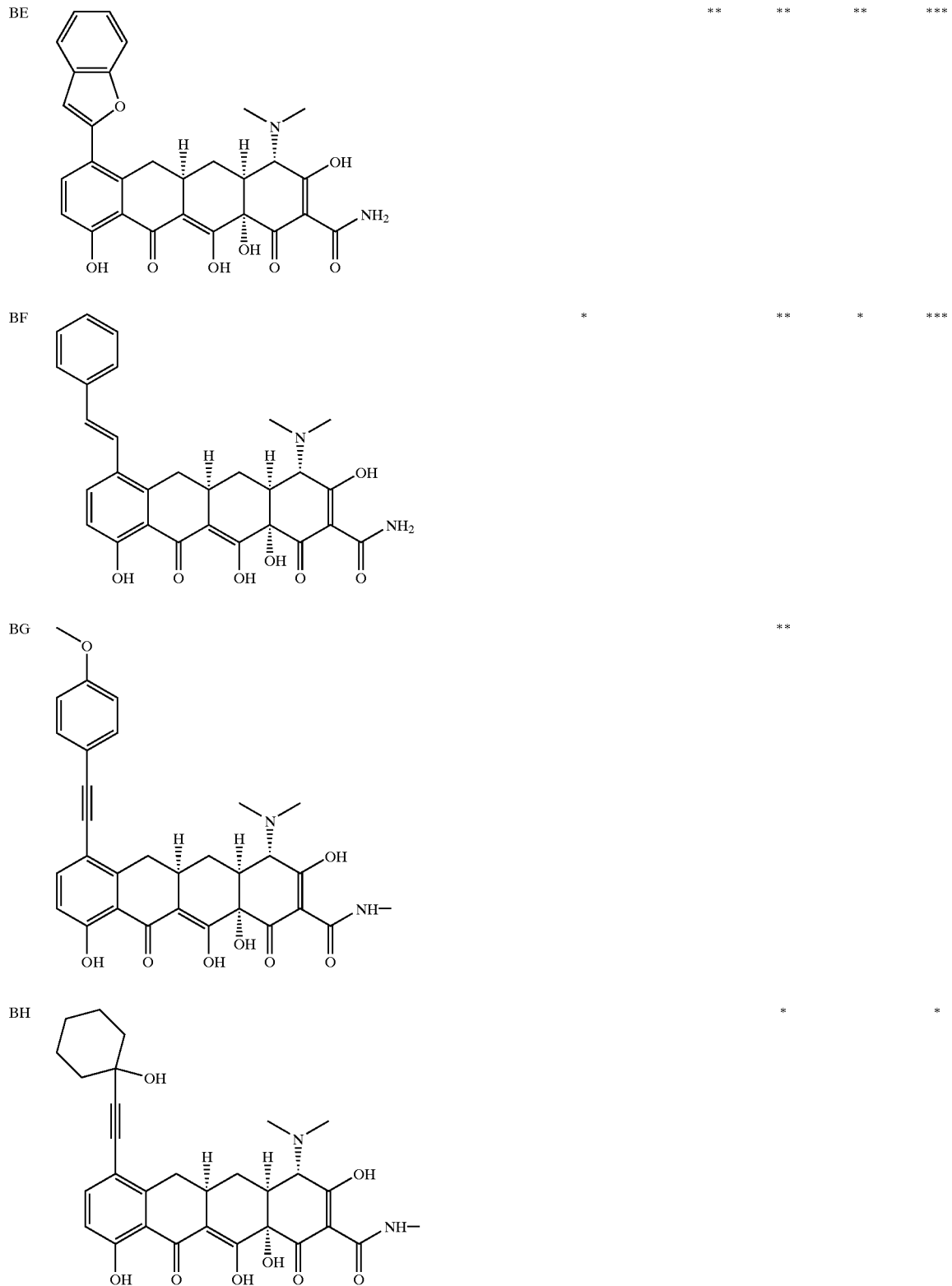

TABLE 2-continued

| | | | | |
|---|---|---|---|---|
| BI | (structure) | ** ** | * | ** |
| BJ | (structure) | ** | | |
| BK | (structure) | ** | | |
| BL | (structure) | ** | ** | |

TABLE 2-continued
| | | | |
|---|---|---|---|
| BM | 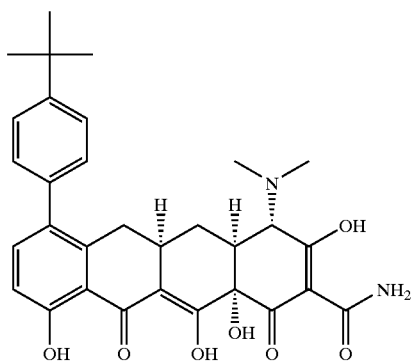 | ** | |
| BN | 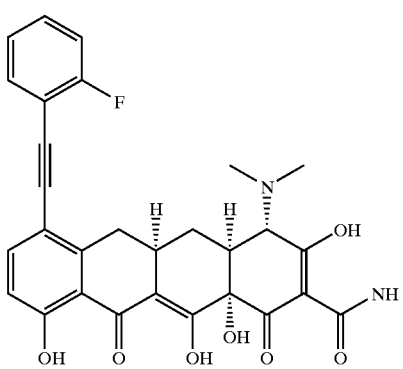 |  |  |
| BO | 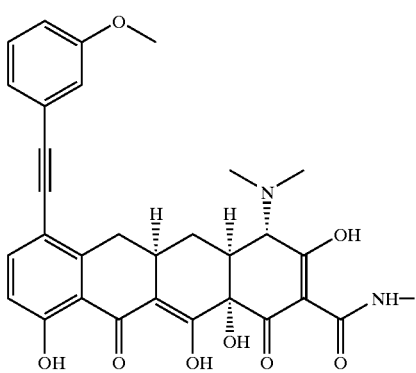 | * | |
| BP | 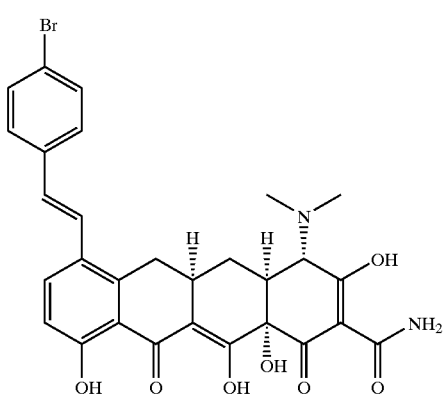 | ** | |

TABLE 2-continued
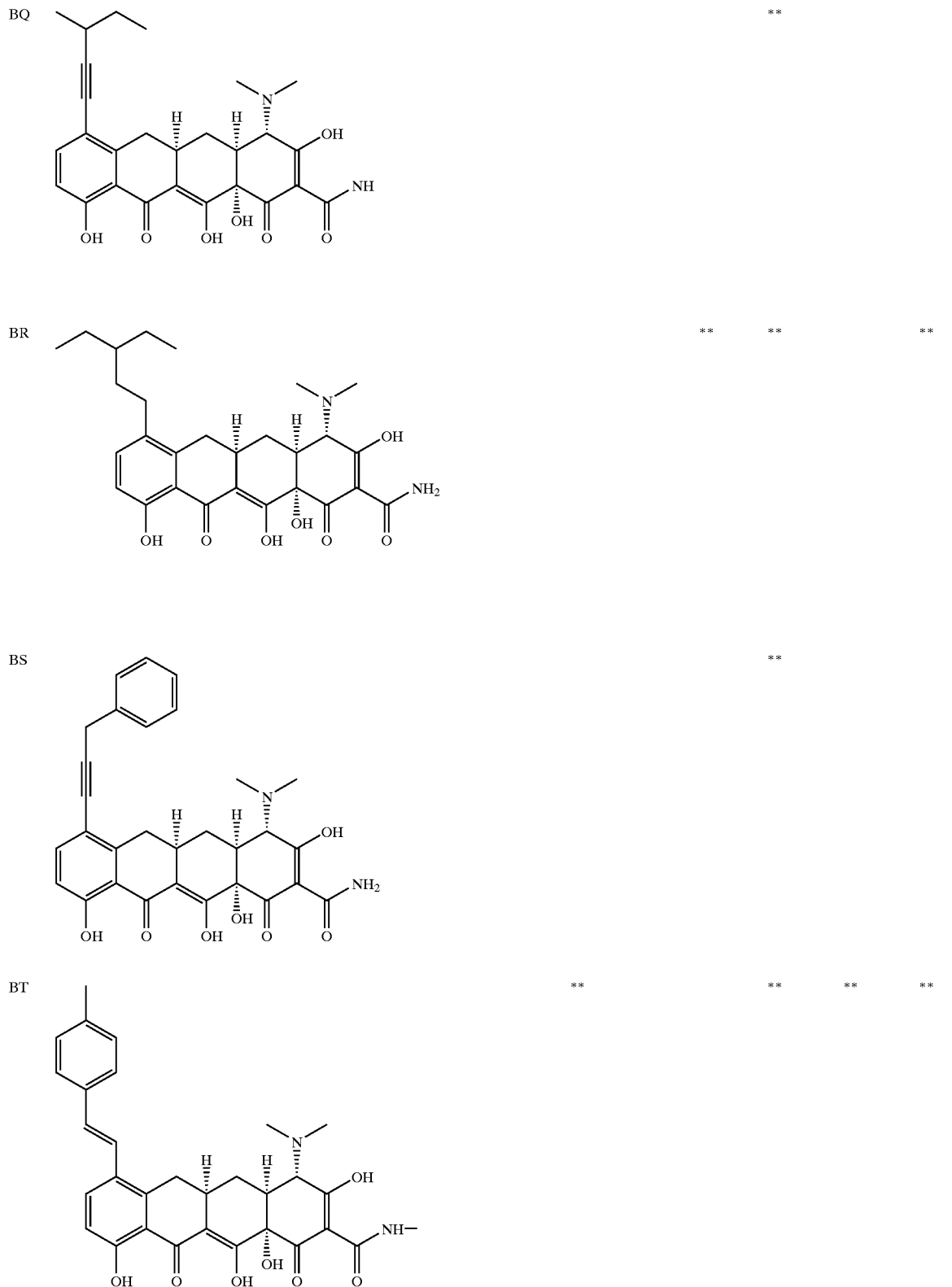

TABLE 2-continued
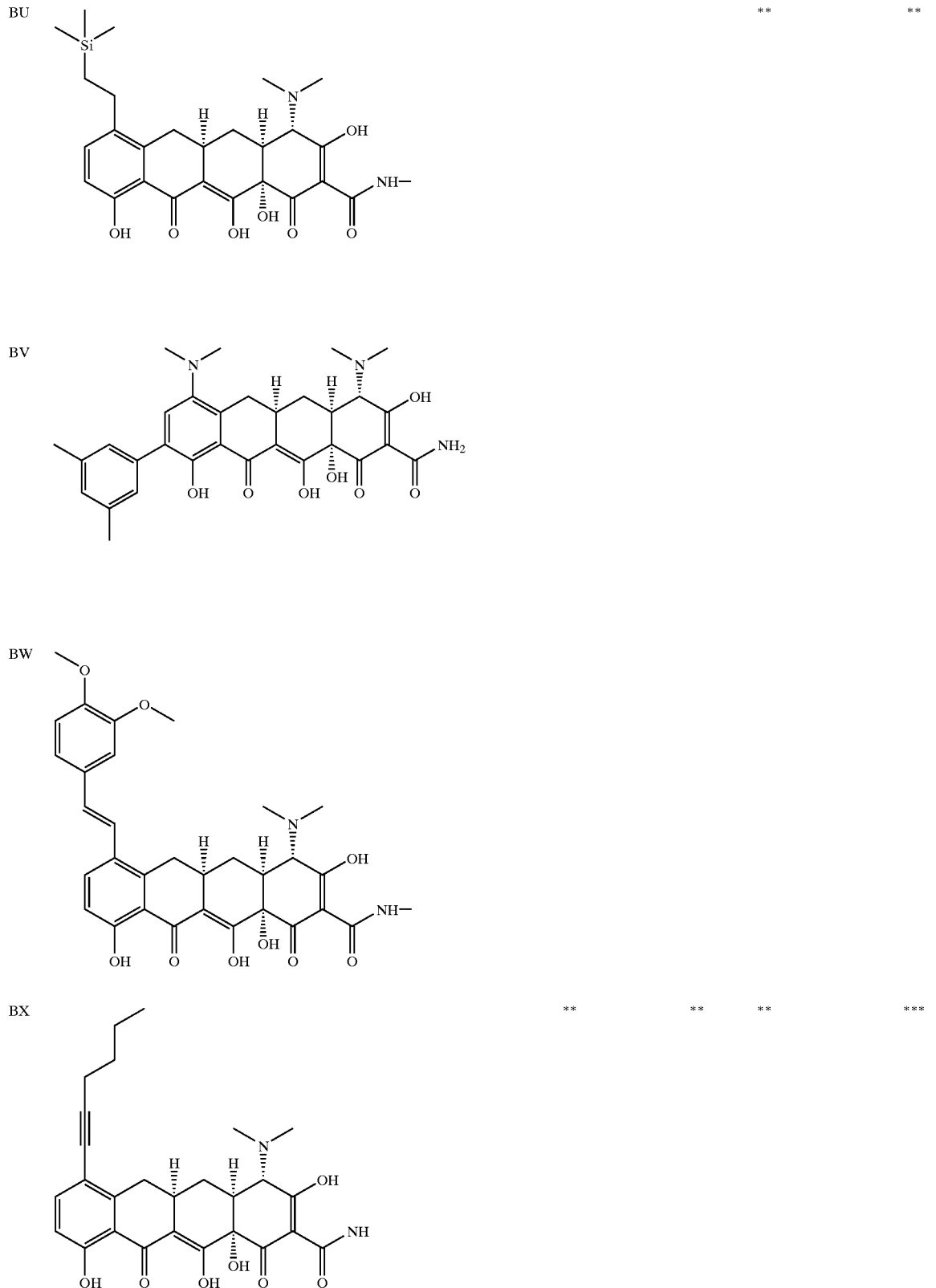

TABLE 2-continued

| | | * | ** |
|---|---|---|---|
| BY | (structure) | * | ** |
| BZ | (structure) | * | |
| CA | (structure) | * | |
| CB | (structure) | | ** |
| CC | (structure) | ** | ** |

TABLE 2-continued

| | | | | |
|---|---|---|---|---|
| CD | | | | |
| CE | | ** | ** | ** |
| CF | | | ** | |
| CG | | | ** | |
| CH | | ** | * | ** |

TABLE 2-continued

| | Structure | | | | |
|---|---|---|---|---|---|
| CI | (structure) | * | | | |
| CJ | (structure) | ** | *** | ** | ** |
| CK | (structure) | * | | | |
| CL | (structure) | * | ** | ** | |
| CM | (structure) | ** | * | | |
| CN | (structure) | * | | | |
| CO | (structure) | ** | | | |

TABLE 2-continued

| | | |
|---|---|---|
| CP | [structure] | |
| CQ | [structure] | * * |
| CR | [structure] | *** |
| CS | [structure] | * |
| CT | [structure] | * |
| CU | [structure] | * |
| CV | [structure] | *** |

TABLE 2-continued
CW 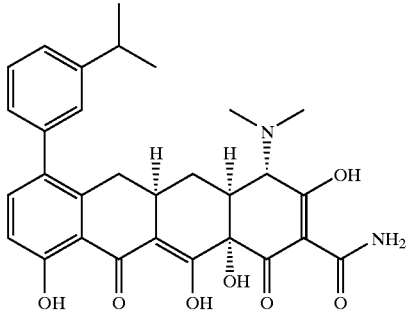 **
CX 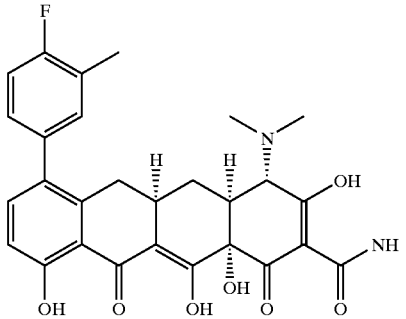 **
CY 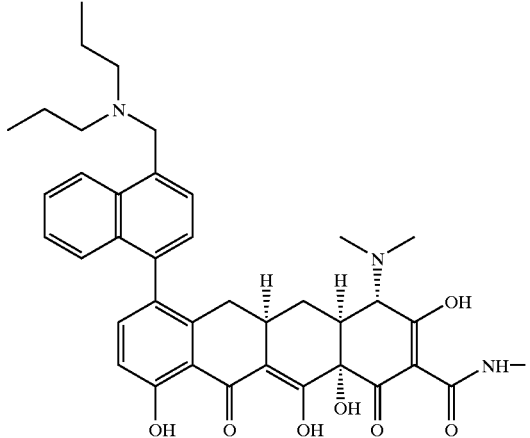 **
CZ 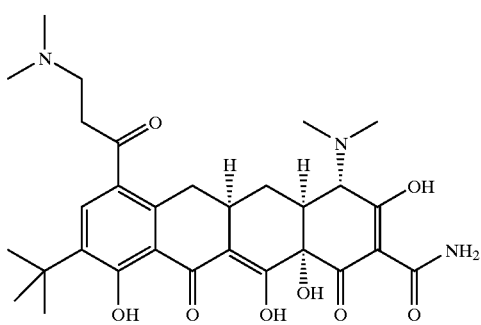 *

TABLE 2-continued

| | | |
|---|---|---|
| DA | (structure) | * |
| DB | (structure) | * |
| DC | (structure) | * |
| DD | (structure) | ** |
| DE | (structure) | * |
| DF | (structure) | ** |

TABLE 2-continued
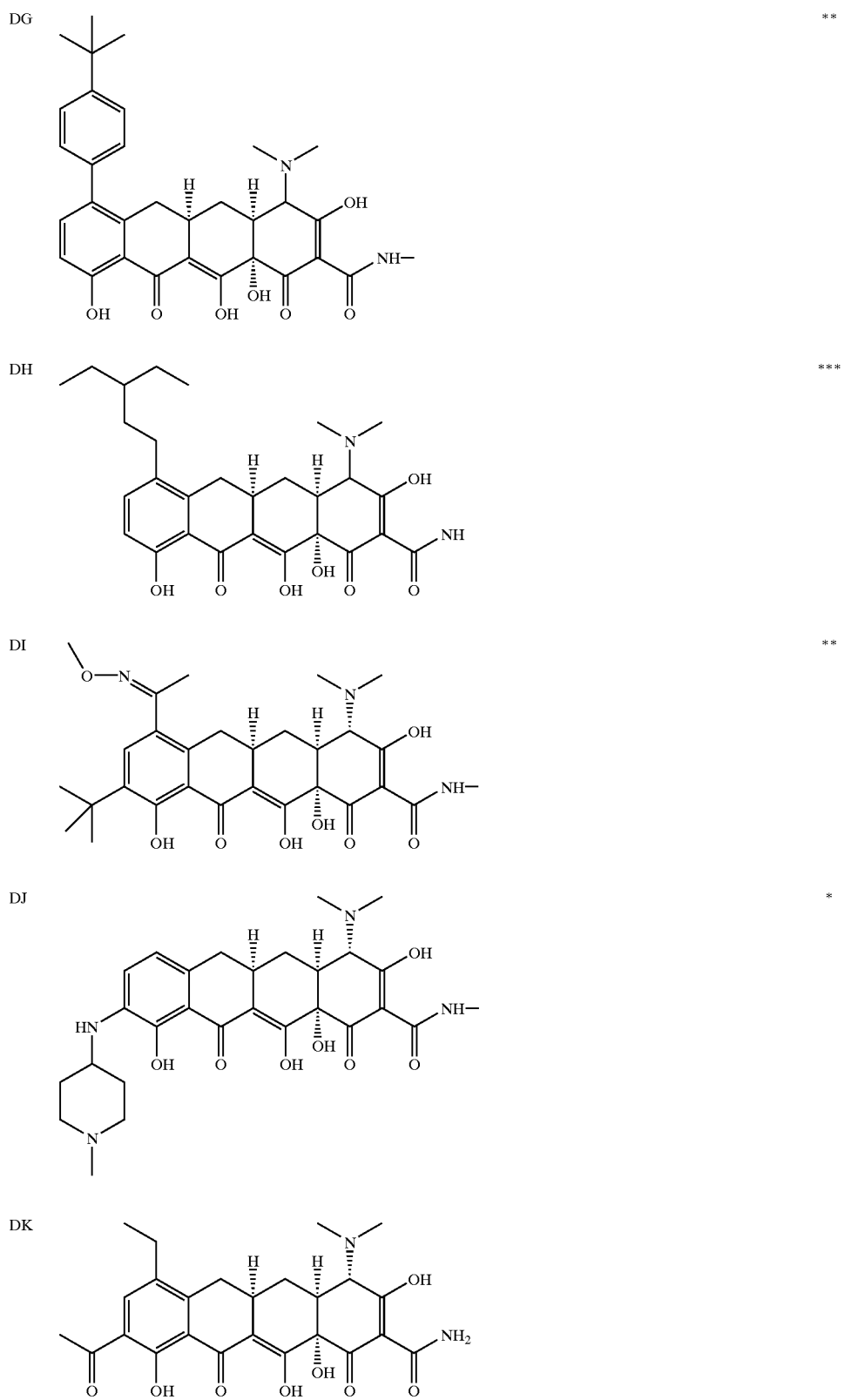

TABLE 2-continued
| | | |
|---|---|---|
| DL | 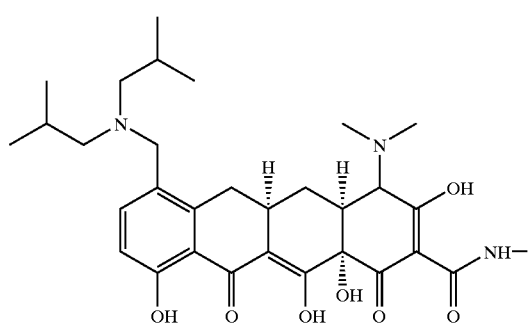 | * |
| DM | 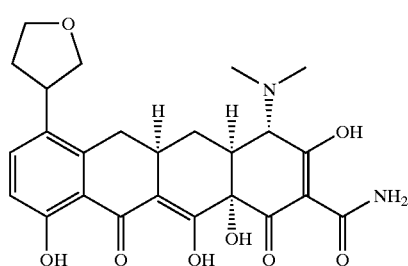 | * |
| DN | 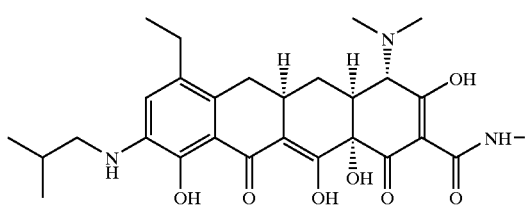 | ** |
| DO | 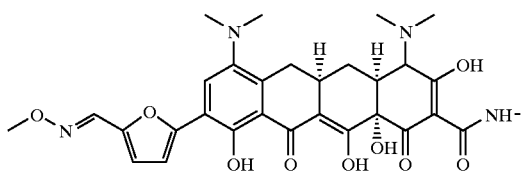 | |
| DP | 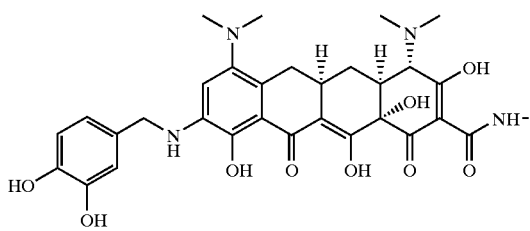 | * |
| DQ | 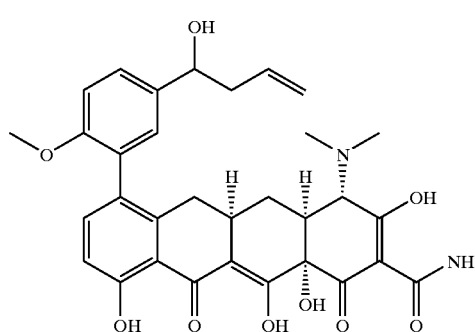 | |

TABLE 2-continued
| ID | STRUCTURE |
|---|---|
| DR | 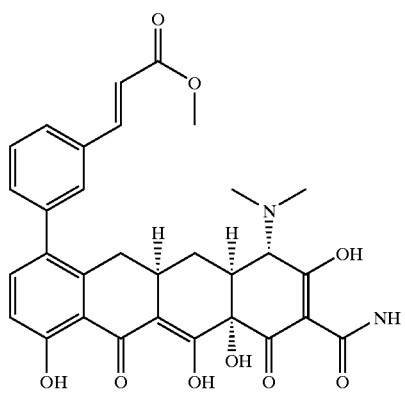 |
| DS | 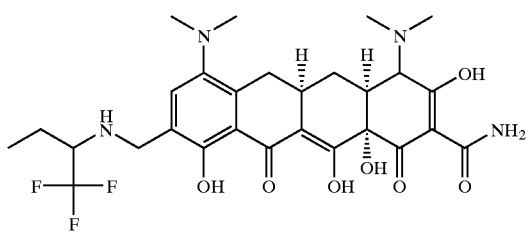 |
| ID | STRUCTURE | Candida krusei | Candida lusitaniae | Candida parapsilosis | Candida tropicalis | Cryptococcus neoformans | I orientalis | Saccharomyces cerevisiae | In Vitro Cytotoxicity |
|---|---|---|---|---|---|---|---|---|---|
| A | 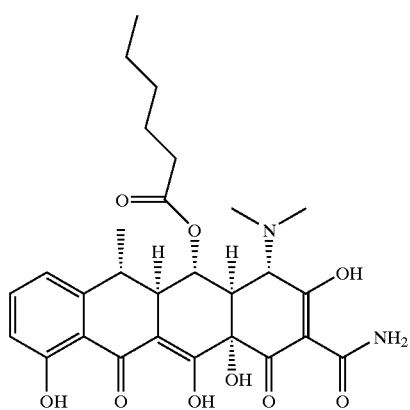 | | | | | | | | ** |
| B | 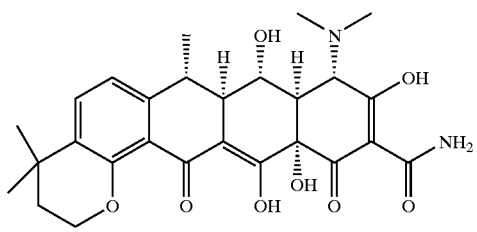 | | | | | | | | ** |

TABLE 2-continued
| | | | | | |
|---|---|---|---|---|---|
| C 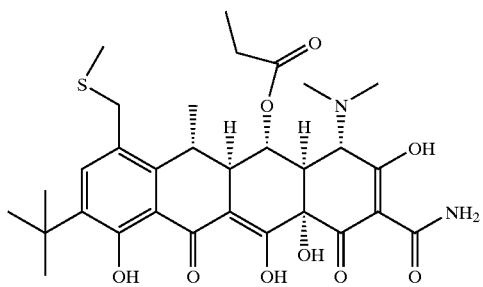 | | | | | ** |
| D 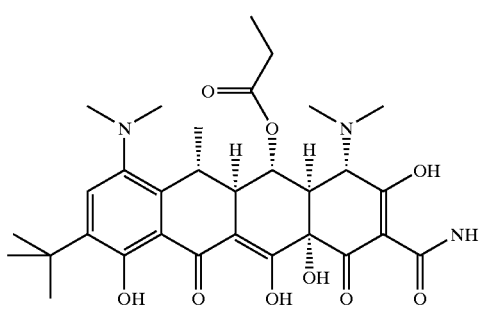 | | | | | ** |
| E 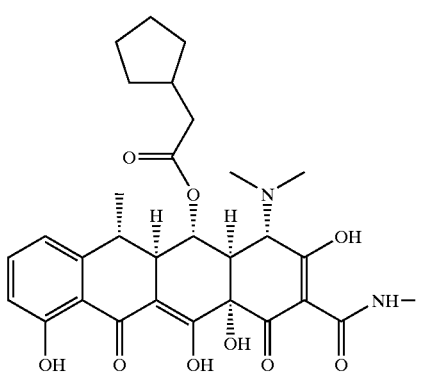 | | * | | * | ** |
| F 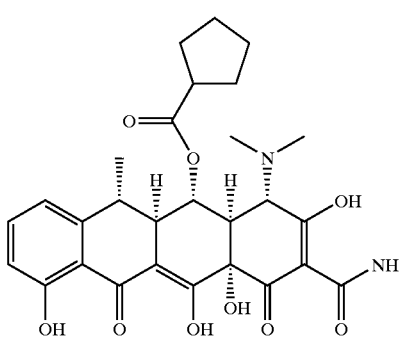 | | | | | ** |
| G 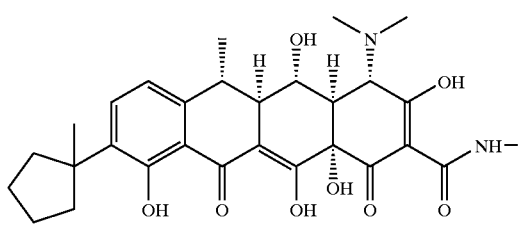 | |  | * |  |  |

TABLE 2-continued
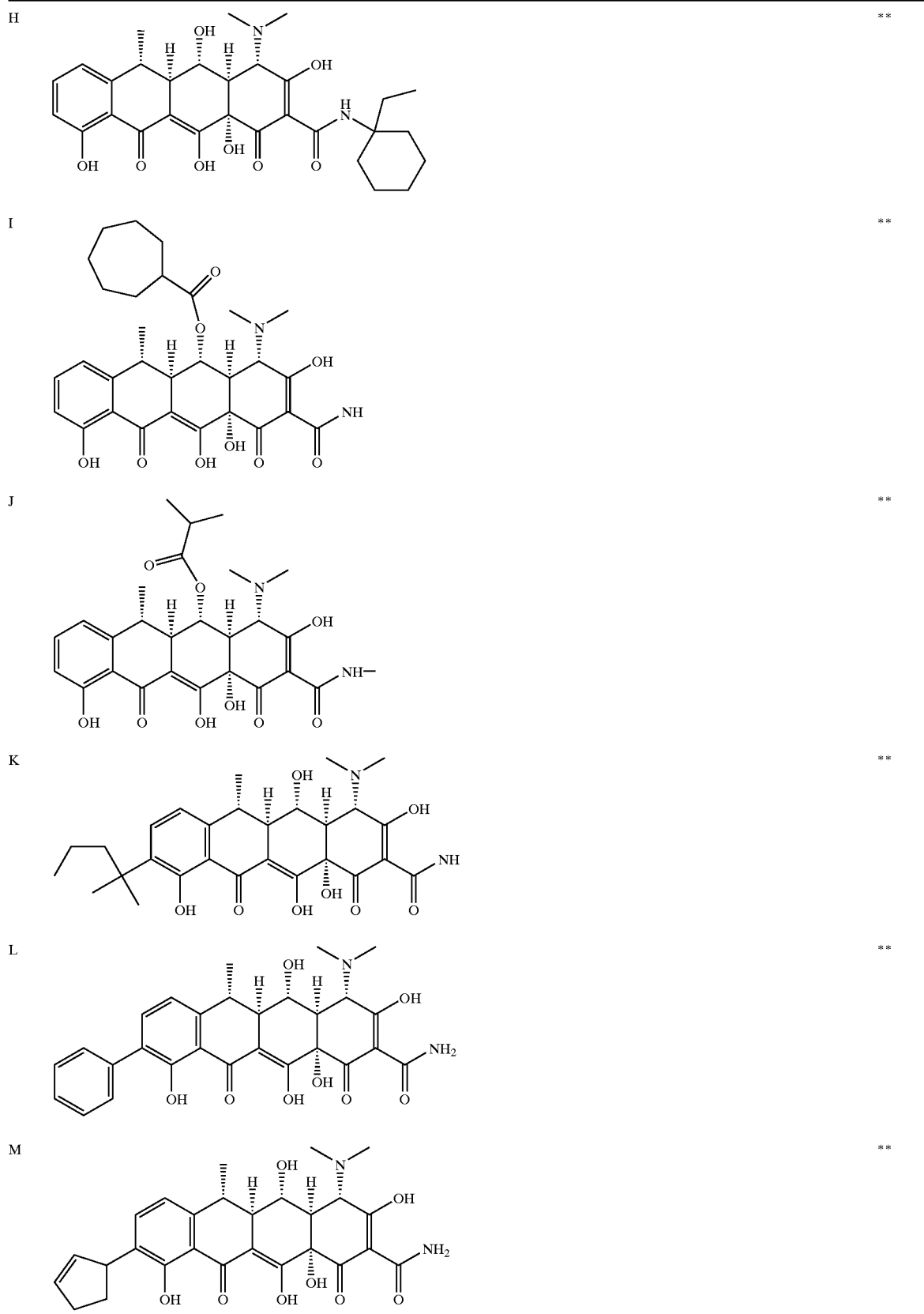
| H | | ** |
| I | | ** |
| J | | ** |
| K | | ** |
| L | | ** |
| M | | ** |

TABLE 2-continued

| | | | | |
|---|---|---|---|---|
| N | (structure) | | | ** |
| O | (structure) | | | ** |
| P | (structure) | * | | ** |
| Q | (structure) | * | * | ** |
| R | (structure) | | | ** |
| S | (structure) | | | ** |
| T | (structure) | | | ** |

TABLE 2-continued
| | | |
|---|---|---|
| U | 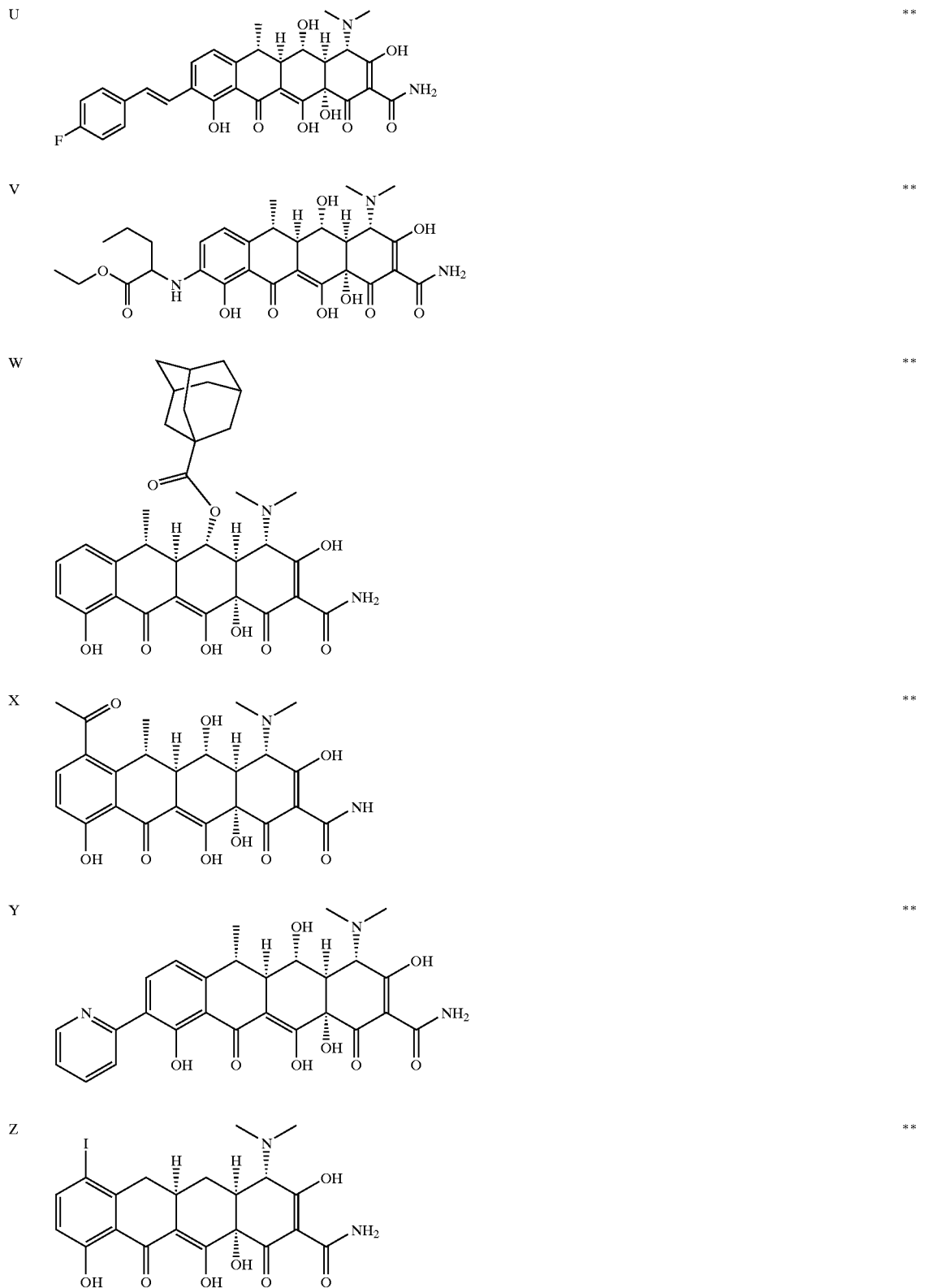 | ** |
| V | | ** |
| W | | ** |
| X | | ** |
| Y | | ** |
| Z | | ** |

TABLE 2-continued
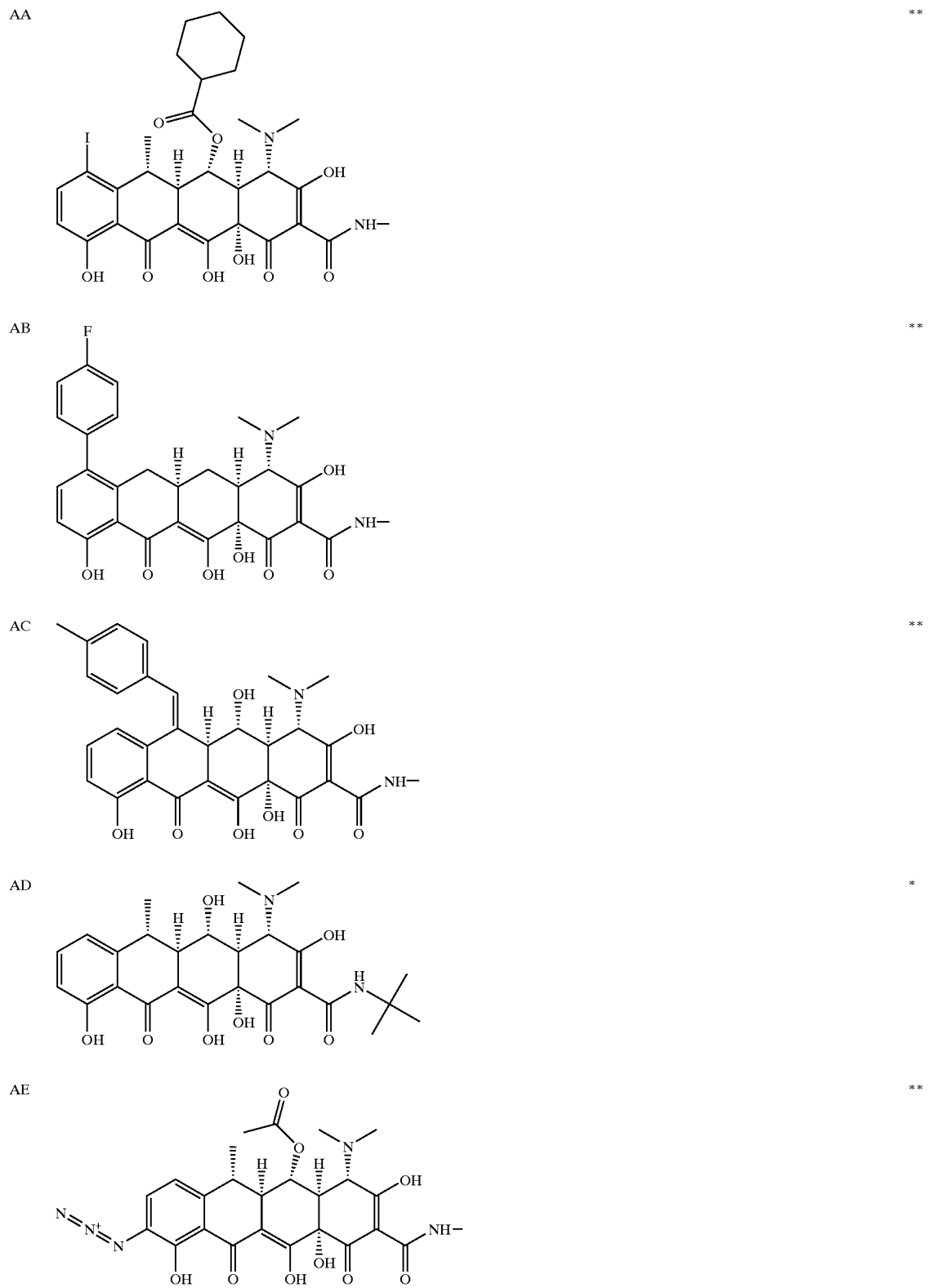

TABLE 2-continued
| | | |
|---|---|---|
| AF | 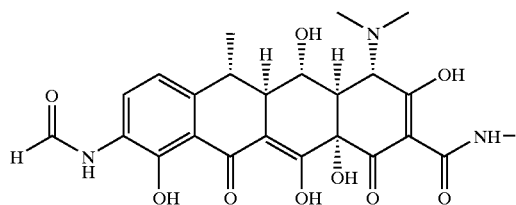 | ** |
| AG | 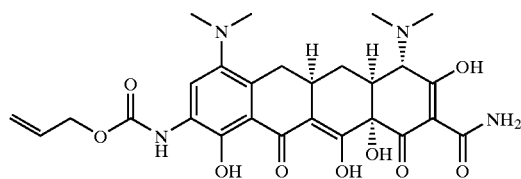 | ** |
| AH | 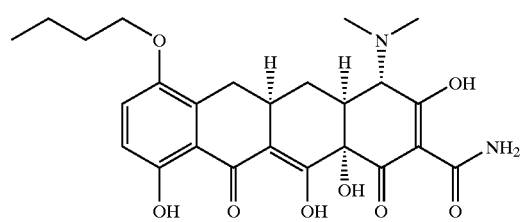 | ** |
| AI | 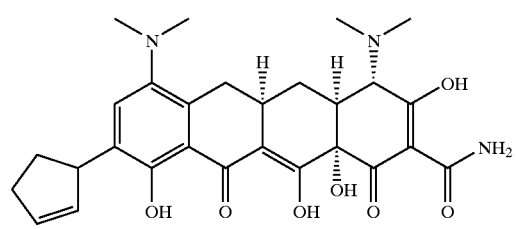 | ** |
| AJ | 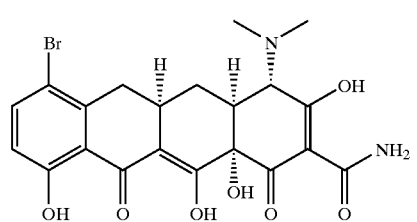 | ** |
| AK | 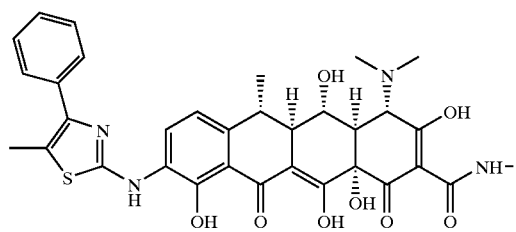 | ** |
| AL | 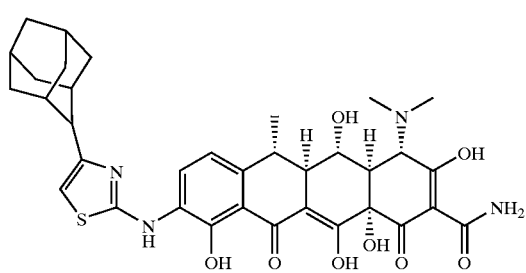 | ** |

TABLE 2-continued
| | | |
|---|---|---|
| AM | 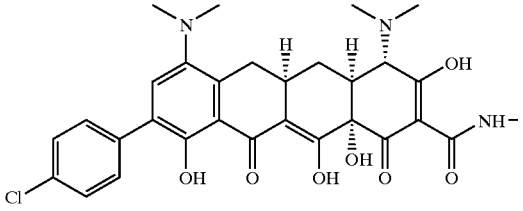 | ** |
| AN | 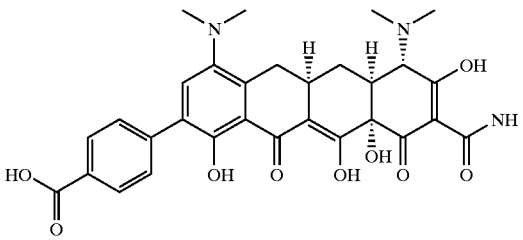 | ** |
| AO | 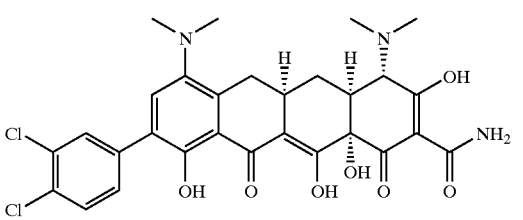 | ** |
| AP | 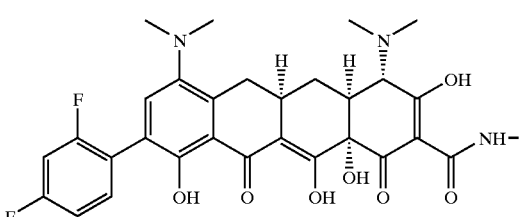 | ** |
| AQ | 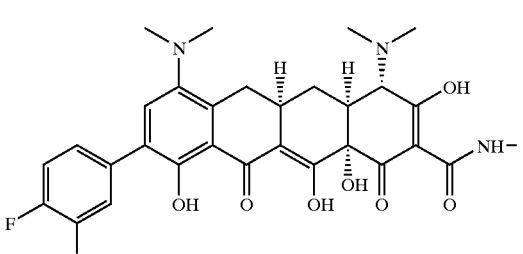 | ** |
| AR | 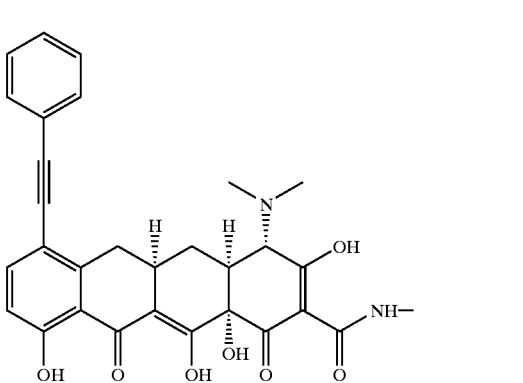 | *  * * *  |

TABLE 2-continued

| | | | | | | | | |
|---|---|---|---|---|---|---|---|---|
| AS | | | | | | | *** | ** |
| AT | | | | | | | | ** |
| AU | | | | | | | | ** |
| AV | | | | | | | * | * |
| AW | | ** | ** | ** | ** | ** | *** | ** |

TABLE 2-continued

| | | | | | |
|---|---|---|---|---|---|
| AX | [structure] | | | ** | ** |
| AY | [structure] | | | | ** |
| AZ | [structure] | | | | ** |
| BA | [structure] | ** | * | * | ** |

TABLE 2-continued

| | | | | | | | |
|---|---|---|---|---|---|---|---|
| BB | (structure) | ** | ** | ** | * | | ** |
| BC | (structure) | *** | ** | | ** | | ** |
| BD | (structure) | | | | | | ** |
| BE | (structure) | *** | ** | *** | *** | ** | ** |

TABLE 2-continued

| | | | | | | |
|---|---|---|---|---|---|---|
| BF | *** | ** | *** | *** | ** | ** |
| BG | | | | | | ** |
| BH | * | | | ** | | ** |
| BI | *** | *** | ** | ** | ** | ** |

TABLE 2-continued
| BJ | 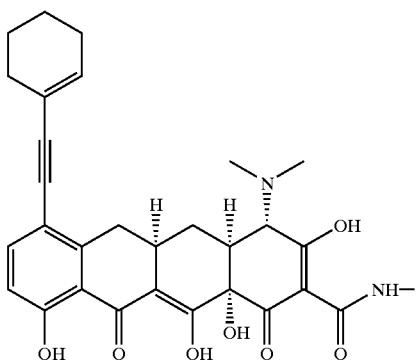 | ** | | |
| --- | --- | --- | --- | --- |
| BK | 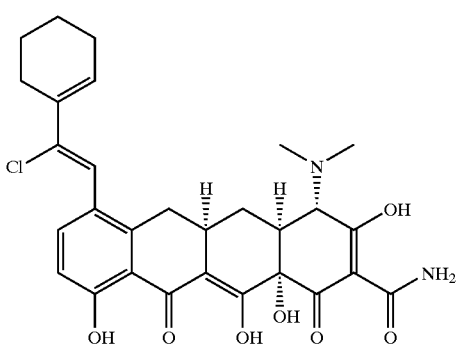 | ** | | |
| BL | 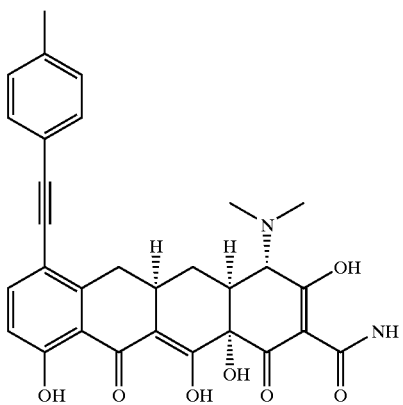 | * |  | ** |
| BM | 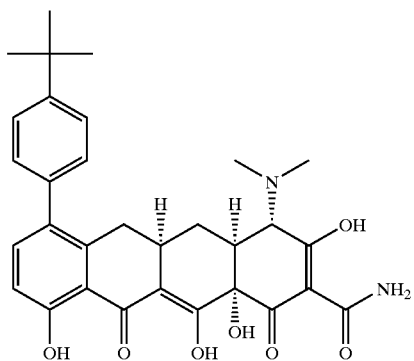 | ** | | |

TABLE 2-continued
BN 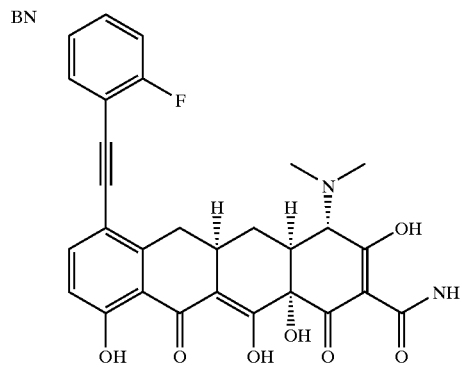 **
BO 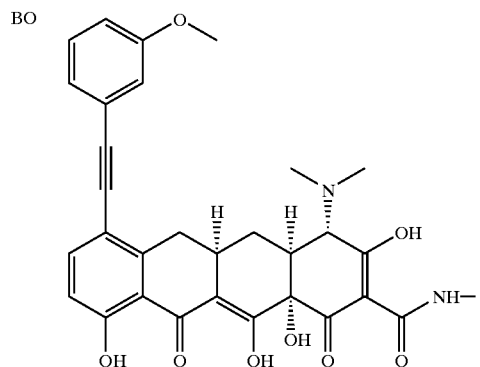 **
BP 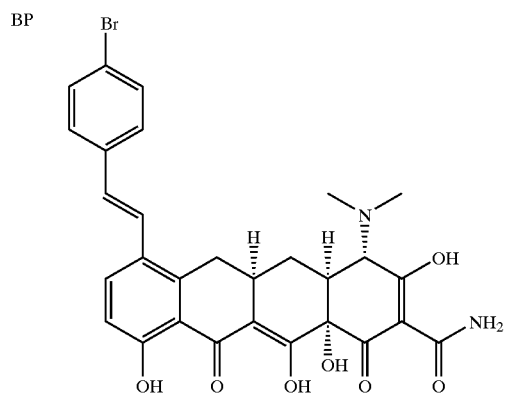 *
BQ 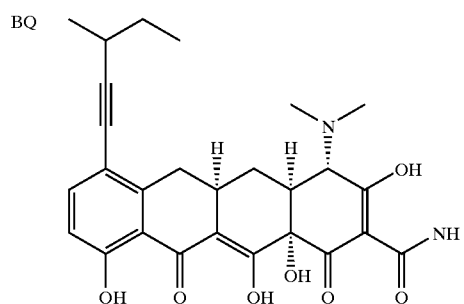 **

TABLE 2-continued

| | | | | | | | | |
|---|---|---|---|---|---|---|---|---|
| BR | [structure] | ** | ** | * | ** | * | *** | ** |
| BS | [structure] | | | | | | | ** |
| BT | [structure] | *** | ** | *** | *** | | | ** |
| BU | [structure] | ** | *** | ** | ** | ** | | ** |
| BV | [structure] | | | | | | * | ** |

TABLE 2-continued

| | | | | | | | |
|---|---|---|---|---|---|---|---|
| BW | (structure) | | | | *** | | ** |
| BX | (structure) | ** | ** | ** | *** | ** | ** | ** |
| BY | (structure) | | ** | * | * | * | | ** |
| BZ | (structure) | | | | | | | ** |
| CA | (structure) | | | | | | | ** |

TABLE 2-continued
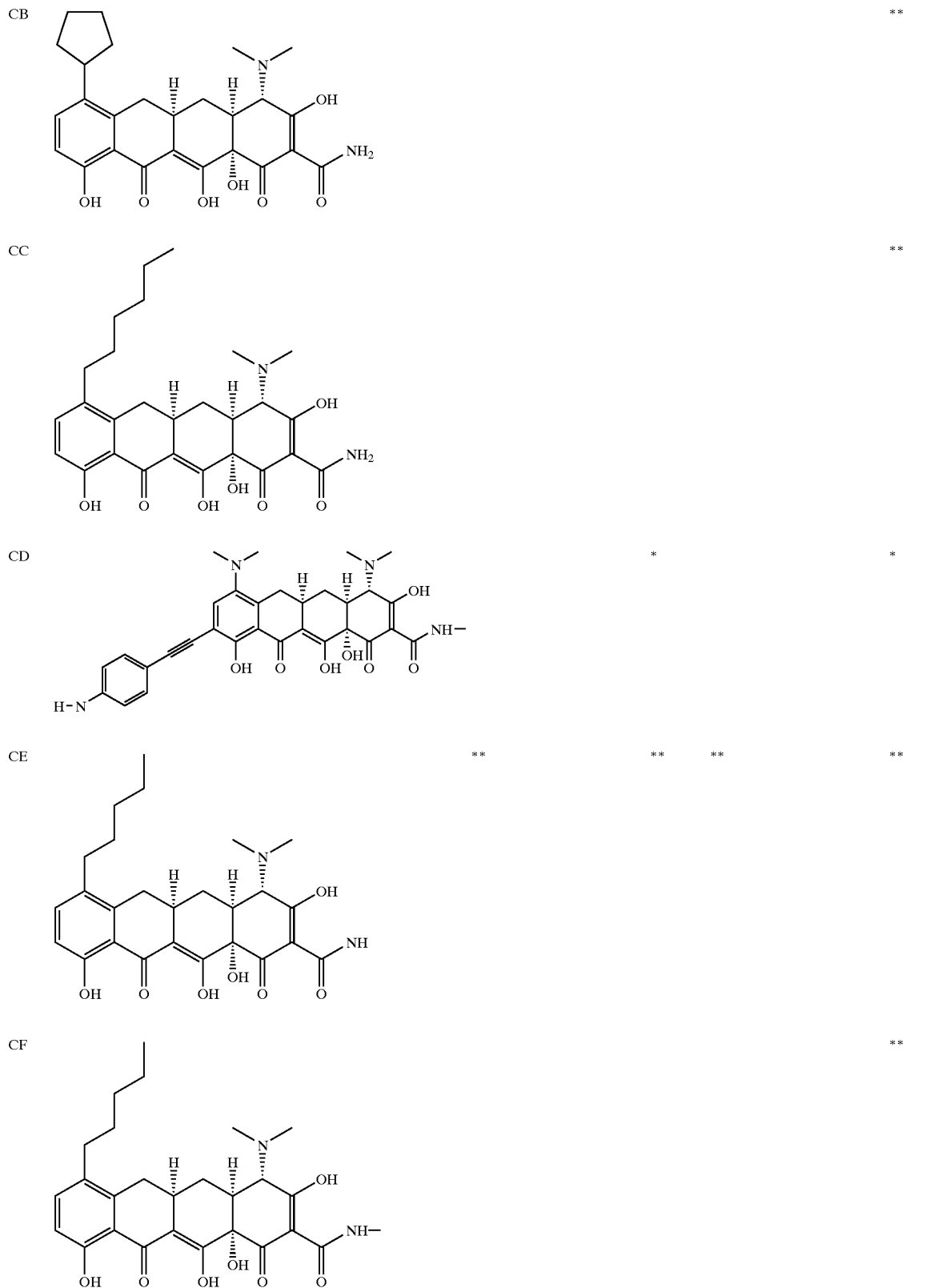

TABLE 2-continued
| CG | 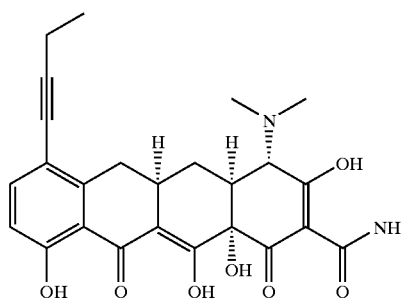 | | | | | ** |
|---|---|---|---|---|---|---|
| CH | 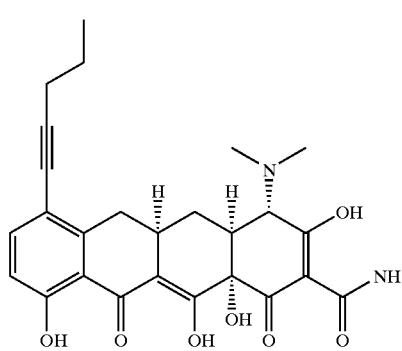 | * |  |  | | ** |
| CI | 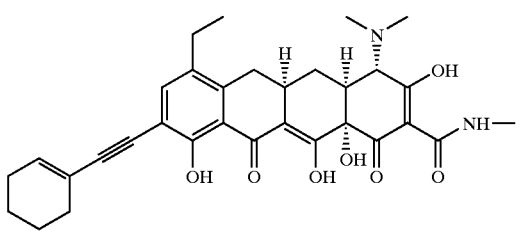 | | | | | ** |
| CJ | 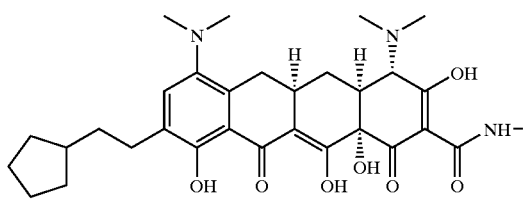 | * |  |  |  |  | ** |
| CK | 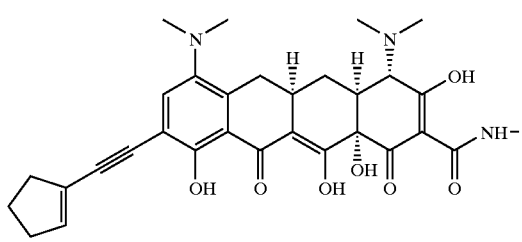 | | | | | ** |

TABLE 2-continued
| | | | | | | | | |
|---|---|---|---|---|---|---|---|---|
| CL | 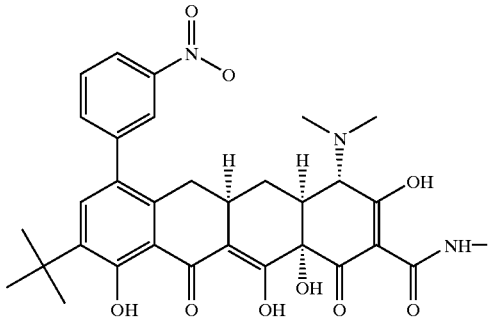 | |  | * | * | * |  |  |
| CM | 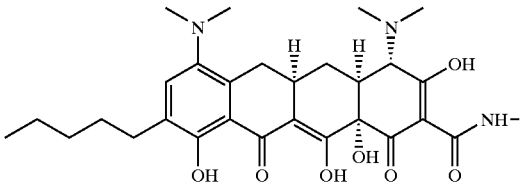 | | * | * | ** | * |  |  |
| CN | 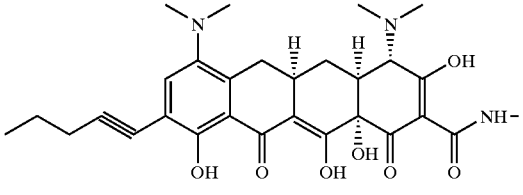 | | | | | | | ** |
| CO | 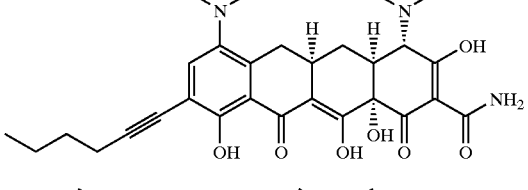 | | | | | | | ** |
| CP | 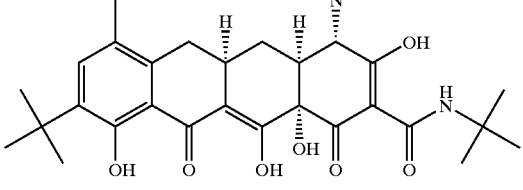 | | | | | | * |  |
| CQ | 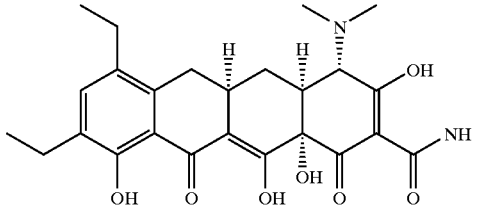 | | * | | ** | * | | ** |
| CR | 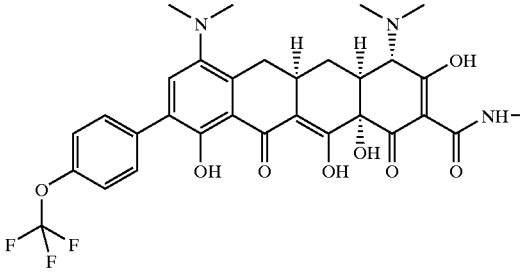 | | | | | | | ** |

TABLE 2-continued
| | | |
|---|---|---|
| CS | 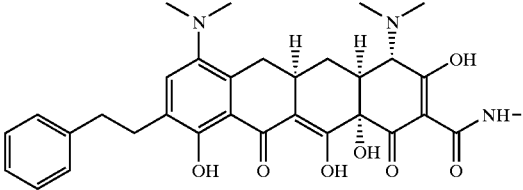 | ** |
| CT | 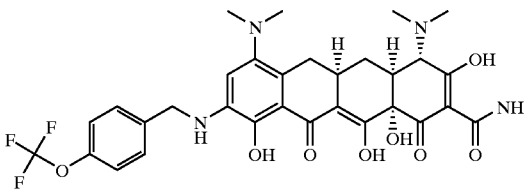 | ** |
| CU | 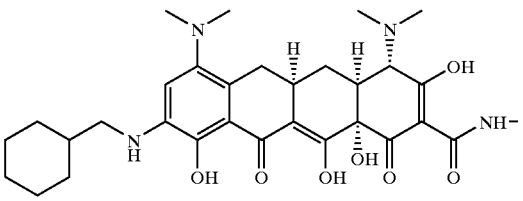 | ** |
| CV | 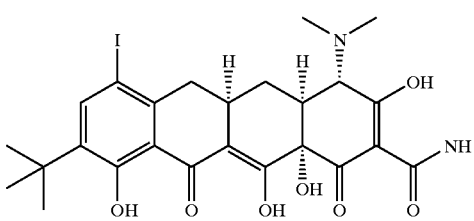 | ** |
| CW | 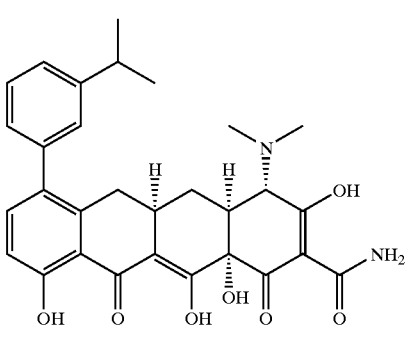 | ** |
| CX | 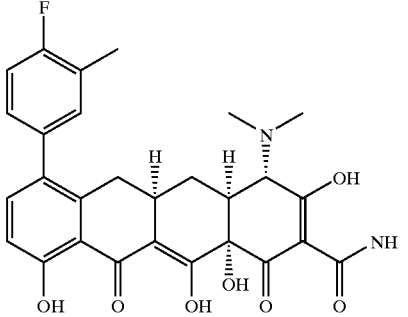 | ** |

TABLE 2-continued
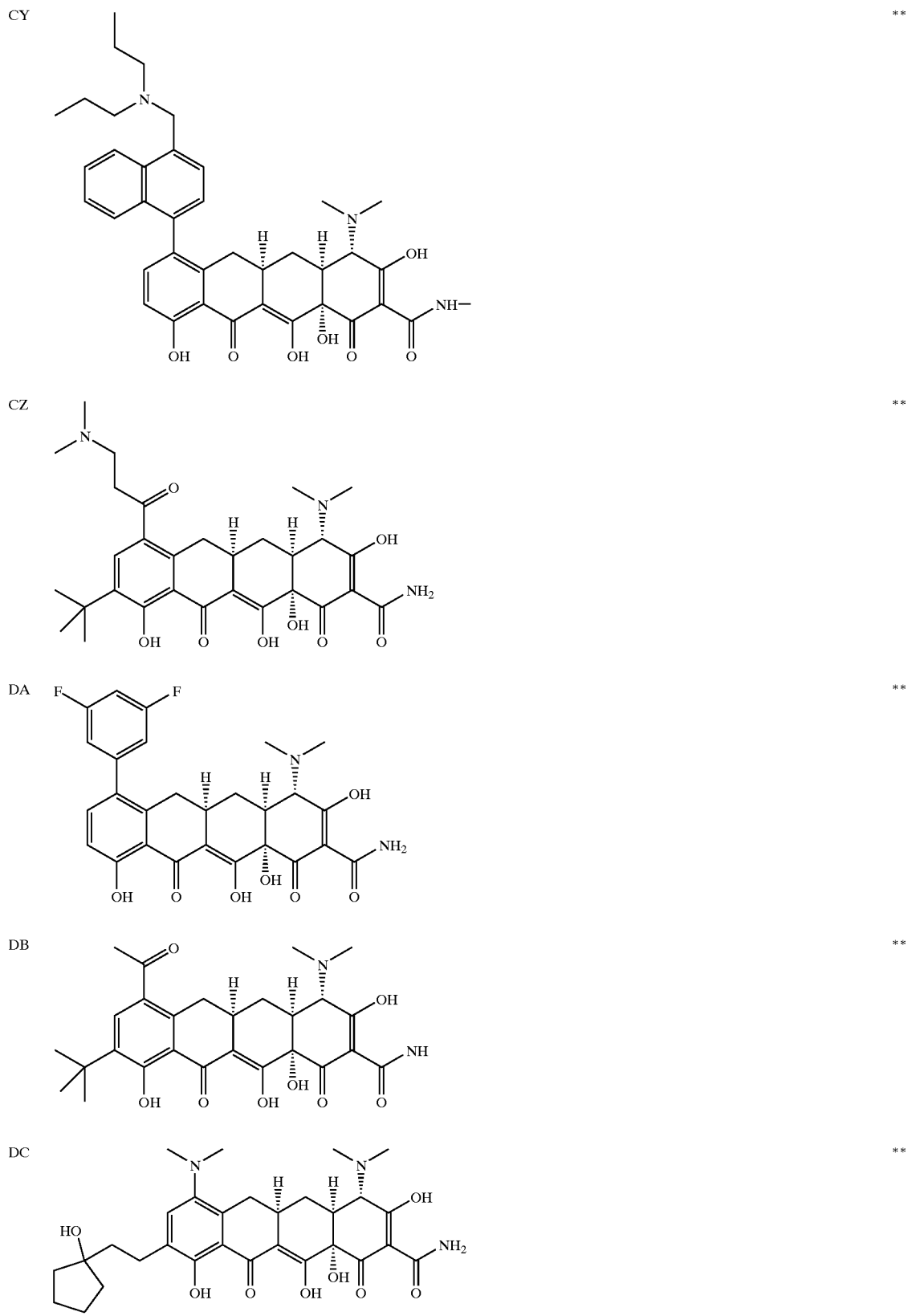

TABLE 2-continued

| | | | |
|---|---|---|---|
| DD | | | ** |
| DE | | | ** |
| DF | | *** | ** |
| DG | | *** | ** |
| DH | | *** | ** |

TABLE 2-continued

| | | |
|---|---|---|
| DI | [structure] | ** |
| DJ | [structure] | * |
| DK | [structure] | * ** |
| DL | [structure] | ** |
| DM | [structure] | * |
| DN | [structure] | ** ** |

TABLE 2-continued

| | | | |
|---|---|---|---|
| DO | 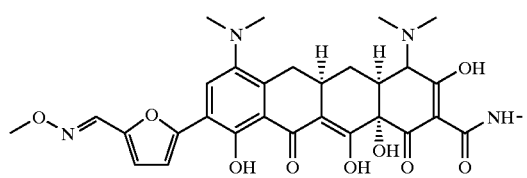 | * | ** |
| DP | 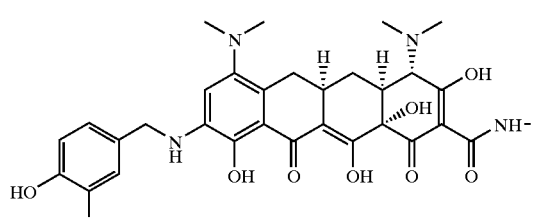 | * | * |
| DQ | 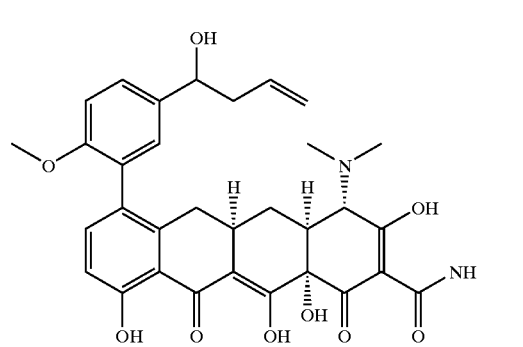 |  |  |
| DR | 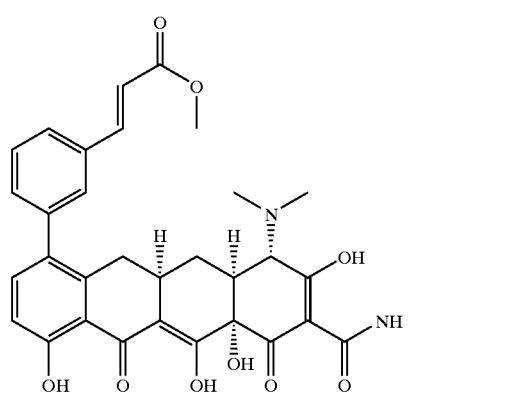 | * |  |
| DS | 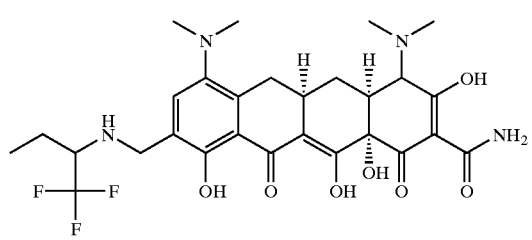 |  |  |

EXAMPLE 3

Mammalian Cytotoxicity Assay

COS-1 and CHO cell suspensions are prepared, seeded into 96-well tissue culture treated black-walled microtiter plates (density determined by cell line), and incubated overnight at 37° C., in 5% $CO_2$ and approximately 95% humidity. The following day serial dilutions of drug are prepared under sterile conditions and transferred to cell plates. Cell/Drug plates are incubated under the above conditions for 24 hours. Following the incubation period, media/drug is aspirated and 50 μl of Resazurin is added. Plates are then incubated under the above conditions for 2 hours and then in the dark at room temperature for an additional 30 minutes. Fluorescence measurements are taken (excitation 535 nm, emission 590 nm). The $IC_{50}$ (concentration of drug causing 50% growth inhibition) is then calculated. The cytotoxcity of both unsubstituted minocycline and doxycycline were found to be greater than 25.

EXAMPLE 4

In Vitro Anti-Bacterial Activity Assay

The following assay is used to determine the efficacy of the tetracycline compounds against common bacteria. 2 mg of each compound is dissolved in 100 μl of DMSO. The solution is then added to cation-adjusted Mueller Hinton broth (CAMHB), which results in a final compound concentration of 200 μg per ml. The tetracycline compound solutions are diluted to 50 μL volumes, with a test compound concentration of 0.098 μg/ml. Optical density (OD) determinations are made from fresh log-phase broth cultures of the test strains. Dilutions are made to achieve a final cell density of 1×10⁶ CFU/ml. At OD=1, cell densities for different genera should be approximately:

| | |
|---|---|
| E. coli | 1 × 10⁹ CFU/ml |
| S. aureus | 5 × 10⁸ CFU/ml |
| Enterococcus sp. | 2.5 × 10⁹ CFU/ml |

50 μl of the cell suspensions are added to each well of microtiter plates. The final cell density should be approximately 5×10⁵ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A method for inhibiting the growth of a fungus, comprising contacting said fungus with an effective amount of a substituted tetracycline compound, such that the growth of said fungus is inhibited, wherein said substituted tetracycline is not unsubstituted minocycline.

2. The method of claim 1, wherein said substituted tetracycline compound is of formula I:

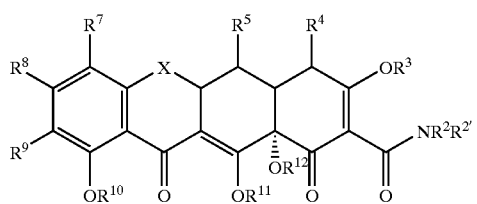

(I)

X is CHC($R^{13}$Y'Y), $CR^{6'}R^6$, S, $NR^6$, or O;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, hydroxyl, halogen, or hydrogen;
$R^3$, $R^{11}$ and $R^{12}$ are each hydrogen, or a pro-drug moiety;
$R^{10}$ hydrogen, a prodrug moiety, or linked to $R^9$ to form a ring;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —($CH_2$)$_{0-3}NR^{7c}C(=W')WR^{7a}$;
$R^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —($CH_2$)$_{0-3}NR^{9c}C(=Z')ZR^{9a}$;
Z is $CR^{9d}R^{9e}$, S, $NR^{9b}$ or O;
Z' is O, S, or $NR^{9f}$;
W is $CR^{7d}R^{7e}$, S, $NR^{7b}$ or O;
W' is O, $NR^{7f}$S;
$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

3. The method of claim 2, wherein $R^{2'}$, $R^3$, $R^{10}$, $R^{11}$, and $R^{12}$ are each hydrogen or a prodrug moiety.

4. The method of claim 2, wherein $R^4$ is $NR^{4'}R^{4''}$.

5. The method of claim 4, wherein $R^{4'}$ and $R^{4''}$ are each methyl.

6. The method of claim 2, wherein X is $CR^6R^{6'}$; and $R^2$, $R^5$, $R^6$, $R^{6'}$, and $R^8$ are each hydrogen.

7. The method of claim 2, wherein $R^9$ is hydrogen.

8. The method of claim 2, wherein $R^7$ aryl.

9. The method of claim 8, wherein $R^7$ is substituted or unsubstituted phenyl.

10. The method of claim 8, wherein said substituted or unsubstituted phenyl is substituted with at least one alkyl, halogen, nitro, or alkenyl.

11. The method of claim 8, wherein $R^7$ is substituted or unsubstituted heteroaryl.

12. The method of claim 10, wherein said heteroaryl is bicyclic.

13. The method of claim 2, wherein $R^7$ substituted or unsubstituted alkyl.

14. The method of claim 13, wherein said alkyl is $C_1$–$C_{10}$.

15. The method of claim 2, wherein $R^7$ is substituted or unsubstituted alkenyl.

16. The method of claim 15, wherein said substituted alkenyl is substituted with an alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl or heteroaryl moiety.

17. The method of claim 15, wherein said substituted alkenyl is substituted with substituted or unsubstituted cyclic moiety.

18. The method of claim 17, wherein said cyclic moiety is heterocyclic, cycloalkenyl, cycloalkyl, cycloalkynyl, or aryl.

19. The method of claim 18, wherein said cyclic moiety is substituted or unsubstituted phenyl.

20. The method of claim 2, wherein $R^7$ is substituted or unsubstituted alkynyl.

21. The method of claim 19, wherein said substituted alkynyl is substituted with a cyclic moiety.

22. The method of claim 21, wherein said cyclic moiety is heterocyclic, cycloalkenyl, cycloalkyl, aryl, or aralkyl.

23. The method of claim 22, wherein said cyclic moiety is substituted or unsubstituted phenyl or substituted or unsubstituted cycloalkyl.

24. The method of claim 2, wherein $R^7$ is alkoxy.

25. The method of claim 2, wherein $R^5$ is hydroxy or alkylcarbonyloxy; X is $CHR^6$; $R^6$ is alkyl; and $R^8$ is hydrogen.

26. The method of claim 2, wherein $R^6$ is methyl.

27. The method of claim 25, wherein $R^7$ is hydrogen.

28. The method of claim 25, wherein $R^9$ is substituted or unsubstituted aryl.

29. The method of claim 25, wherein $R^9$ is substituted or unsubstituted alkyl or $N_3$.

30. The method of claim 25, wherein $R^2$ is hydrogen.

31. The method of claim 25, wherein $R^9$ is hydrogen and $R^8$ is alkyl.

32. The method of claim 2, wherein X is $CR^6R^{6'}$; and $R^2$, $R^5$, $R^6$, $R^{6'}$, and $R^8$ are each hydrogen, and $R^7$ is dimethyl amino.

33. The method of claim 32, wherein $R^9$ is substituted or unsubstituted aryl or aralkyl.

34. The method of claim 33, wherein said aryl is phenyl, benzofuranyl, or pyridyl.

35. The method of claim 32, wherein $R^9$ is substituted or unsubstituted alkyl or substituted or unsubstituted alkenyl.

36. The method of claim 35, wherein $R^9$ is substituted with a substituted or unsubstituted phenyl group.

37. The method of claim 32, wherein $R^9$ is substituted or unsubstituted amino.

38. The method of claim 32, wherein said amino is substituted with a heteroaryl group.

39. The method of claim 38, wherein said heteroaryl is substituted or unsubstituted thioazolyl.

40. The method of claim 32, wherein $R^9$ is substituted or unsubstituted alkynyl.

41. The method of claim 40, wherein said substituted alkynyl is substituted with a cyclic moiety.

42. The method of claim 41, wherein said cyclic moiety is heterocyclic, cycloalkenyl, cycloalkyl, aryl, or aralkyl.

43. The method of claim 42, wherein said cyclic moiety is substituted or unsubstituted phenyl or substituted or unsubstituted cycloalkyl.

44. The method of claim 32, wherein $R^9$ is substituted aminoalkyl.

45. The method of claim 1, wherein said substituted tetracycline compound has greater antifungal activity than doxycycline.

46. The method of claim 1, wherein said substituted tetracycline compound has greater antifungal activity than minocycline.

47. The method of claim 1, wherein said tetracycline compound is non-antibacterial.

48. Method of claim 1, wherein said tetracycline compound has anti-inflammatory activity.

49. The method of claim 2, wherein said substituted tetracycline compound is selected from the group consisting of:

135
-continued
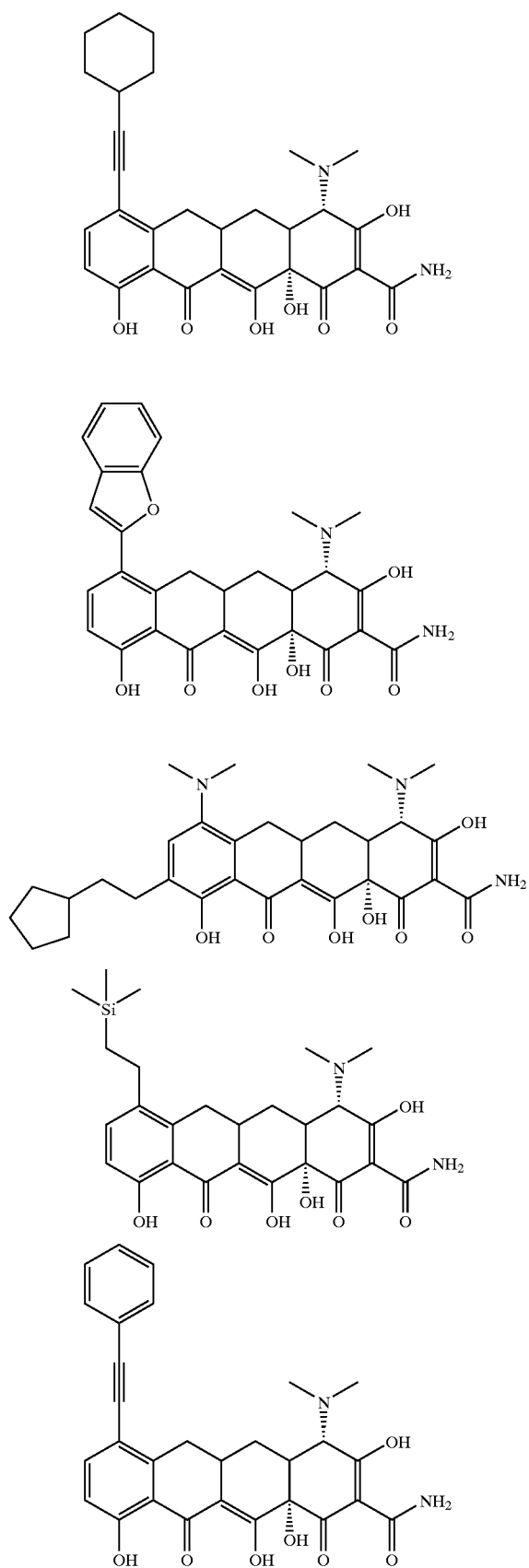
136
-continued
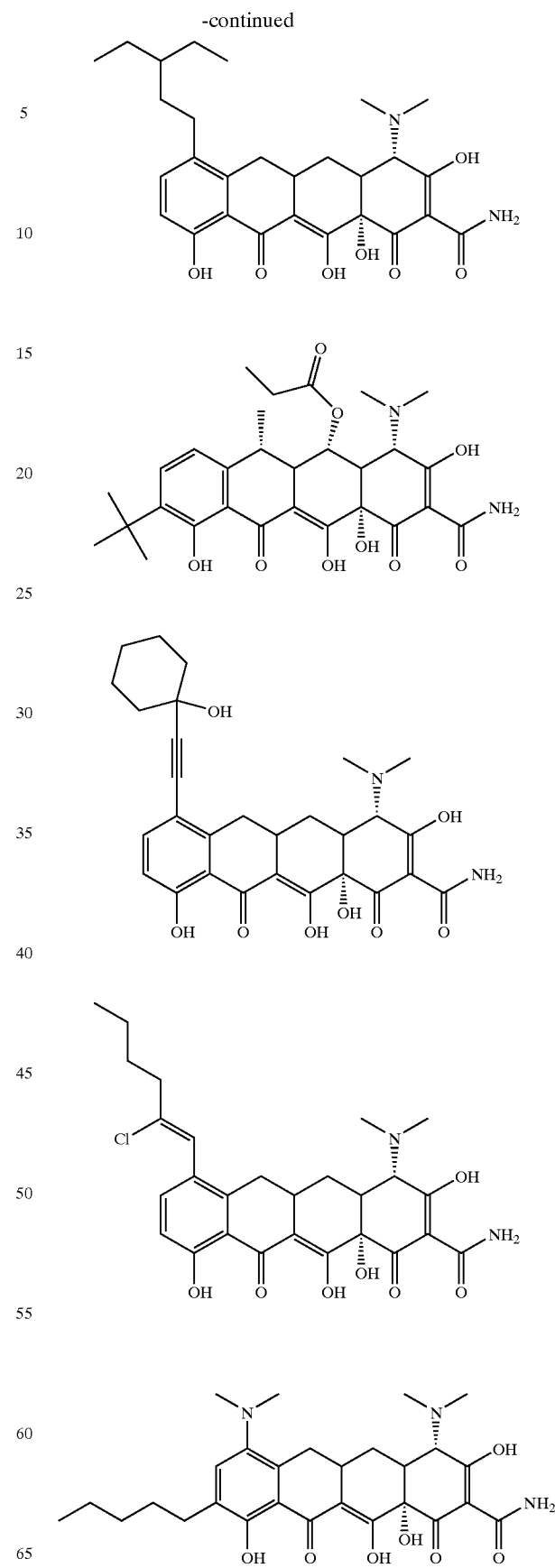

137
-continued
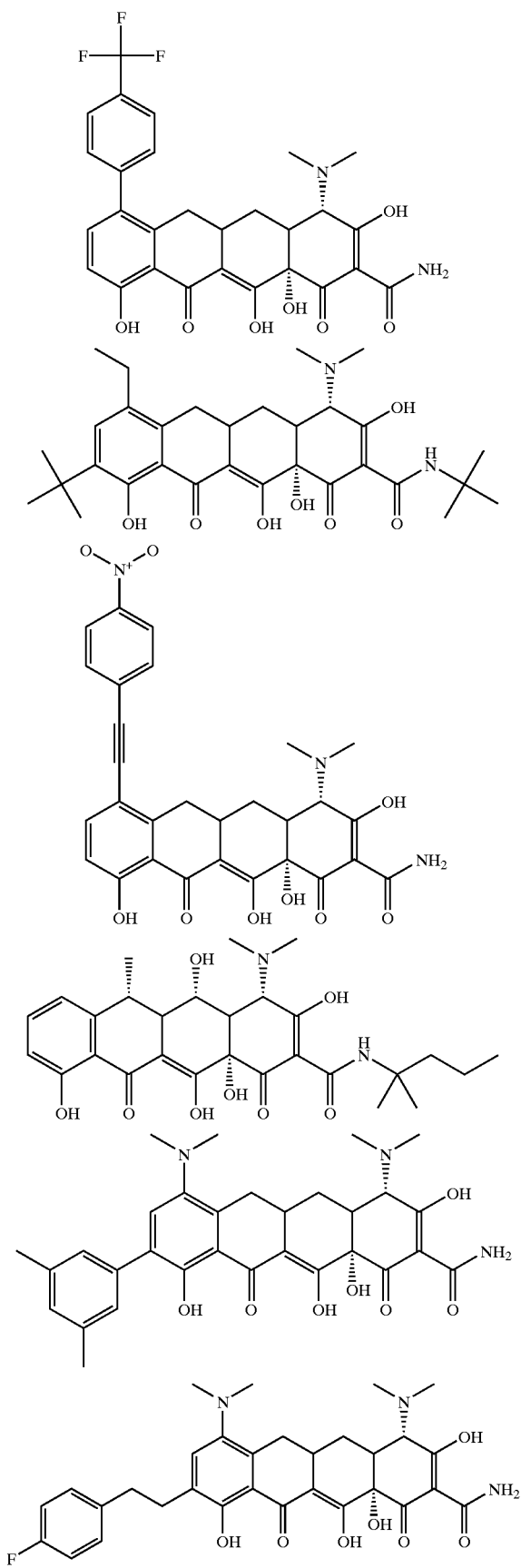
138
-continued
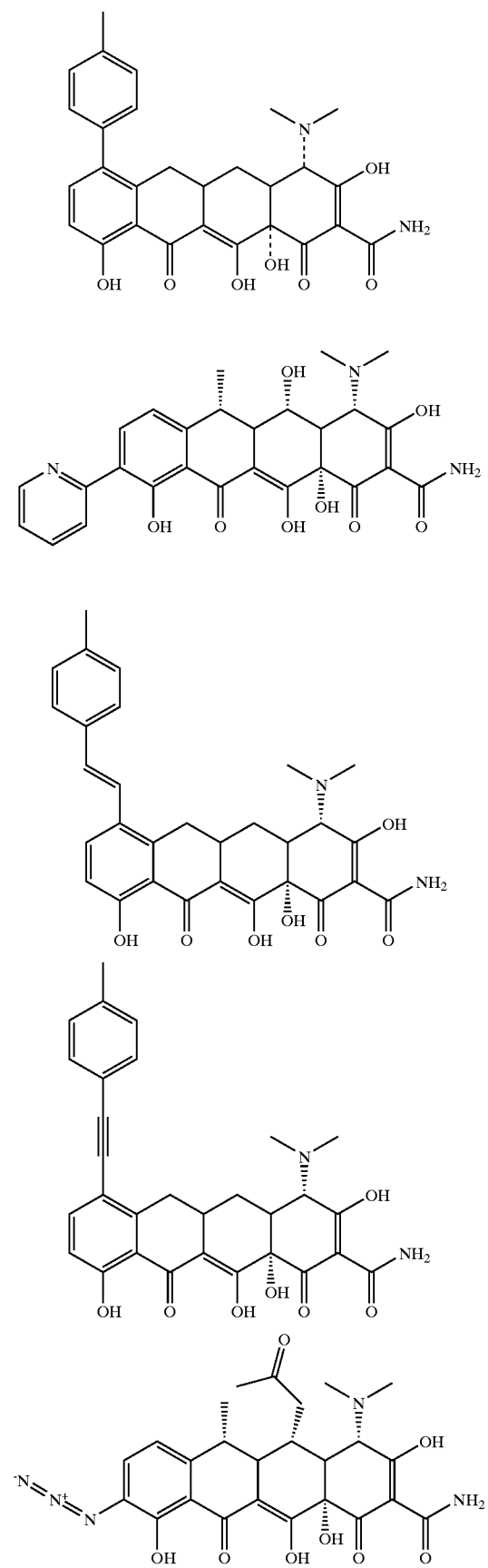

-continued
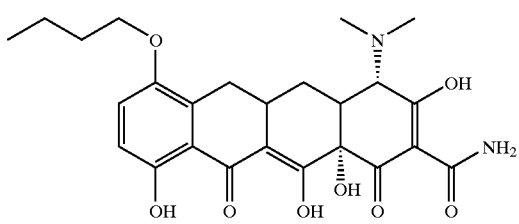
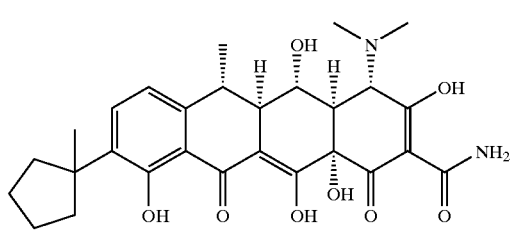
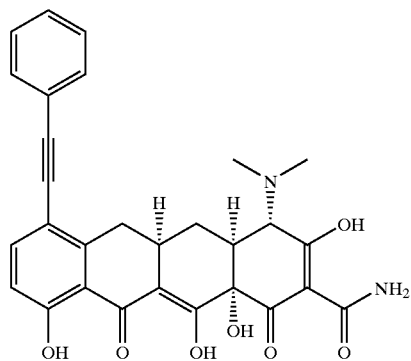
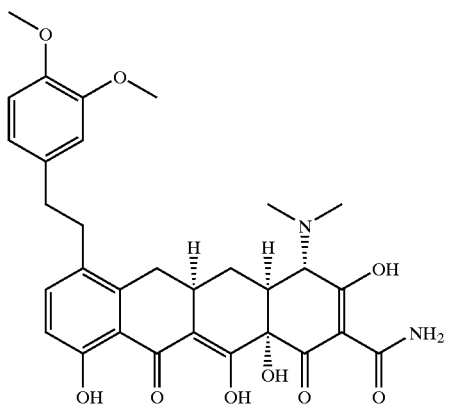
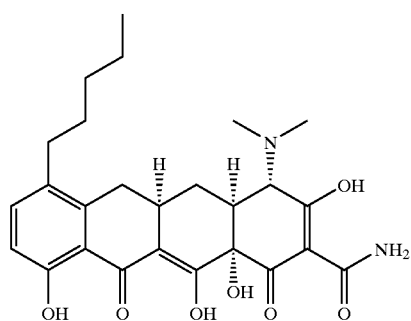
-continued
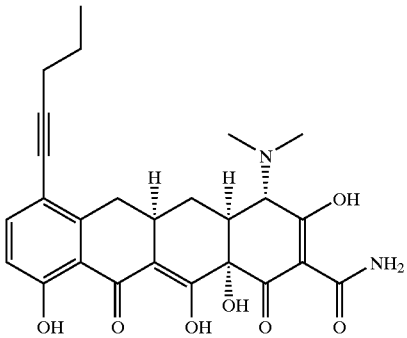
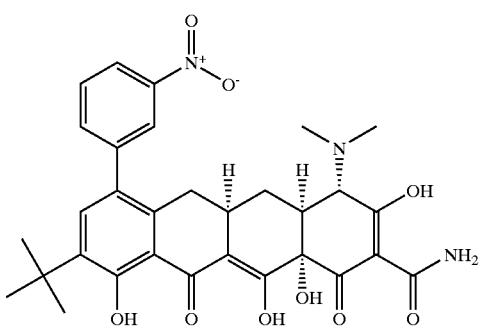
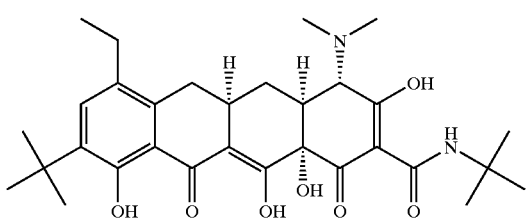
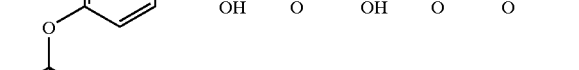
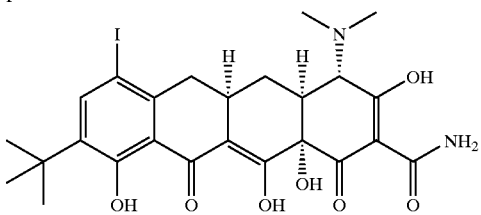
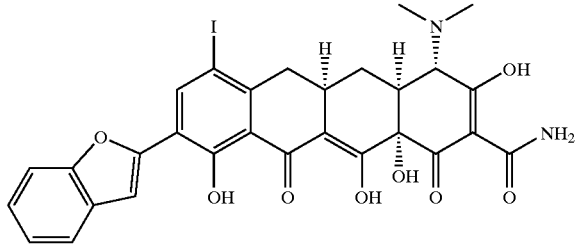

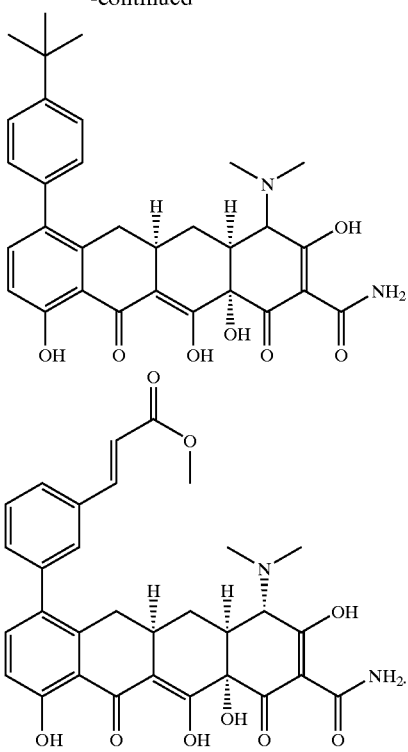

50. The method of claim 1, wherein the growth of the fungus is static.

51. The method of claim 1, wherein the tetracycline compound inhibits the growth of said fungus by killing said fungus.

52. The method of claim 1, wherein said fungus is in the genus Candida.

53. A method for treating a fungal associated disorder in a subject, comprising administering to said subject an effective amount of a substituted tetracycline compound such that said subject is treated for said fungal associated disorder, wherein said substituted tetracycline compound is not unsubstituted minocycline.

54. The method of claim 53, wherein said substituted tetracycline compound is of formula I:

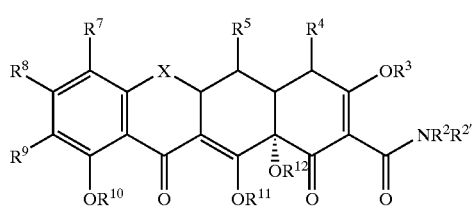

X is $CHC(R^{13}Y'Y)$, $CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, hydroxyl, halogen, or hydrogen;

$R^3$, $R^{11}$ and $R^{12}$ are each hydrogen, or a pro-drug moiety;

$R^{10}$ hydrogen, a prodrug moiety, or linked to $R^9$ to form a ring;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —$(CH_2)_{0-3}NR^{7c}C(=W')WR^{7a}$;

$R^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —$(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

55. The method of claim 54, wherein $R^{2'}$, $R^3$, $R^{10}$, $R^{11}$, and $R^{12}$ are each hydrogen or a prodrug moiety.

56. The method of claim 54, wherein $R^4$ is $NR^{4'}R^{4''}$.

57. The method of claim 56, wherein $R^{4'}$ and $R^{4''}$ are each methyl.

58. The method of claim 54, wherein X is $CR^6R^{6'}$; and $R^2$, $R^5$, $R^6$, $R^{6'}$, and $R^8$ are each hydrogen.

59. The method of claim 54, wherein $R^9$ is hydrogen.

60. The method of claim 54, wherein $R^7$ is aryl.

61. The method of claim 60, wherein $R^7$ is substituted or unsubstituted phenyl.

62. The method of claim 61, wherein said substituted or unsubstituted phenyl is substituted with at least one alkyl, halogen, nitro, or alkenyl.

63. The method of claim 62, wherein $R^7$ is substituted or unsubstituted heteroaryl.

64. The method of claim 63, wherein said heteroaryl is bicyclic.

65. The method of claim 54, wherein $R^7$ substituted or unsubstituted alkyl.

66. The method of claim 64, wherein said alkyl is $C_1$–$C_{10}$.

67. The method of claim 54, wherein $R^7$ is substituted or unsubstituted alkenyl.

68. The method of claim 67, wherein said substituted alkenyl is substituted with an alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl or heteroaryl moiety.

69. The method of claim 67, wherein said substituted alkenyl is substituted with substituted or unsubstituted cyclic moiety.

70. The method of claim 69, wherein said cyclic moiety is heterocyclic, cycloalkenyl, cycloalkyl, cycloalkynyl, or aryl.

71. The method of claim 70, wherein said cyclic moiety is substituted or unsubstituted phenyl.

72. The method of claim 54, wherein $R^7$ is substituted or unsubstituted alkynyl.

73. The method of claim 72, wherein said substituted alkynyl is substituted with a cyclic moiety.

74. The method of claim 73, wherein said cyclic moiety is heterocyclic, cycloalkenyl, cycloalkyl, aryl, or aralkyl.

75. The method of claim 74, wherein said cyclic moiety is substituted or unsubstituted phenyl or substituted or unsubstituted cycloalkyl.

76. The method of claim 54, wherein $R^7$ is alkoxy.

77. The method of claim 54, wherein $R^5$ is hydroxy or alkylcarbonyloxy; X is $CHR^6$; $R^6$ is alkyl; and $R^8$ is hydrogen.

78. The method of claim 54, wherein $R^6$ is methyl.

79. The method of claim 77, wherein $R^7$ is hydrogen.

80. The method of claim 77, wherein $R^9$ is substituted or unsubstituted aryl.

81. The method of claim 77, wherein $R^9$ is substituted or unsubstituted alkyl or $N_3$.

82. The method of claim 77, wherein $R^2$ is hydrogen.

83. The method of claim 77, wherein $R^9$ is hydrogen and $R^8$ is alkyl.

84. The method of claim 54, wherein X is $CR^6R^{6'}$; and $R^2$, $R^5$, $R^6$, $R^{6'}$, and $R^8$ are each hydrogen, and $R^7$ is dimethyl amino.

85. The method of claim 84, wherein $R^9$ is substituted or unsubstituted aryl or aralkyl.

86. The method of claim 85, wherein said aryl is phenyl, benzofuranyl, or pyridyl.

87. The method of claim 84, wherein $R^9$ substituted or unsubstituted alkyl.

88. The method of claim 84, wherein $R^9$ is substituted or unsubstituted alkenyl.

89. The method of claim 88, wherein $R^9$ is substituted with a substituted or unsubstituted phenyl group.

90. The method of claim 54, wherein $R^9$ is substituted or unsubstituted amino.

91. The method of claim 90, wherein said amino is substituted with a heteroaryl group.

92. The method of claim 91, wherein said heteroaryl is substituted or unsubstituted thioazolyl.

93. The method of claim 54, wherein $R^9$ is substituted or unsubstituted alkynyl.

94. The method of claim 93, wherein said substituted alkynyl is substituted with a cyclic moiety.

95. The method of claim 94, wherein said cyclic moiety is heterocyclic, cycloalkenyl, cycloalkyl, aryl, or aralkyl.

96. The method of claim 95, wherein said cyclic moiety is substituted or unsubstituted phenyl or substituted or unsubstituted cycloalkyl.

97. The method of claim 54, wherein $R^9$ is substituted aminoalkyl or substituted thioalkyl.

98. The method of claim 54, wherein said substituted tetracycline compound is selected from the group consisting of:

145
-continued
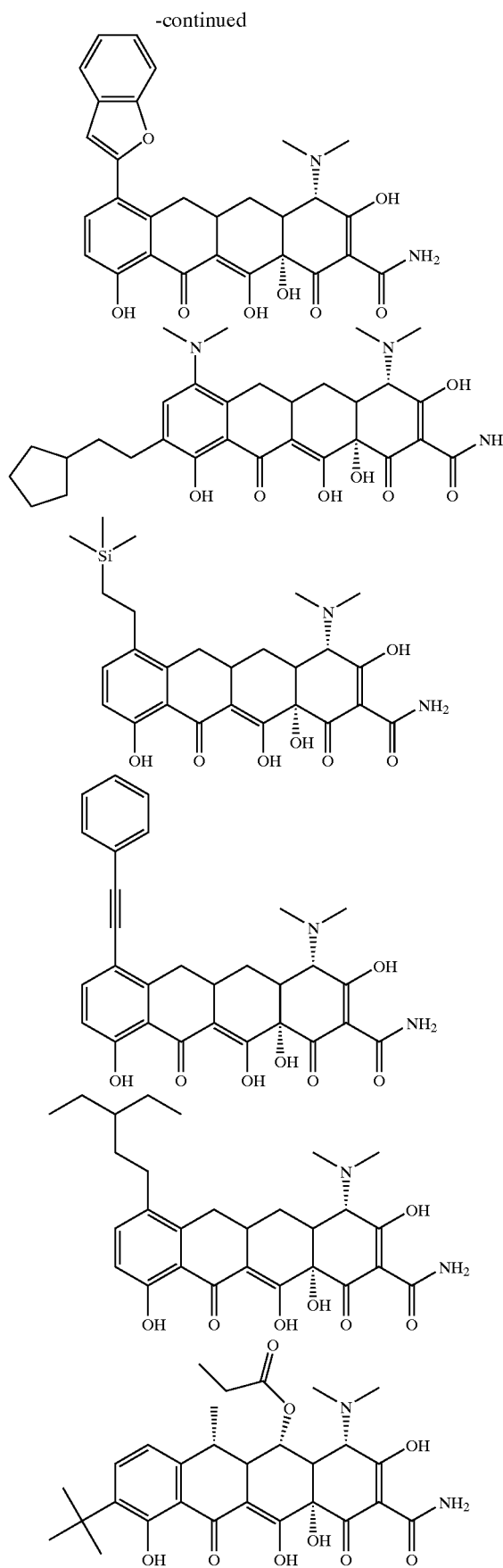
146
-continued
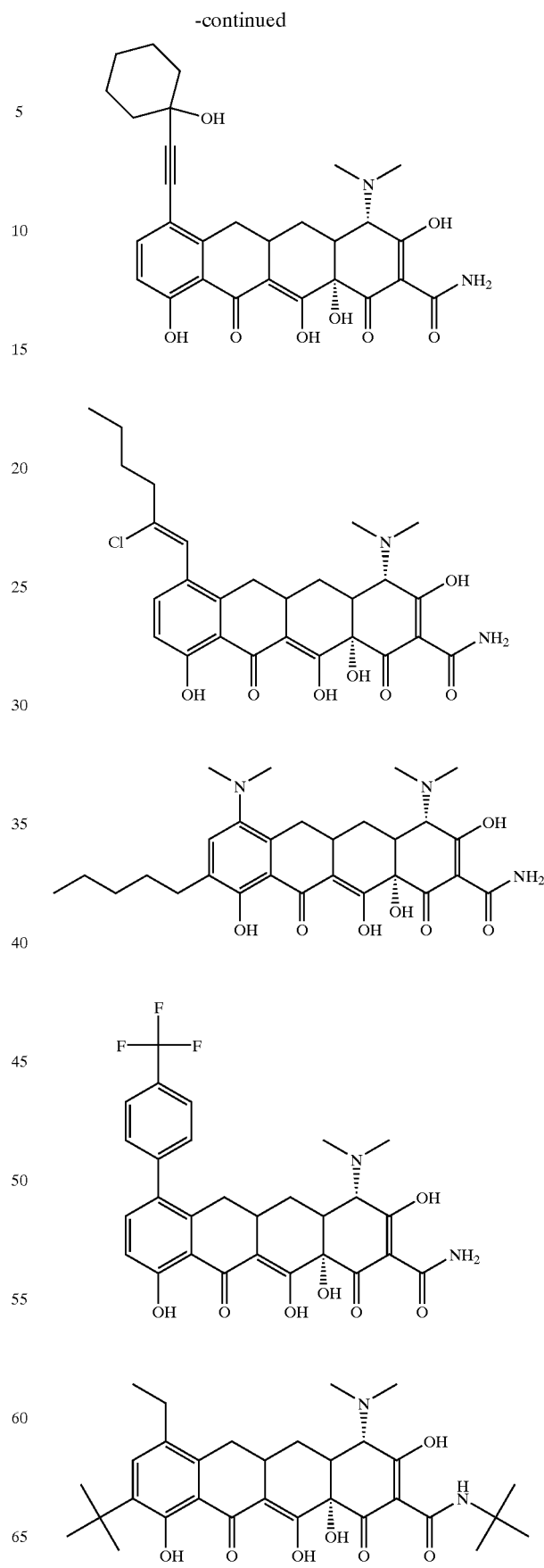

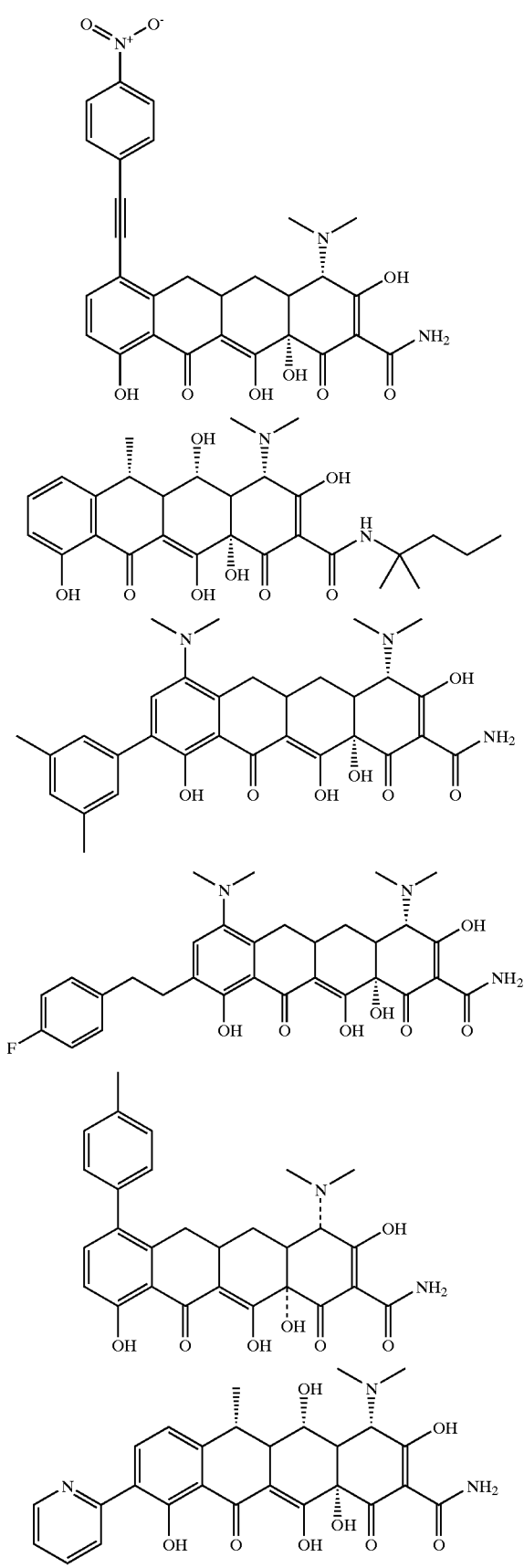
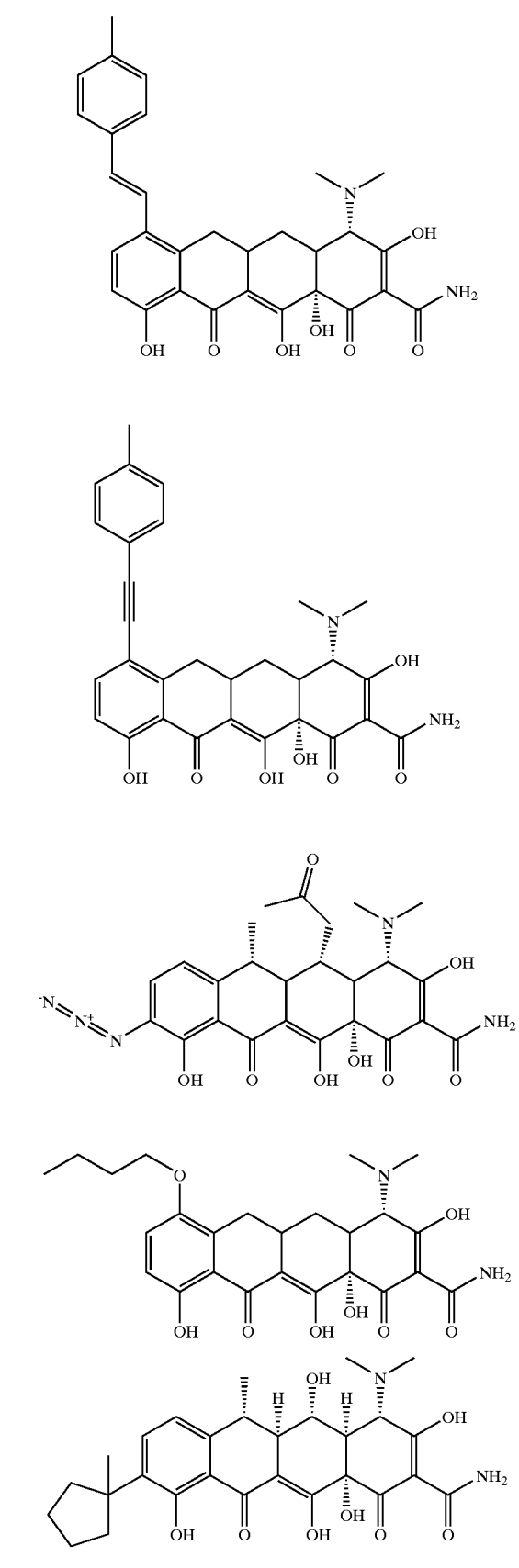

149
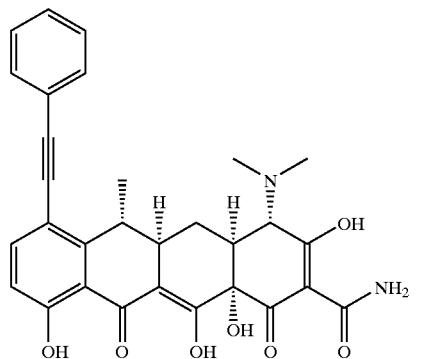
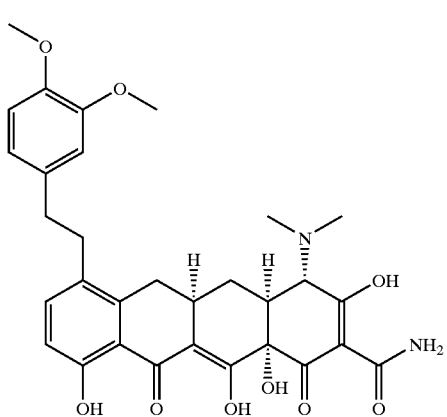
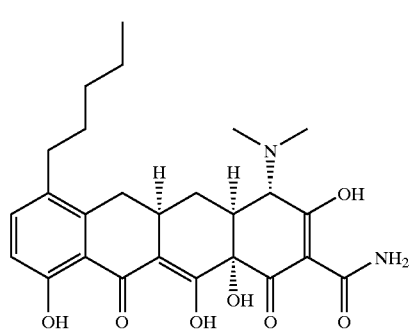
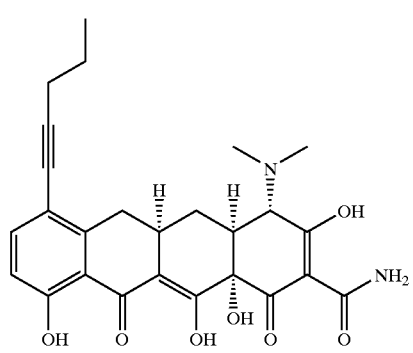
150
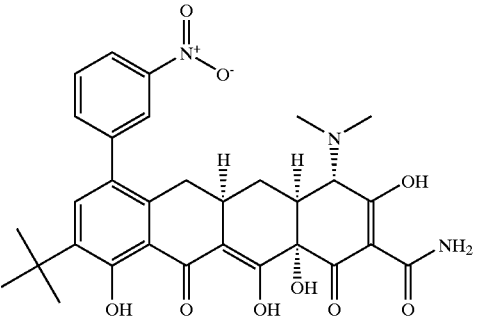

-continued

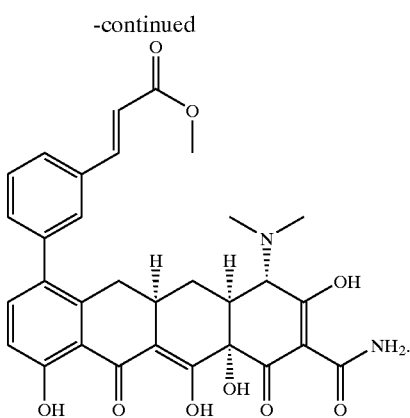

99. The method of claim 54, wherein said fungus is associated with a fungus selected from the group consisting of *C. neoformans, C. tropicalis, C. parapsilosis, C. lusitaniae, C. krusei, C. guilliermondii, C. glabrata, C. dubliniensis,* or *C. albicans.*

100. The method of claim 54, wherein said fungal associated disorder is histoplasmosis, systemic candidiasis, aspergillosis, blastomycosis, coccidioidomycosis, paracoccidioidoniycosis, cryptococcosis, dermatophyte infections, tinea pedis, tinea cruris, candidiasis, actinomycosis, mycoses, aspergillosis, candidosis, chromomycosis, entomophthoromycosis, epizootic lymphangitis, geotrichosis, histoplasmosis, mucormycosis, mycetoma, north american blastomycosis, oomycosis, paecilimycosis, penicilliosis, rhinosporidiosis, or sprotrichiosis.

101. The method of claim 54, wherein said subject is a plant.

102. The method of claim 54, wherein said subject is a mammal.

103. The method of claim 102, wherein said mammal is a human.

104. The method of claim 102, wherein said mammal is immunocompetent.

105. The method of claim 102, wherein said mammal is immunocompromised.

106. The method of claim 105, wherein said human is immunodeficient.

107. The method of claim 106, wherein said human has AIDS.

108. The method of claim 105, wherein said human has undergone chemotherapy.

109. The method of claim 54, further comprising the administration of a pharmaceutically acceptable carrier.

110. A method of killing fungus, comprising contacting said fungus with a fungicidal amount of a substituted tetracycline compound, such that said fungus is killed.

111. The method of claim 110, wherein said substituted tetracycline compound is of the formula:

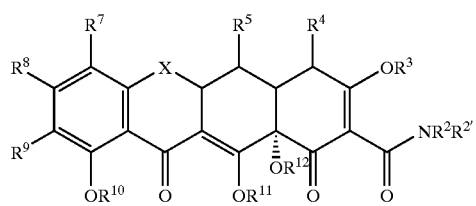

(I)

X is $CHC(R^{13}Y'Y)$, $CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, hydroxyl, halogen, or hydrogen;

$R^3$, $R^{11}$ and $R^{12}$ are each hydrogen, or a pro-drug moiety;

$R^{10}$ hydrogen, a prodrug moiety, or linked to $R^9$ to form a ring;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —$(CH_2)_{0-3}NR^{7c}C(=W')WR^{7a}$;

$R^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —$(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

112. The method of claim 1 or 53, wherein said tetracycline compound is selected from the group consisting of:

153
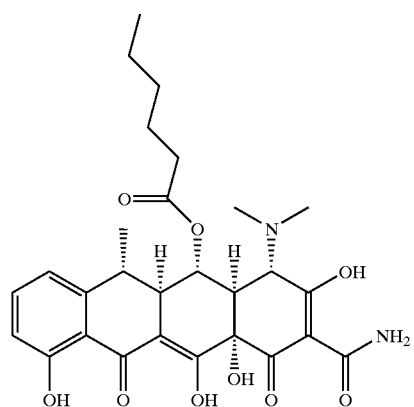
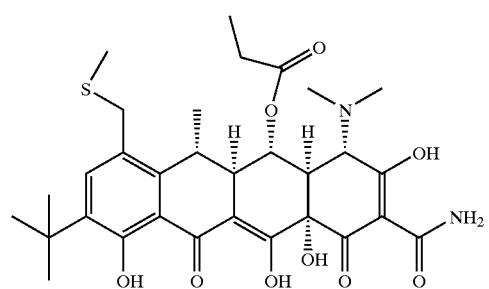
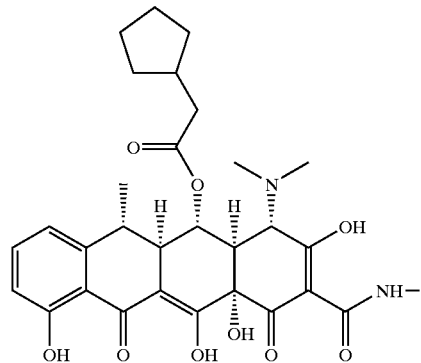
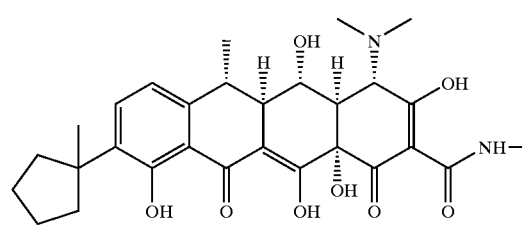
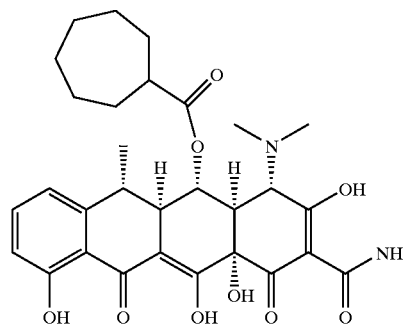
154
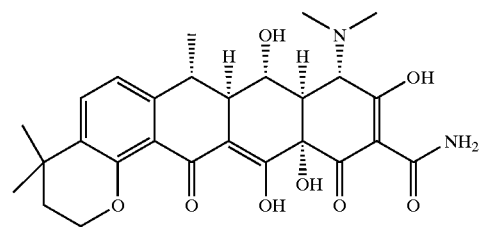
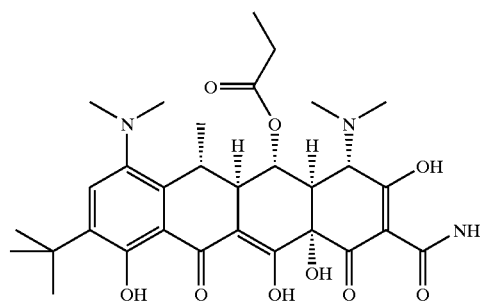
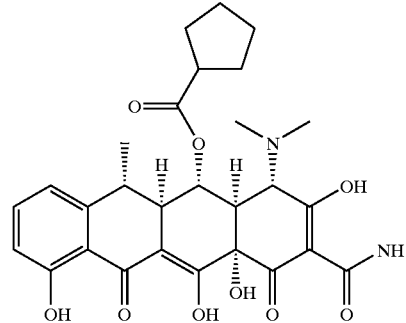
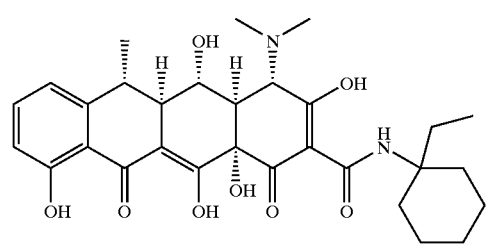
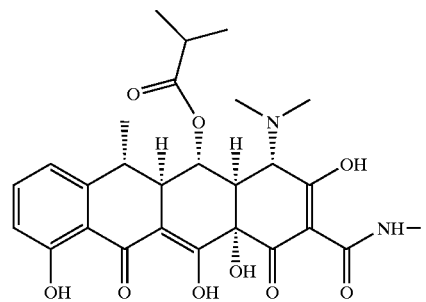

-continued
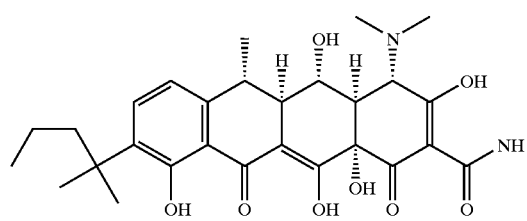
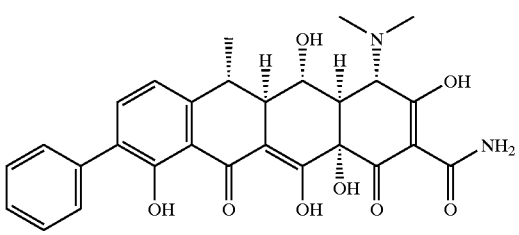
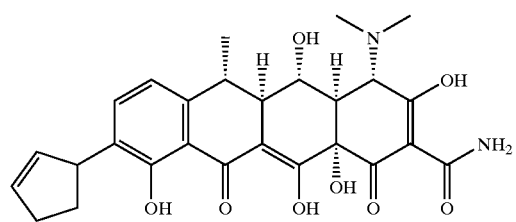
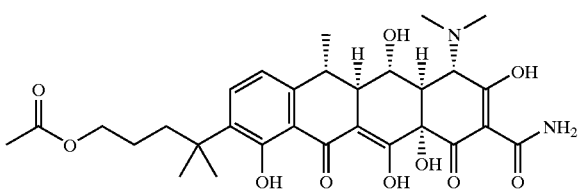
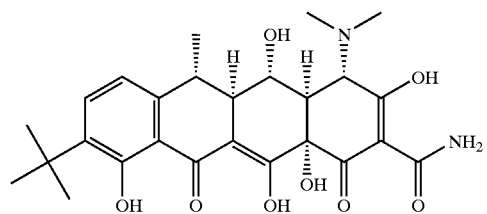
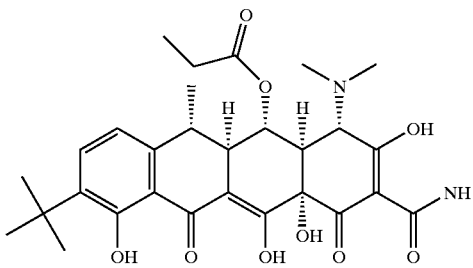
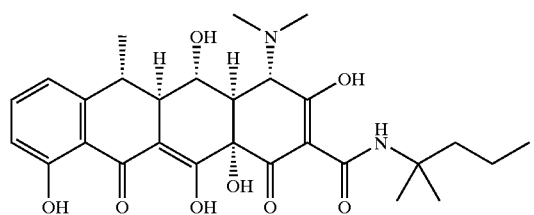
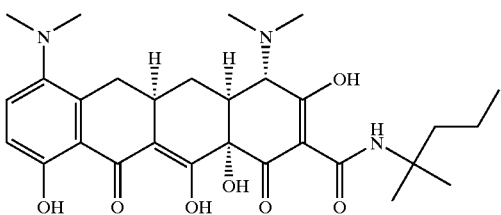
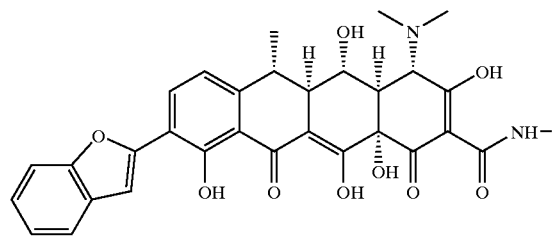
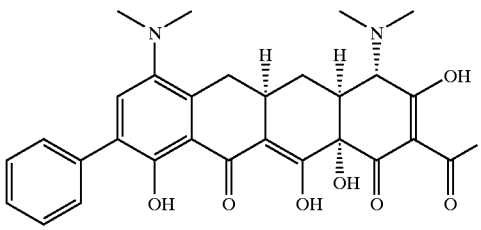
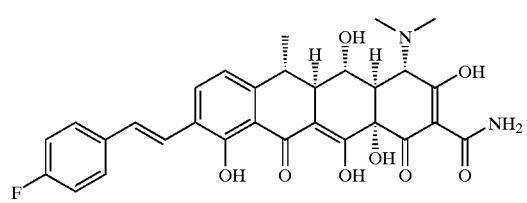
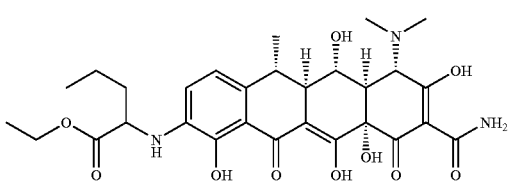
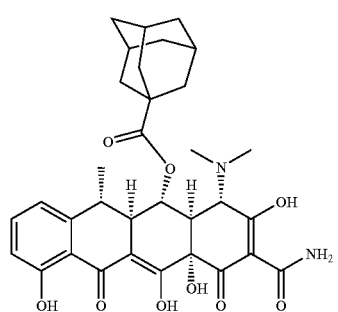
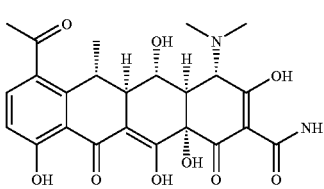

-continued
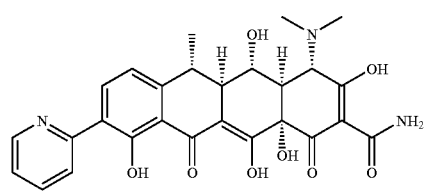
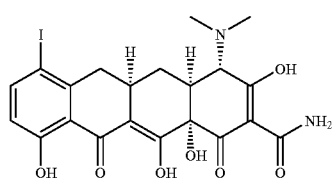
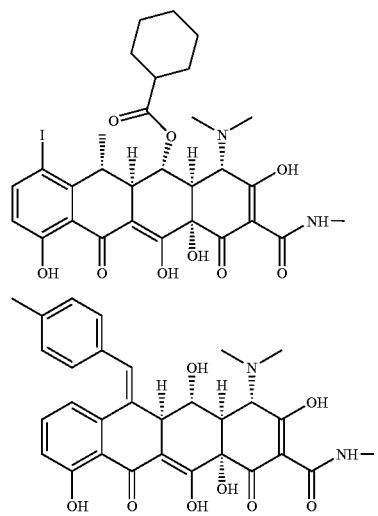
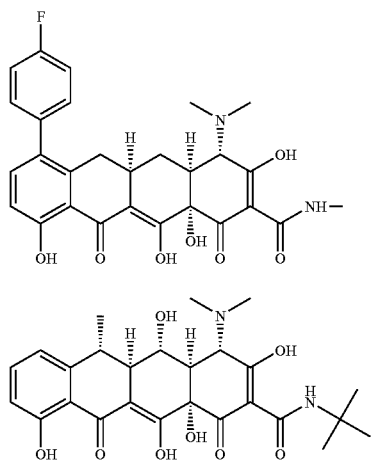
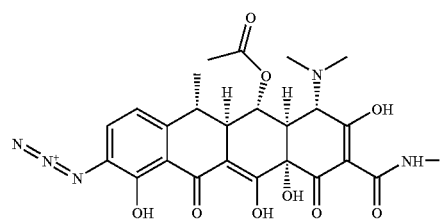
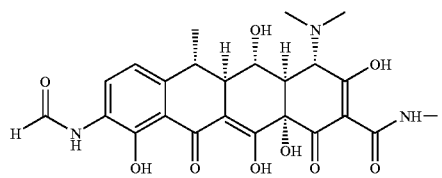
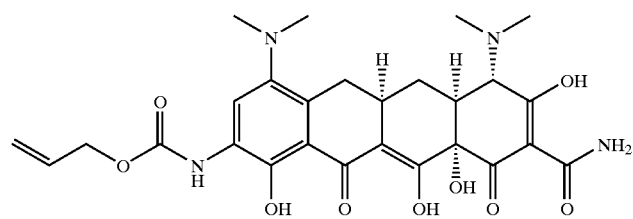
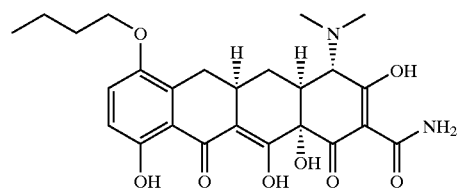
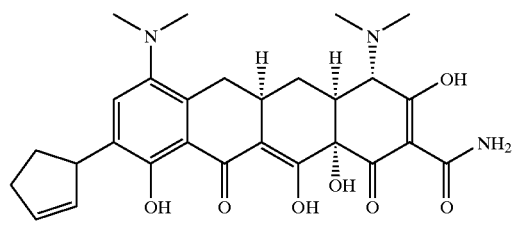
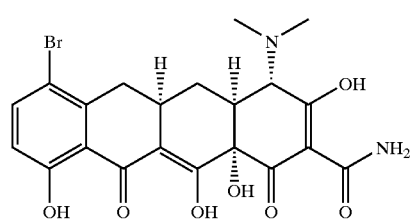
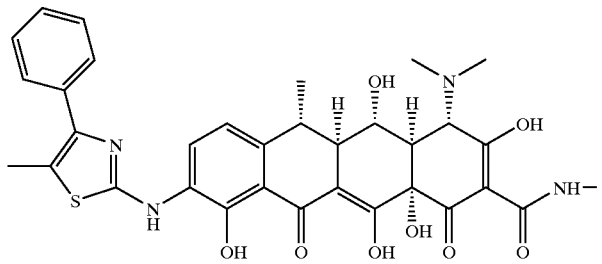

159            160
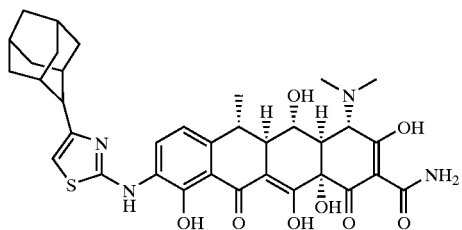 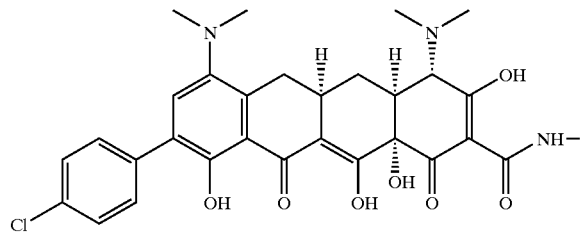
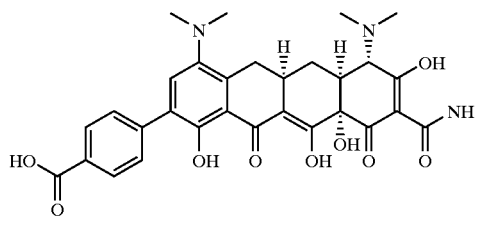 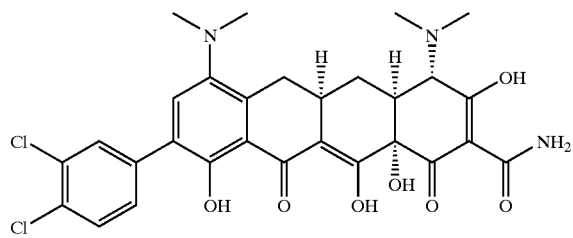
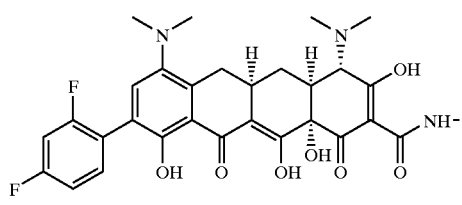 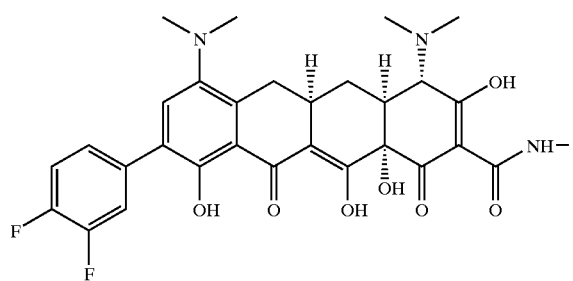
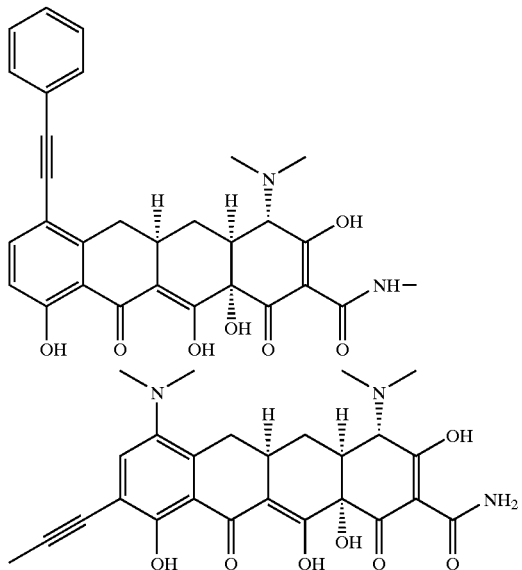 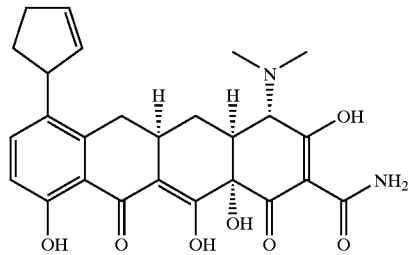
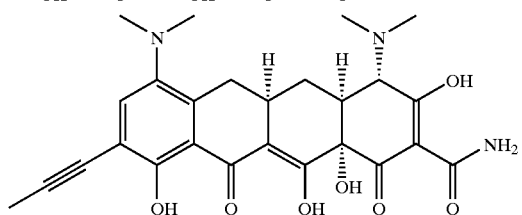 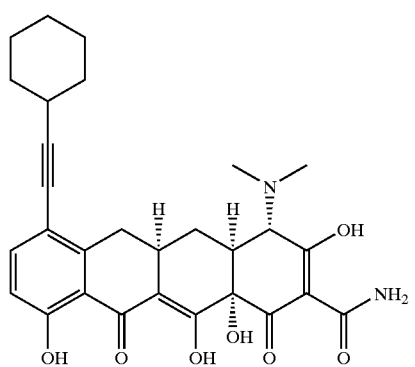

161
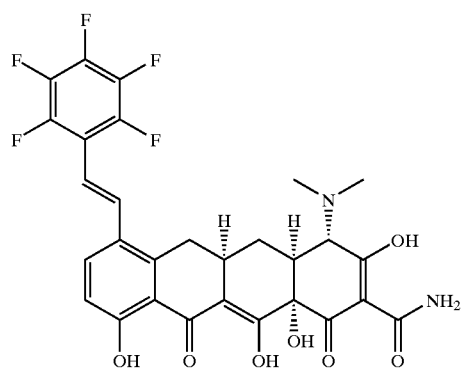
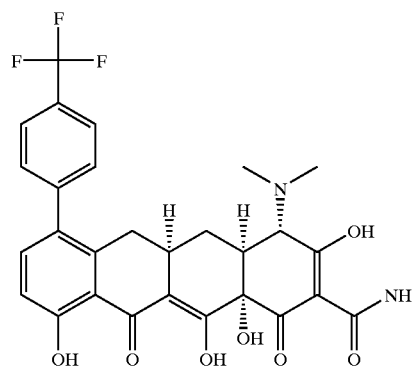
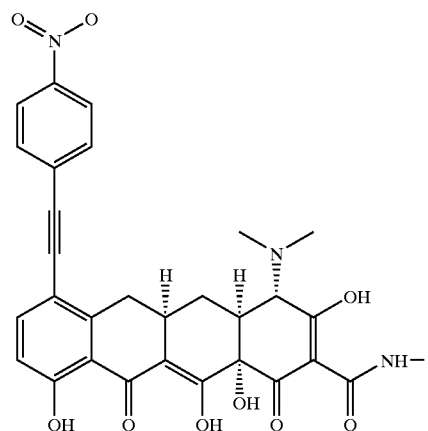
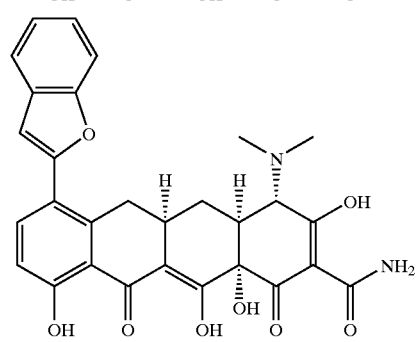
162
-continued
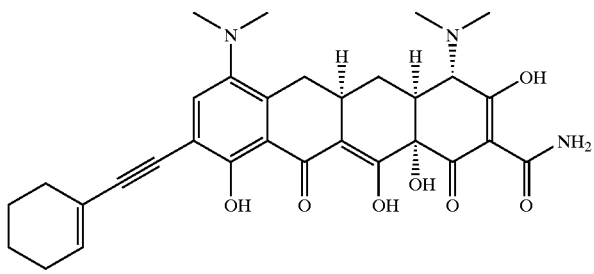
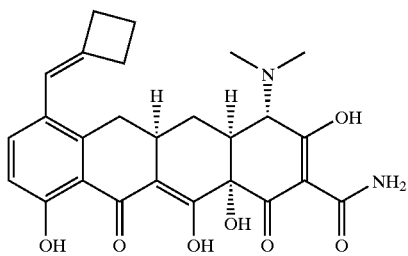
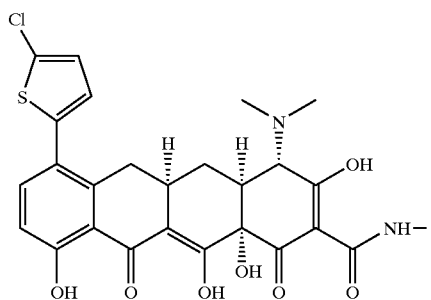
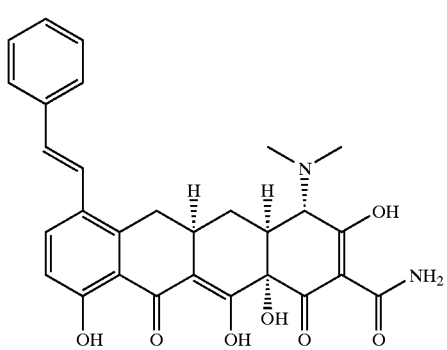

163
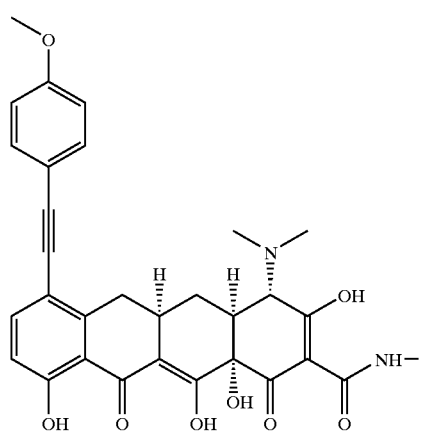
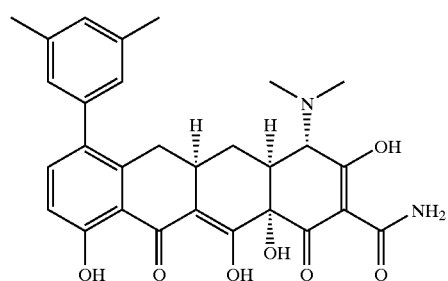
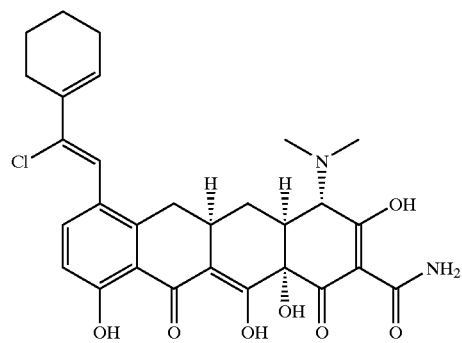
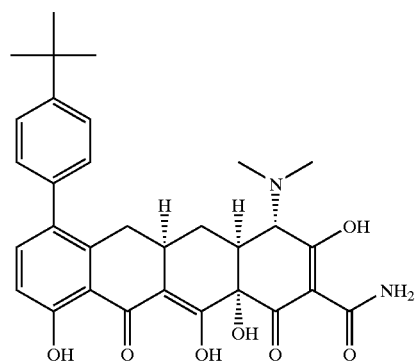
164
-continued
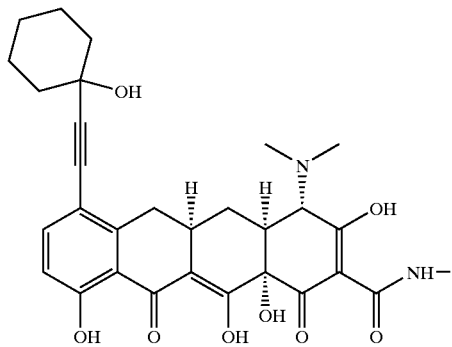
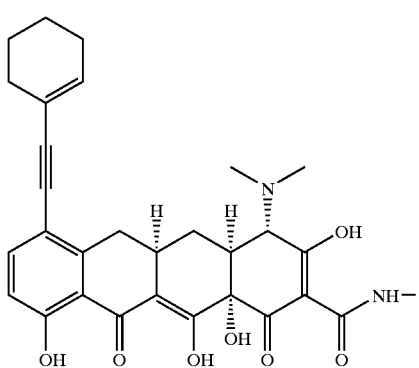
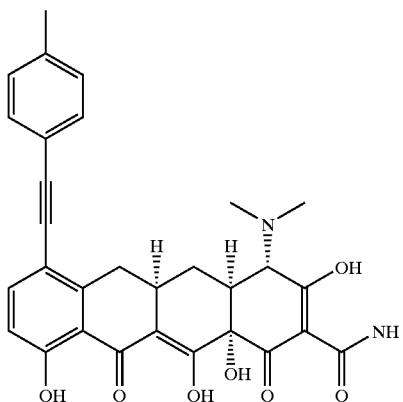
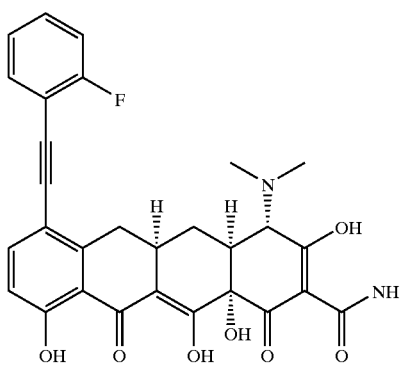

165
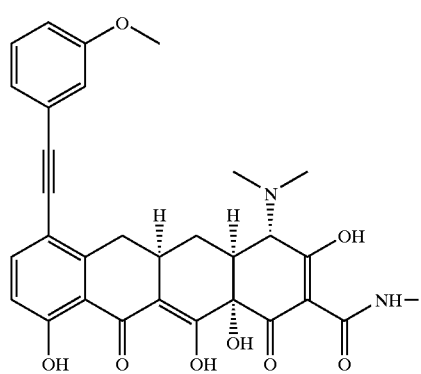
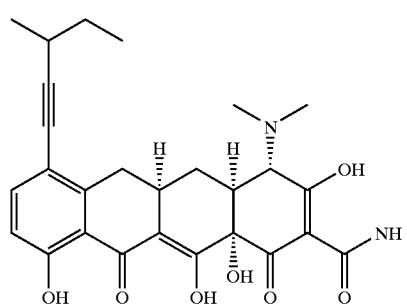
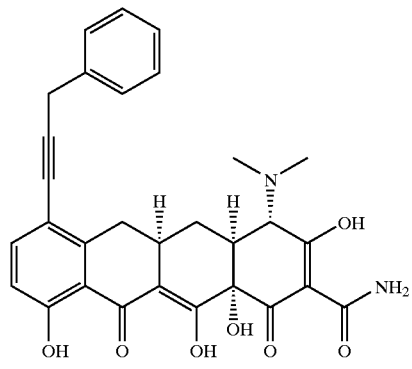
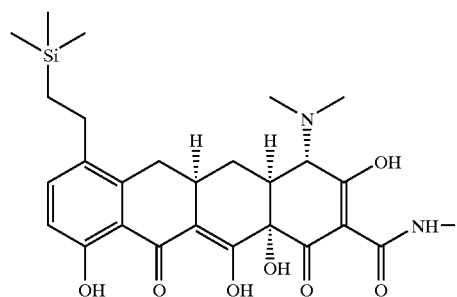
166
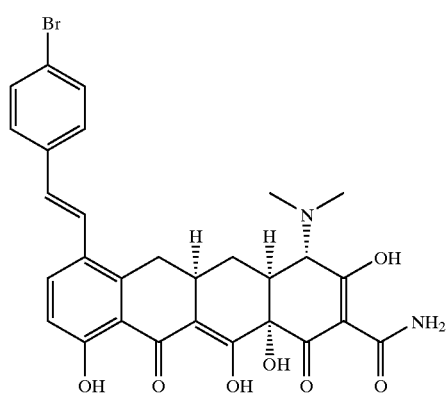
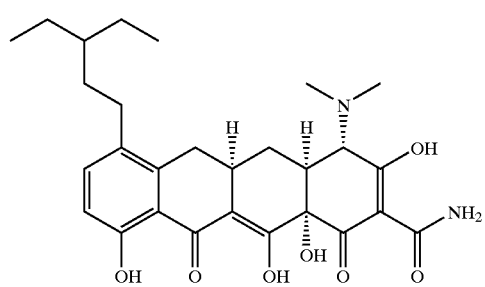
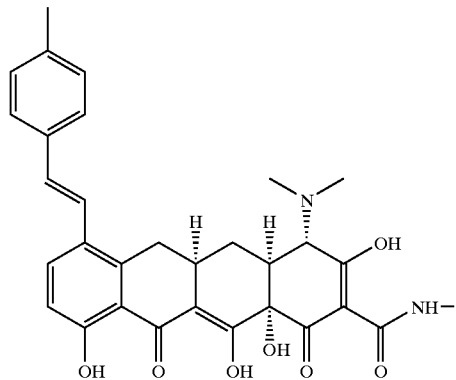
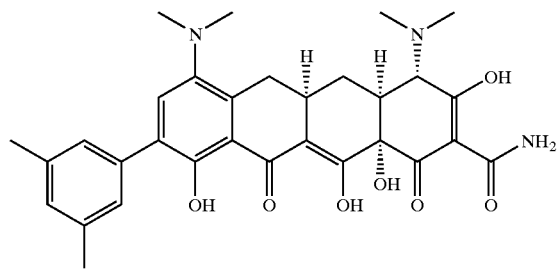

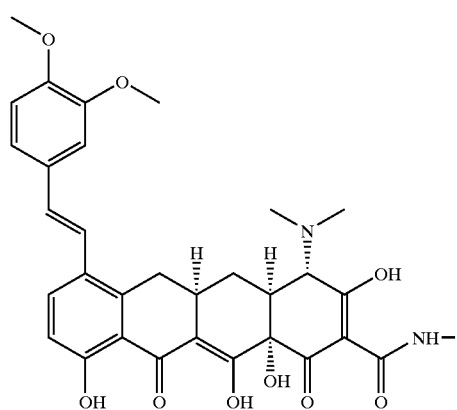
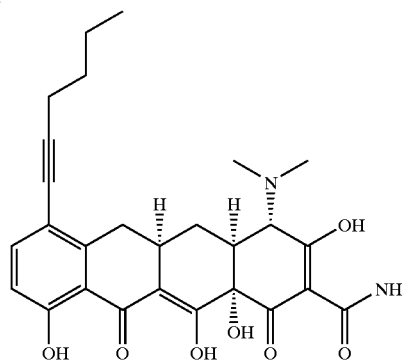
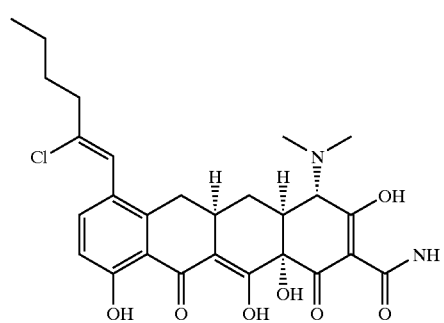
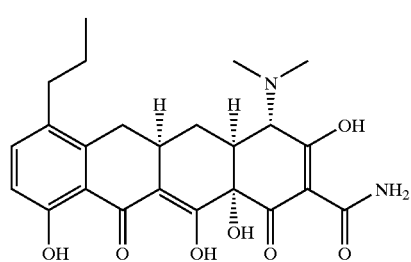
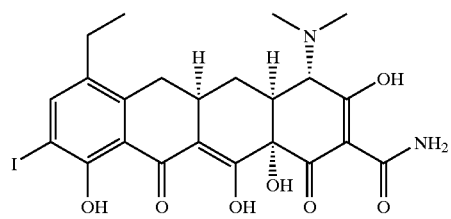
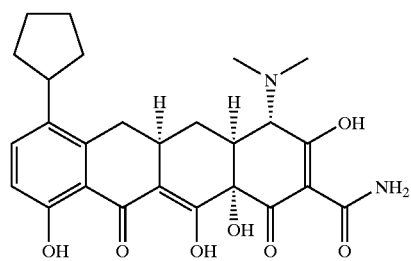
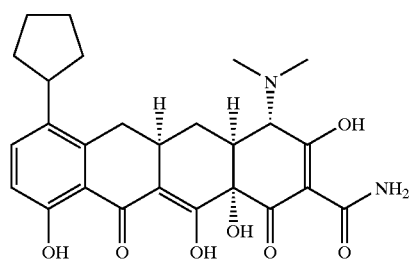
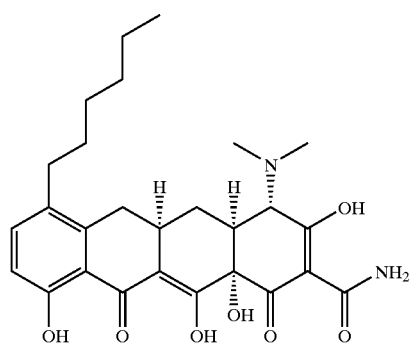
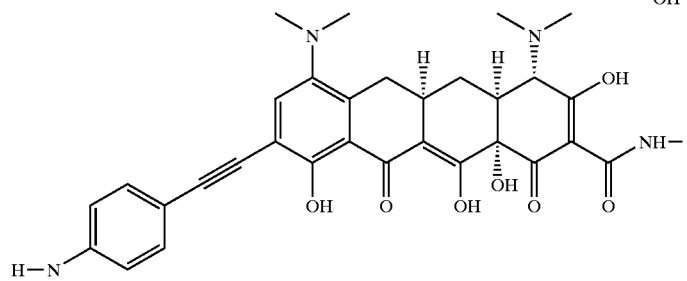

169 170
-continued
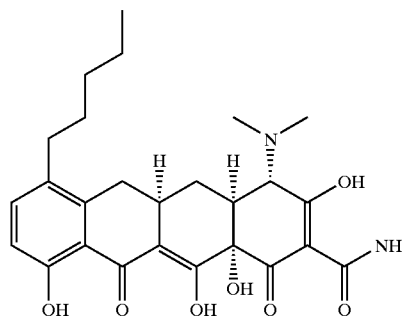 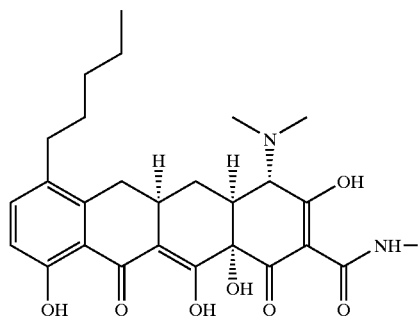
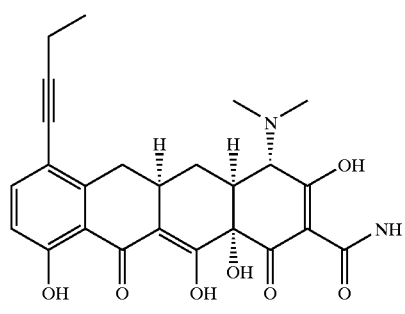 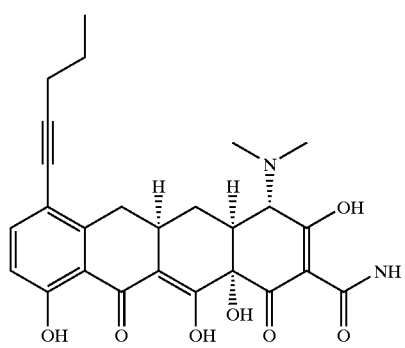
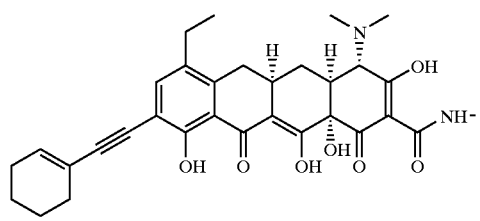 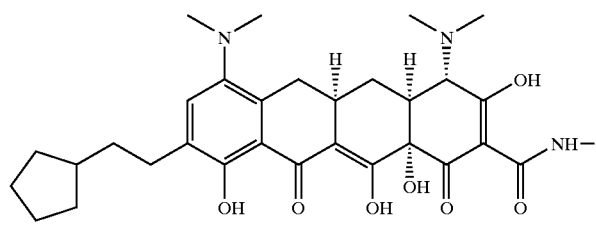
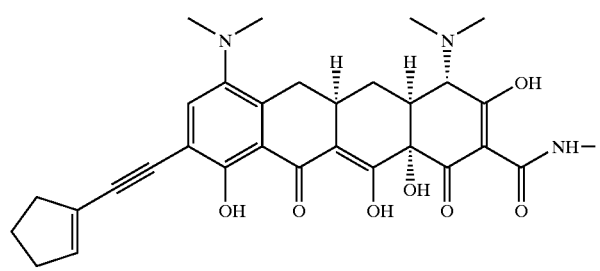 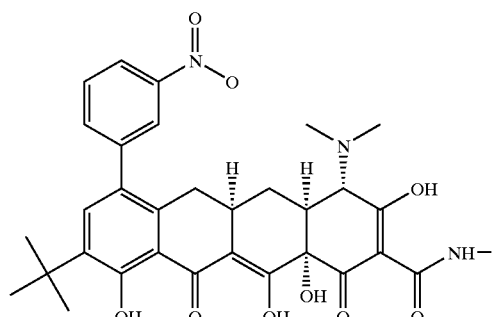
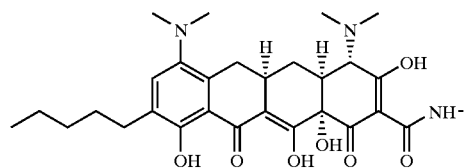 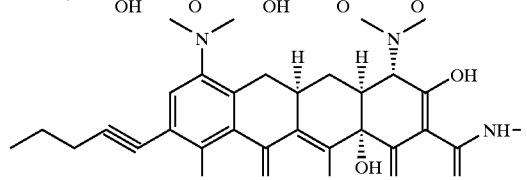
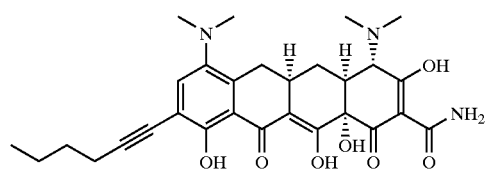 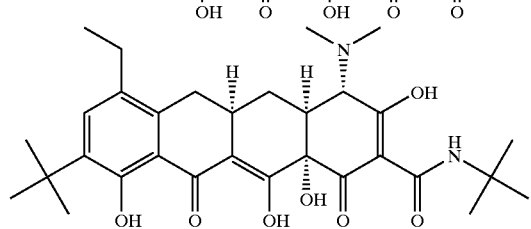

171
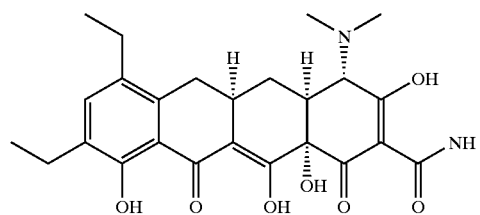
172
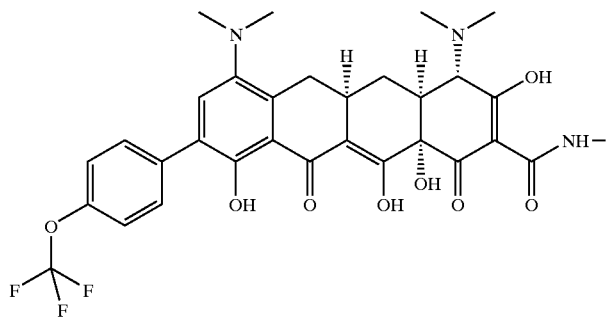
-continued
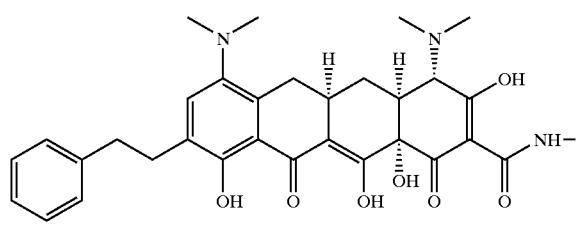
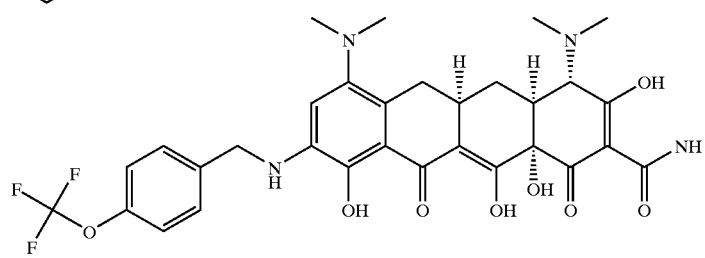
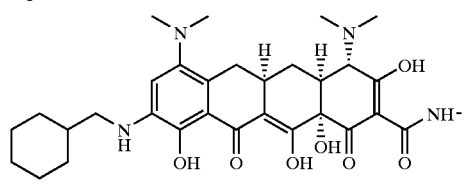
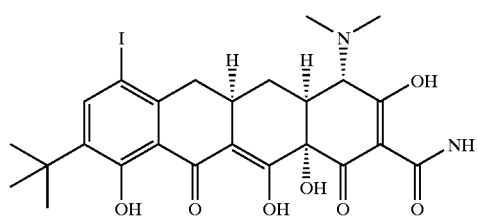
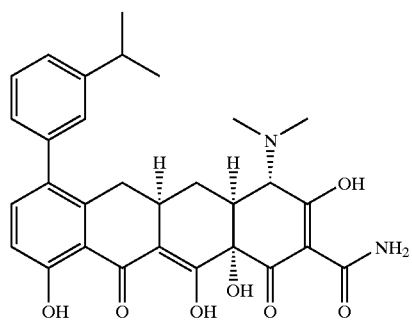
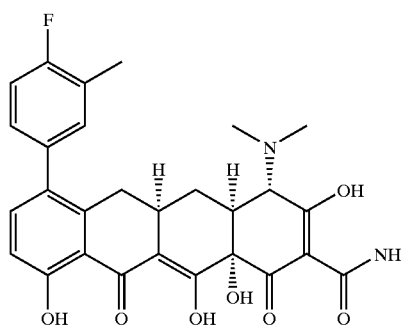
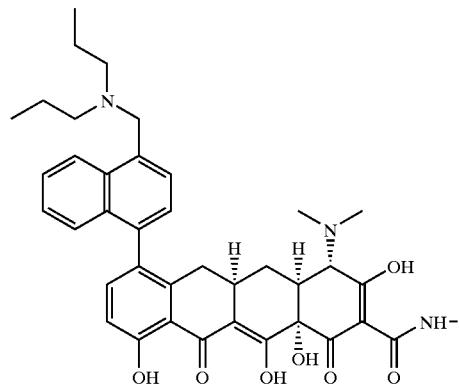
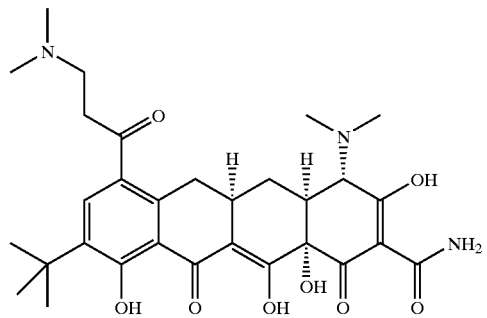

173
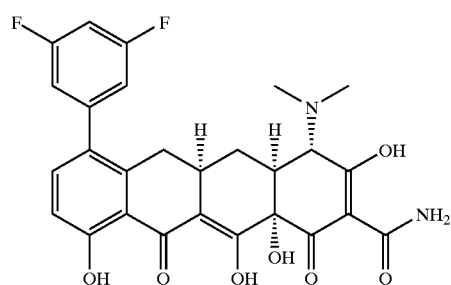
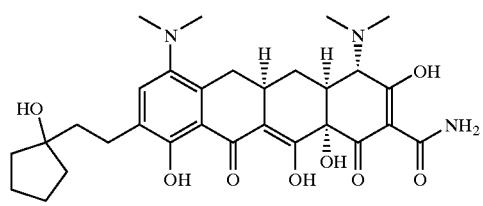
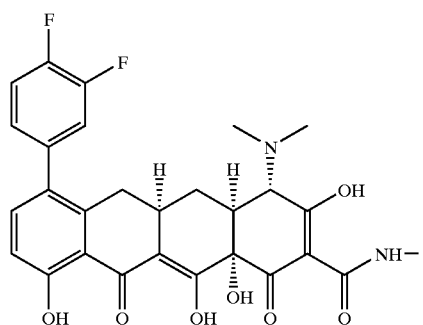
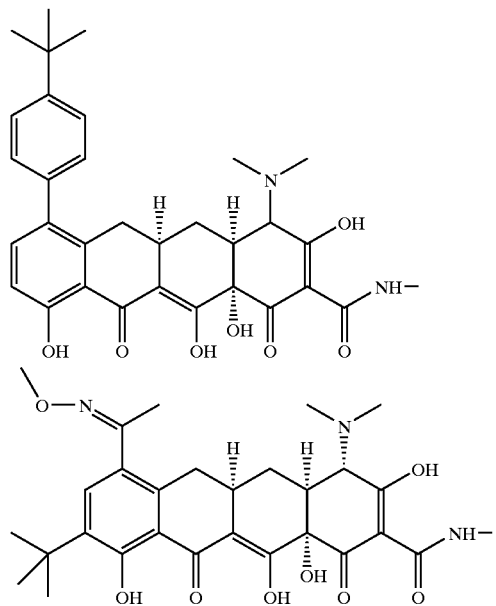
174
-continued
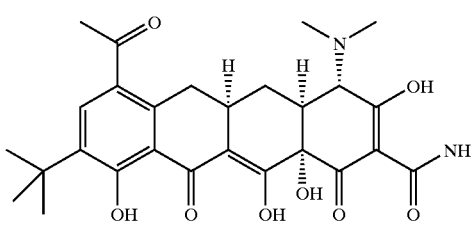
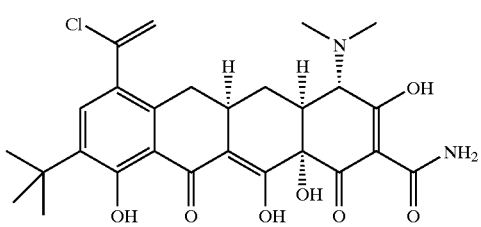
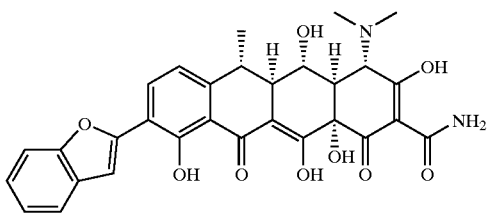
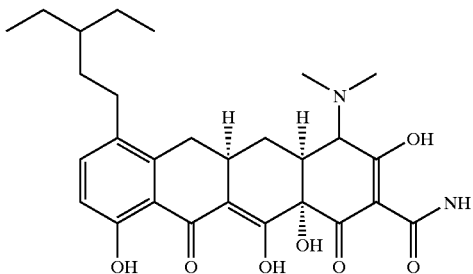
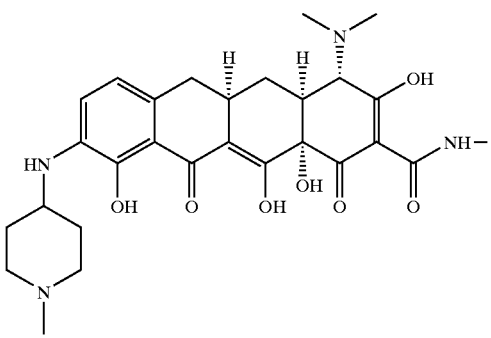

175
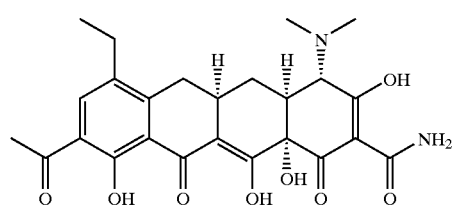
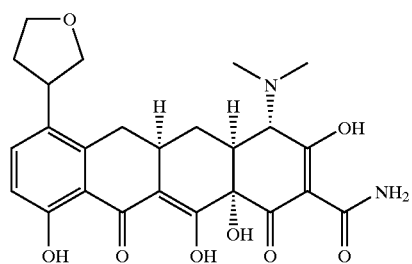
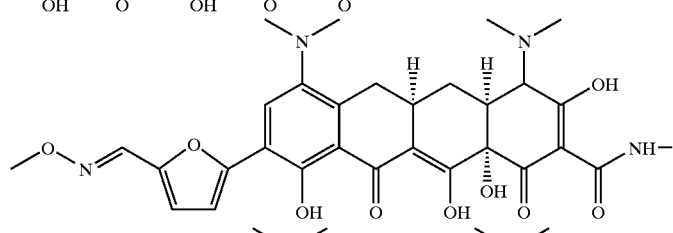
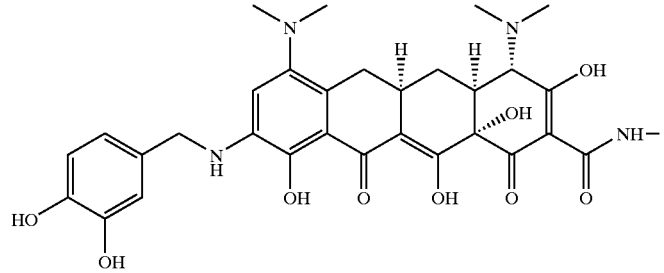
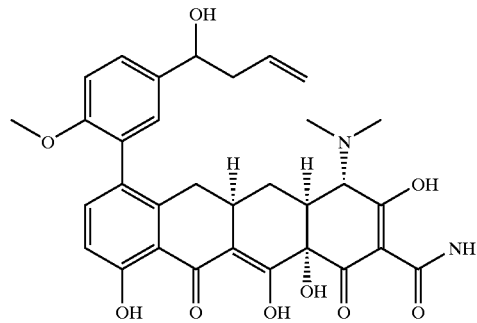
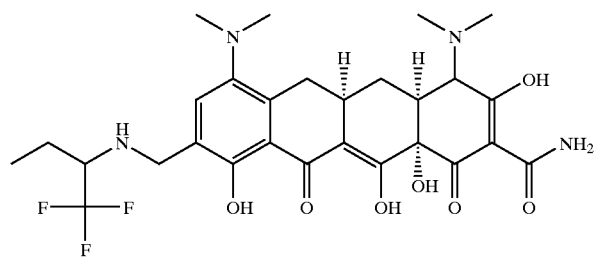
176
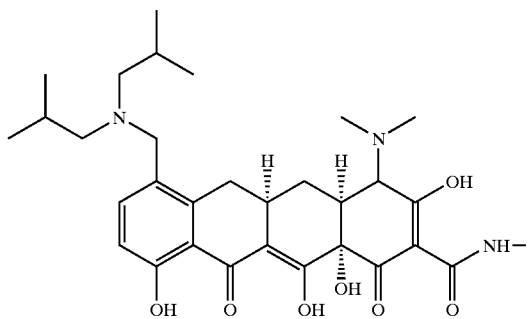
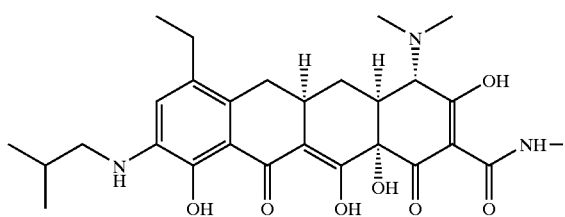
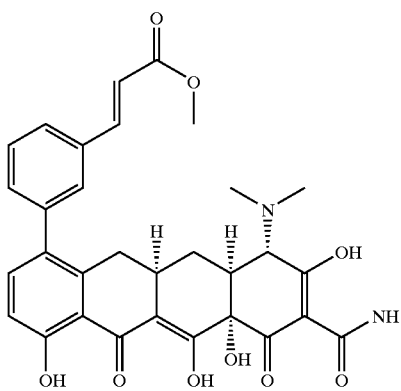

113. A method for inhibiting the growth of a fungus, comprising contacting said fungus with an effective amount of a substituted tetracycline compound, such that the growth of said fungus is inhibited, wherein said substituted tetracycline has an MIC for said fungus which is 90% or less than that of unsubstituted minocycline for said fungus.

114. A method for treating a fungal associated disorder in a subject, comprising administering to said subject an effective amount of a substituted tetracycline compound such that said subject is treated for said fungal associated disorder, wherein said substituted tetracycline has an MIC for said fungus which is 90% or less than that of unsubstituted minocycline for said fungus.

* * * * *